(12) United States Patent
Andocs et al.

(10) Patent No.: US 10,792,483 B2
(45) Date of Patent: Oct. 6, 2020

(54) TUMOR VACCINATION

(71) Applicant: XAX KFT., Paty (HU)

(72) Inventors: Gabor Andocs, Erd (HU); Oliver Szasz, Paty (HU); Andras Szasz, Paty (HU); Nora Iluri, Los Gatos, CA (US)

(73) Assignee: XAX KFT., Paty (HU)

( * ) Notice: Subject to any disclaimer, the term of this patent is extended or adjusted under 35 U.S.C. 154(b) by 706 days.

(21) Appl. No.: 14/424,027

(22) PCT Filed: Aug. 26, 2013

(86) PCT No.: PCT/EP2013/067653
§ 371 (c)(1),
(2) Date: Feb. 25, 2015

(87) PCT Pub. No.: WO2014/033097
PCT Pub. Date: Mar. 6, 2014

(65) Prior Publication Data
US 2015/0217099 A1    Aug. 6, 2015

Related U.S. Application Data

(60) Provisional application No. 61/744,008, filed on Sep. 17, 2012.

(30) Foreign Application Priority Data

Aug. 26, 2012 (EP) ..................... 12181821

(51) Int. Cl.
*A61M 37/00* (2006.01)
*A61N 1/40* (2006.01)
(Continued)

(52) U.S. Cl.
CPC .......... *A61M 37/00* (2013.01); *A61K 31/282* (2013.01); *A61K 35/74* (2013.01); *A61K 36/00* (2013.01);
(Continued)

(58) Field of Classification Search
CPC .......... A61M 37/00; A61M 2037/0007; A61K 31/282; A61K 35/74; A61K 36/00; A61K 36/24; A61K 38/193; A61N 1/40
(Continued)

(56) References Cited

U.S. PATENT DOCUMENTS 4,613,591 A * 9/1986 Aburada .............. A61K 36/232
514/34
4,712,559 A  12/1987 Turner
(Continued)

FOREIGN PATENT DOCUMENTS

EP  1916013 A1  10/2007
EP  2174689 A1  4/2010
(Continued)

OTHER PUBLICATIONS

Udagawa, Masaru, et al. "Enhancement of Immunologic Tumor Regression by Intratumoral Administration of Dendritic Cells in Combination with Cryoablative Tumor Pretreatment and Bacillus Calmette-Guerin Cell Wall Skeleton Stimulation". Dec. 15, 2006. Clinical Cancer Research. (12) (24). 7465-7475.*
(Continued)

*Primary Examiner* — Amanda K Hulbert
*Assistant Examiner* — Natasha Patel
(74) *Attorney, Agent, or Firm* — Knobbe, Martens, Olson & Bear, LLP

(57) ABSTRACT

The present invention relates to a vaccine composed of at least one immune stimulant and radiofrequency waves using capacitive coupling and to a method, especially an in-situ and in vivo vaccination method for treatment of primary cancer and its metastases even in disseminated cell-states, which cannot be detected by presently available imaging methods or for prevention of relapse of the cancer disease, and especially for enabling and supporting the patient's own
(Continued)

immune system to recognize and kill the cancer cells and to build up a memory to prevent relapse of a cancer disease.

6 Claims, 52 Drawing Sheets

(51) Int. Cl.
*A61K 35/74* (2015.01)
*A61K 31/282* (2006.01)
*A61K 36/00* (2006.01)
*A61K 36/24* (2006.01)
*A61K 38/19* (2006.01)

(52) U.S. Cl.
CPC ............ *A61K 36/24* (2013.01); *A61K 38/193* (2013.01); *A61N 1/40* (2013.01); *A61M 2037/0007* (2013.01)

(58) Field of Classification Search
USPC ...................................... 607/3, 65, 100, 101
See application file for complete search history.

(56) References Cited

U.S. PATENT DOCUMENTS

| | | | |
|---|---|---|---|
| 5,099,756 A * | 3/1992 | Franconi ................ | A61N 1/403 219/673 |
| 2004/0138709 A1 | 7/2004 | Brighton | |
| 2004/0230263 A1 | 11/2004 | Samulski | |
| 2007/0239213 A1 * | 10/2007 | Palti ..................... | A61K 31/337 607/3 |
| 2009/0018613 A1 | 1/2009 | Brighton | |
| 2011/0106226 A1 | 5/2011 | Szasz et al. | |
| 2011/0208182 A1 * | 8/2011 | Szasz .................... | A61N 1/403 606/33 |
| 2012/0065714 A1 | 3/2012 | Szasz et al. | |

FOREIGN PATENT DOCUMENTS

| | | | | |
|---|---|---|---|---|
| EP | 2780024 B1 | 5/2016 | | |
| WO | WO 2009/092619 A2 | 7/2009 | | |
| WO | WO 2010043372 A1 * | 4/2010 | ......... | A61B 18/1206 |
| WO | WO-2010043372 A1 * | 4/2010 | ......... | A61B 18/1206 |
| WO | WO 2011/078676 A1 | 6/2011 | | |

OTHER PUBLICATIONS

Wadler, Scott, et al. "Phase II Clinical Trial with 5-Fluorouracil Recombinant Interferon-a-2b, and Cisplatin for Patients with Metastatic or Regionally Advanced Carcinoma of the Esophagus." Jul. 1, 1996. American Cancer Society. vol. 78 Isuuse 1. pp. 30-34.*

Siddik, Zahid. "Cisplatin: mode of cytotoxic action and molecular basis of resistance." Oct. 20, 2003. Oncogene. https://www.nature.com/articles/1206933 Retrieved Aug. 24, 2018.*

Siddik, Zahid. "Cisplatin: mode of cytotoxic action and molecular basis of resistance." Oct. 20, 2003. Oncogene.https://www.nature.conn/articles/1206933 Retrieved Aug. 24, 2018. (Year: 2003).*

Margolin, Kim, et al. "Ipilinnunnab in patients with melanoma and brain metastases: an open-label, phase 2 trial." May 2012. The Lancet: Oncology. vol. 13, Issue 5. pp. 459-465. (Year: 2012).*

Sersa, G, et al. "Electrochennotherapy with cisplatin: the systemic antitumor effectiveness of cisplatin can be potentiated locally by the application of electric pulses in the treatment of malignant melanoma skin metastases." 2000. Melanoma Research. vol. 10. 381-385 (Year: 2000).*

Oettgen, H.F., et al. "Treatment of Cancer with Immunomodulators: Corynebacterium parvum and Levamisole." May 1976. Medical Clinics of North America. vol. 60 Issue 3. Abstract Only. (Year: 1976).*

Okutomi, T., et al. "Clinical effects of adjuvant therapy using Z-100 (Ancer 20 injection) for oral cancer—prevention of stomatitis and hematopoietic impairment." Jan. 1, 2000. Voume 27 Issue 1. Abstract Only. (Year: 2000).*

Xiuying, Yuan, et al. "Observations on the treatment of 14 cases of advanced gastric cancer with Inj. Xiao-Ai-Ping". Jun. 1996. Shanghai Medical and Pharmaceutical Journal. Abstract Only. (Year: 1996).*

Gilewski, Teresa, et al. "Vaccination of High-Risk Breast Cancer Patients with Mucin-1 (MUC1) Keyhole Limpet Hemocyanin Conjugate plus QS-21". May 2000. Clinical Cancer Research. vol. 6 Issue 5. Abstract Only. (Year: 2000).*

Ohnishi, Yasuharu, et al. "Oral Administration of a Kampo (Japanese Herbal) Medicine Juzen-taiho-to Inhibits Liver Metastasis of Colon 26-L5 Carcinoma Cells." 23 Aug. 2005. Japanese Journal of Cancer Research. Abstract Only. (Year: 2005).*

Yui, Satoko, et al. "Characteristics of Apoptosis in HCT116 Colon Cancer Cells Induced by Deoxycholic Acid." Aug. 2005. The Journal of Biochemistry. vol. 138 Issue 2. Abstract Only. (Year: 2005).*

Vergati, et al. "Strategies for Cancer Vaccine Development"; *J. Biomed. Biotech.* 2010, Article ID 596432, doi:10.1155/2010/596432, 14 pages.

PCT International Search Report and Written Opinion of the International Searching Authority. 14 pages dated Nov. 27, 2013.

T. Vancsik et al., "Modulated electro0hypertherna induced I oco-Oregional and systemic tumor destruction in colorectal cancer allografts." *Journal of Cancer* 2018; vol. 9: pp. 41-53.

Lijun Zhao and Yu J. Cao, "Engineered T Cell Therapy for Cancer in the Clinic." *Frontiers in Immunology* published Oct. 11, 2019; doi: 10.3389/immu.2019.02250.

* cited by examiner

TUMOR VACCINATION

BACKGROUND OF THE INVENTION

Radio Frequency based Methods and Cancer Currently, a method using radiofrequency current for the treatment of cancer is the radiofrequency ablation method (RFA), which is quite different from the present invention. The RFA method is an invasive method using RF for burning-out the lesion. The RFA method applies "antennas" in form of needles (see FIG. 1), which are inserted intratumoral into the solid tumor, and the applied local current becomes so large, that the tumor is burned thereby causing vehement necrosis.

Such conditions are strictly avoided by the present invention. The RFA method is a medical procedure where part of the electrical conduction system of the heart, tumor or other dysfunctional tissue is ablated using the heat generated from the high frequency alternating current to treat a medical disorder. An advantage of RF current (over previously used low frequency AC or pulses of DC) is that it does not directly stimulate nerves or heart muscle and can therefore often be used without the need for general anesthetic. RFA procedures are performed under image guidance (such as X-ray screening, CT scan or ultrasound) by an interventional pain specialist such as an anesthesiologist, interventional radiologist or a cardiac electrophysiologist, a subspecialty of cardiologists.

Another medical procedure using radiofrequency current for treatment of cancer is intravascular stimulation with pulsed radiofrequency (see WO 2011/078676). This method is useful for treatment of both solid and blood borne tumors and involves the insertion of a needle-like electrode with an impedance of less than 10000 in a blood vessel and the delivery of an electrical signal of current pulses in a radiofrequency range with a voltage of 10-80 V in pulse bursts with a duration of 0.1-100 ms and burst frequency of 1/s-20/s. It is stated that intravascular pulsed radiofrequency stimulation is boosting the immune system by stimulating and attracting the lymphocytes, which result into attack of tumor cells. The intravascular radiofrequency stimulation is invasive and leads to the heating of blood in the entire body. Moreover, the immune response induced by intravascular radiofrequency stimulation is non specific. Therefore, no immune-reaction is targeting the "hidden" tumor cells, which are unaffected by such medical procedure.

WO 2011/078676 discloses also the possibility to use intravascular stimulation with pulsed radiofrequency in combination with vaccination. However, for this in WO 2011/078676 the role of the intravascular stimulation with pulsed radiofrequency is to boost the immune system, so that the immune reactions induced by the vaccination therapy are amplified. At our knowledge, up to present several cancer vaccines are in development by companies but only one product, was given full approval (by the FDA) for late stage prostate cancer. Provenge® (or sipuleucel-T), is an immunotherapy for prostate cancer consisting of a mixture of the patient's own blood cells that have been incubated "ex vivo" with PAP-GM-CSF fusion protein. So far, no cancer vaccination against "hidden" tumor cells was developed. Therefore, the method disclosed by WO 2011/078676 does not provide any information in how pulsed radiofrequency applied in a non-invasive manner could provide a memory and systemic immune response against cancer cells and could be used as a vaccination therapy.

Immune System and Cancer

The immune system is a complex structure and its processes protect the organism against irregularities and diseases. It has two basic subsystems, the innate immune system and the adaptive one. The innate immune system is found in almost all the living objects, develops no immune-memory and the action (response) is non-specific and immediate. The main cellular structures of innate immune system are the macrophages (able to phagocytize), mast cells (releasing inflammatory promoters); granulocytes (a group of three cell-types responding to inflammation), dendritic cells (adaptive immune-cells, presenting antigens), natural killer cells (destroy cells infected with pathogens). The adaptive system found in gnathostomatas (vertebrates with jaw) has an immunological memory and usually a lag-time for response. The main groups of cells belonging to the adaptive system are B-cells, which are producing antibodies to neutralize invaders, and T-cells specialized in destroying the infected cells or coordinating the immune-response.

One of the roles of the immune system is to identify and destroy tumors. The recognition is possible due to tumor specific antigens or tumor associated antigens on the surface of tumor cells but not present on healthy cells. Any protein produced in a tumor cell that has an altered structure due to genetic mutation can act as a tumor antigen. Alternatively, proteins that are normally produced in very low quantities but whose production is increased in tumor cells may sometimes trigger an immune response. One example of such a protein is the enzyme tyrosinase. Since these proteins are endogenous proteins, an immune response is rarely but if the antigen density on the cell membrane is sufficiently high, the cancer cells can be recognized and destroyed by specific T-cells.

Another important class of tumor antigens are proteins normally produced only in the early stages of embryonic development before the immune system is fully developed so that a self-tolerance against these proteins or antigens cannot develop. Furthermore, cells infected by oncoviruses, e.g. EBV and HPV, contain viral DNA, which is transcribed and the resulting protein or the DNA as such may cause an immune response.

Specific immune response to tumor cells uses T-cells. Tumor cells often express a reduced number of recognizable structures or even hide the recognizable structures, which could be recognized by APCs. Some tumors inhibit the immune-response, for example by secreting TGF-β. Additionally, immunological tolerance can be developed and no further immune-reaction is directed against the cancer cells. Tumor can make paradoxes also, like macrophages promoting tumor growth in some cases.

A basic theoretical formulation proposes a cancer immuno-surveillance, blocking the carcinogenesis and keeping in force the cellular homeostasis. The process by which an individual is protected against cancer growth by its own immune system is called immuno-editing. Inflammation could be one of the major promoters of tumor-development in elderly subjects.

Present cancer therapies are dominantly focused on the so called "gold standards", such as chemotherapies (pharmaceutical products), radiotherapy (ionizing beams), surgery and their combinations. New methods for cancer treatment are emerging, among them the immune-therapy being a promising one.

In chemo-thermo-therapies (whole body hyperthermia in combination with chemotherapy) the role of chaperone proteins is important. Chaperones (like stress- or heat-shock-proteins) are highly conserved proteins, which are present in almost every living cell and assist the non-covalent folding or unfolding and the assembly or disassembly of other macromolecular structures. Chaperones are found in virtually all living organisms, regardless their stage in the evolution. Chaperones are ubiquitously expressed under normal and patho-physiological conditions but any kind of change in the dynamic equilibrium of the cell life (environmental stresses, like heat, various pathogen processes, diseases, etc.) regulates, mostly activates, their synthesis. Excretion of chaperones is a 'stress-answer' of the cells to accommodate themselves to the new challenges. As a consequence of the up regulated cell growth and thus increased protein expression of malignant cells, molecular chaperones are highly expressed in cancerous cells and are essential to the survival of these cell types. Heat shock proteins (HSP) are a group of chaperones having an increased expression when cells are exposed to elevated temperatures or other stress. Furthermore, induction of various HSPs (HSP27, HSP70, and HSP90) was observed in numerous metastases and the HSP90 homologue, GRP94 may act as a mediator of metastasis generation. Moreover, stress- and heat-shock-proteins are induced by every oncological treatment-method meant to eliminate the malignancy. Thus, intensive chaperone synthesis was detected after conventional hyperthermia, chemotherapy, radiotherapy or even photodynamic-therapy. On the way of the stress adaptation, induction or overexpression of stress proteins provides generally effective protection of the cell against apoptosis. However, extracellular expression of stress proteins acts oppositely and signals to the immune system also a defect of the actual cell. Moreover, heat treatment can also lead to a multi-drug resistance.

Non-temperature dependent effects (mainly electromagnetic field stresses) could also produce chaperone-synthesis. The HSP manifestation in the biopsies of cancer tissues could give a good clinical indication for a treatment response.

On the other hand, the chaperone HSP70 assists to freeze the actual dynamic equilibrium (the "status-quo") and so try to re-establish the cellular communication in the extracellular electrolyte. It is known that chaperone HSP70 expression on the cell-membrane gains apoptotic signals and enhances the immune reactions. HSP70 participates in the activation of the p53 tumor-suppressor and has been associated with the tumor-suppressor retinoblastoma protein.

Membrane re-localization of HSP70 promotes apoptosis, and has a very important role (more than other chaperones) in the membrane "fluid" to keep it functional. Tumor-specific membrane localization of HSP70 mainly in the cholesterol-rich micro-domains of the membrane results in efficient activation of NK-cells in immune response. A broad band (0.2-20 MHz) electromagnetic field increased the HSP70 expression. Production of the same increase of HSP70 expression by temperature would require a 14 orders of magnitude greater perturbation, which outlines the great advantage of the non-temperature dependent effect of electric fields over the temperature-dependent ones in regard to HSP70 expression. The role of extracellular HSP70 is a topic of increasing interest in the overall immune reactions of bio-systems.

Cellular lyses and the liberation of toxins characteristic to cell necrosis could of course cause limits of the distortion process. However, the apoptotic cell-death or any other systemic immune-action would be more natural and free the system from toxic complications. The thermally induced apoptosis and the activation of natural killer cells are both suitable to solve this task.

Thus, it would be highly useful in cancer treatment to provide a possibility to support the immune system to easily recognize tumor cells and especially non-immunogenic tumor cells expressing a reduced number of recognizable structures or hiding the structures, which could be recognized by APCs. Such a possibility would also allow treating successfully metastases and patients, who developed metastases, which are normally incurable.

BRIEF SUMMARY OF THE INVENTION

The objective of the present invention is to provide the afore-mentioned possibility.

This objective is solved by the teaching of the independent claims. Further advantageous features and embodiments are evident from the description, the examples and the dependent claims.

The present invention relates to a vaccine composed of at least one immune stimulant and radiofrequency waves using capacitive coupling and to a method, especially an in-situ and in vivo vaccination method for treatment of primary cancer and its metastases even in disseminated cell-states, which cannot be detected by presently available imaging methods or for prevention of relapse of the cancer disease and especially for enabling and supporting the patient's own immune system to recognize and kill the cancer cells and to build up a memory to prevent relapse of a cancer disease.

The present invention uses the patient's own, unique tumor specific antigens. However, these antigens are not recognizable—they are hidden—for the immune cells and consequent reactions. This prevents the malignancy against the immune attack, and the body recognizes the tumor as its own tissue-reparation. The immune system is silenced against tumor cells. The present invention provides a vaccine, able to free the tumor antigens that they are recognized by the antigen presenting cells (APCs) to start specific immune reaction against the malignancy. It is a special effect provided by the inventive vaccine, namely exposing the hidden antigens, promoting the recognition by APCs (especially dendritic cells) and, preparing said APCs and the entire immune system to build up a specific immune reaction to eradicate the tumor. Hence, the vaccine of the present invention generates a natural process.

Briefly, the immunogenic cell-death caused by the vaccine of the present invention causes activation of the adaptive immune system to fight against the cancer cells. The immune stimulant, as a component of the inventive vaccine, supports this fight so that the effect is completely systemic having long-term memory.

DETAILED DESCRIPTION OF THE INVENTION

Definitions

Figure 1:
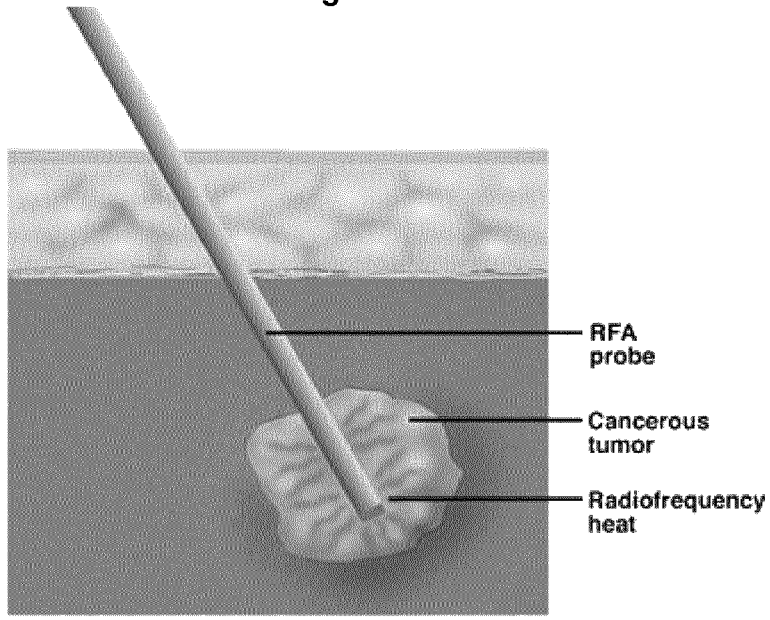
FIG. 1 (prior art) illustrate treatment of cancer using RFA.

The term "hidden tumor cells" or "non-immunogenic tumor" as used herein encompasses tumor and tumor cells that escape the immune system detection by decreasing the expression or not expressing tumor specific antigens (TSA) on their surface. The hidden tumor cells comprise the "dormant tumor cells", the disseminated cells and the micrometastases. The dormant tumor cells do not show a malignant character while studied and are chemo-resistant, but not heat resistant. The disseminated cells are circulating in the blood at low concentration. Their low antigen presentation and concentration in the blood make their detection impossible. The micrometastases are generally the most dangerous and invisible parts of the malignant development. The resolution of the currently used imaging systems allows the detection of micrometastases only after they form aggregates composed of few millions of cells.

The term "in vivo-vaccination" as used in the application means that the antigens necessary for immunization are generated in the patient's body. Most of the tumor-vaccinations are using artificially produced antigens or the patient's own antigens prepared using in vitro laboratory conditions and reinjected to the patient. However, in the present invention, the appropriate antigens necessary for immunization are generated in vivo i.e. by the patient's body. Thus, the vaccination method of the present invention can also be called in vivo vaccination method.

The term "in-situ vaccination" as used herein means that the immunization, i.e. the recognition of the specific TSA, is processed actually in the tumor. In most of the "classical" tumor-vaccinations, the antigens are placed in the body far away from the place of the expected active molecular actions. However, according to the present invention, the immunization process is carried out in-situ i.e. at the site of the tumor. Thus, the vaccination method of the present invention can also be called in-situ vaccination method.

As used herein, the term "moderate whole-body hyperthermia" refers to the whole body heating at a temperature of 38° C. to 39° C. It is also known for the person skilled in the art as a "fever range whole-body heating" and is generally used for boosting the immune system. Three types of whole-body hyperthermia can be differentiated:

Mild whole-body hyperthermia refers to the whole-body heating at a temperature of about 38° C.;
Moderate whole-body hyperthermia as defined above;
Extreme whole-body hyperthermia refers to the whole-body heating at a temperature of 40° C. to 41° C., which can sometimes extend up to 42° C.

As used herein, the term "people with increased risk of cancer" refers to people who are born with a markedly increased susceptibility to cancer, as a result of inheritance of genetic mutations. A genetic mutation may be sufficient to greatly increase the susceptibility of a person to one or more types of cancer, and this susceptibility can be passed from generation to generation. The inheritance of such mutations results in families in which a number of individuals develop a certain type(s) of cancer. Known genes associated with hereditary cancer include the aberrant BRCA1 and BRCA2 genes that increase breast cancer risk and the HNPCC gene that is linked with colon cancer. Furthermore the term "people with increased risk of cancer" refers also to people who developed or most probably developed some mutations by exposure to environmental carcinogens having therefore an increased risk for cancer. Exposure to risk factors for cancer may include prolonged or repeated exposure to radiation, tobacco use, exposure to cancer-causing chemicals and infection with a cancer virus, like human papillomavirus (HPV). Chemicals and radiation that are capable of triggering the development of cancer are called "carcinogens." Carcinogens act by initiating a series of genetic alterations ("mutations") and stimulating cells to proliferate. There can be a delay of several decades between exposure to a carcinogen and the onset of cancer. This period between exposure and onset of disease is the lag time. Therefore it is one aspect of the present application to treat people with increased risk of cancer caused by exposure to carcinogens at or around the end of the lag time. Thus, for this category of people a vaccination according to the present invention is particularly important.

The present invention relates to a method for non-invasive treatment of primary cancer and its metastases in a patient that has cancer or for prevention of relapse of a cancer disease in a patient that was successfully treated by administering to the patient an immune stimulant together with radiofrequency waves using capacitive coupling in a condenser arrangement.

Thus, a patient with primary cancer and/or with metastases or a patient after a successful cancer treatment having the risk of a relapse is treated locally or systemically with an immune stimulant and in addition receives a hyperthermia treatment with radiofrequency waves using capacitive coupling in a condenser arrangement. The hyperthermia treatment with radiofrequency waves using capacitive coupling in a condenser arrangement may be administered once a day or each second day or once a week or is administered as needed or as scheduled by a medical practitioner and takes normally one to several hours per session.

As used herein, the term "capacitive coupling" refers to the fact that the electromagnetic energy is delivered to the load using electric field dominance constructing the arrangement like a capacitor. The load, in this case the patient to be treated, is a part of the capacitor and acts as lousy dielectric material of the capacitor. The electrodes are matched by their impedance. The method used in the present invention has "conductive" capacitive coupling, domination the conduction part of the dielectric function in the imperfect dielectric material, production Joule-heat in majority. When the electrodes are loosely connected, the coupling became more and more radiative, thereby losing its Joule-heat capacity.

The combination of the immune stimulant and the hyperthermia treatment with radiofrequency waves using capacitive coupling according to the present invention enables the patient's own immune system to recognize the primary cancer cells and the metastases and the metastasized cancer cells and the single cancer cells formed during relapse and after this recognition to kill these cancer cells effectively. Thus, a preferred embodiment of present invention refers to an in-situ and in vivo vaccination method of a patient, who suffers from cancer or was successfully treated of cancer with or without the method according to the present invention or of people with increased risk of cancer.

In the present method of treatment of cancer and metastases or prevention of relapse of the cancer, the radiofrequency waves are administered using capacitive coupling in a condenser arrangement comprising at least one electrode and a counter-electrode, wherein the patient is the dielectric material in between.

One of the advantages of the present method of non-invasive treatment and prevention of cancer is that the administration of radiofrequency waves does not require the use of antennas like in the RF arrangement with radiative coupling. Another significant advantage of the present method in respect to prior art is that the administered radiofrequency waves do not increase the body temperature of the patient or the temperature of the treated area.

In a preferred embodiment of the present invention, the method of treatment and prevention of relapse of cancer involves the systemic administration of the radiofrequency waves using capacitive coupling in a condenser arrangement.

Within the above method the immune stimulant is preferably selected from the group comprising or consisting of bacterial preparations, lipopolysaccharides, extract of *Bacillus* Calmette-Guérin, Picibanil, Ancer, Xiao-Aiping, Leukine® (sargramostim; recombinant granulocyte macrophage colony-stimulating factor), killed *Corynebacterium parvum* bacteria and its extract, cytokines, moderate whole-body hyperthermia, TLR receptor agonist agents, any natural or synthetic agent acting the TLR pathway, ipilimumab, herbal compounds (*echinacea* etc.), and Levamisol.

The present method is especially useful for vaccination of people with increased risk to develop cancer, because this method generates a memory of the immune system to recognize cancer cells and especially the cancer cells trying to escape the immune system by hiding the tumor specific antigens.

Moreover, the present method is extremely useful for vaccination of patients, who were putatively successfully treated of a cancer disease as it is known that there is a high probability of a relapse of the cancer. Thereby the term "relapse" refers to the return of a cancer disease or the signs and symptoms of a cancer disease after a period of improvement in which no cancer could be detected. The likely relapse occurs is that a few of the original cancer cells survived the initial treatment. Sometimes, this is because cancer cells spread to other parts of the body and were too small to be detected during the follow-up taking place immediately after treatment (micrometastases). The inventive method could provide a memory and systemic immune response against cancer cells, especially also against spread cells and could be used as a vaccination therapy. Thus, the above method is particularly useful to prevent relapse after putatively successful treatment of a cancer treatment with or without the method according to the present invention.

The invention according to the present invention is suitable for treatment of primary cancer and its metastases and for prevention of relapse of a cancer, wherein the cancer, primary cancer, the metastases or the cancer cells are selected from the group consisting of: adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, non-small cell lung cancer (NSCLC), breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, squamous cell carcinoma of the head and neck (SCCHN), prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer. Particularly suitable for treatment are, for example, astrocytomas, glioblastomas, pancreatic cancer, bronchial cancer, breast cancer, colorectal cancer, ovarian cancer, gastric cancer, laryngeal cancer, malignant melanoma, oesophageal cancer, cervical cancer, liver cancer, bladder cancer, and renal cell cancer. The invention according to the present application is especially suitable for treatment of non-immunogenic tumors or cancer.

A preferred embodiment according to the present method refers to a method for non-invasive treatment of primary cancer and its metastases in a patient that has cancer or for prevention of relapse of a cancer disease in a patient that was successfully treated by administering to the patient Xiao-Aiping with radiofrequency waves using capacitive coupling in a condenser arrangement.

Another aspect of the present invention relates to a vaccine composed of at least one immune stimulant and radiofrequency waves using capacitive coupling in a condenser arrangement for treatment of primary cancer and its metastases in a patient who has a cancer or for prevention of relapse of the cancer disease in a person who was successfully treated of a cancer disease or for prevention of cancer in a person having increased risk for development of cancer.

Thus, the present invention refers to the use of an immune stimulant for the preparation of a medicament for the treatment of cancer and its metastases, wherein the immune stimulant is administered in conjunction with radiofrequency waves using capacitive coupling in a condenser arrangement. Furthermore, the present invention refers to the use of an immune stimulant for the preparation of a medicament for the treatment of a mammal having cancer or for prevention of relapse of a cancer disease in a mammal, who was putatively successfully treated of a cancer disease, wherein the immune stimulant is administered in conjunction with radiofrequency waves using capacitive coupling in a condenser arrangement. Thereby the immune stimulant activates numerous non-specific immune reactions and converts the local effect of the radiofrequency waves using capacitive coupling into systemic effect.

In an another aspect, the present invention refers to the use of an immune stimulant for the preparation of a vaccine for the treatment of primary cancer and its metastases in a patient, who has cancer or for prevention of relapse of the cancer disease in a patient, who was successfully treated of a cancer disease, wherein the immune stimulant is administered to the patient in conjunction with radiofrequency waves using capacitive coupling in a condenser arrangement. This vaccine is especially useful for in-situ vaccination and preferably for the cancer types mentioned above.

The immune stimulant of the vaccine is preferably selected from the group comprising or consisting of bacterial preparations, lipopolysaccharides, extract of *Bacillus Calmette-Guérin*, Picibanil, Ancer, Xiao-Aiping, Leukine® (sargramostim; recombinant granulocyte macrophage colony-stimulating factor), killed *Corynebacterium parvum* bacteria and its extract, cytokines, moderate whole-body hyperthermia, TLR receptor agonist agents, any natural or synthetic agent acting the TLR pathway, Ipilimumab, herbal compounds (*echinacea* etc.), and Levamisol.

Preferably, the vaccine according to the present invention is a vaccine composed of at least Xiao-Aiping and radiofrequency waves using capacitive coupling in a condenser arrangement for treatment of primary cancer and its metastases in a patient who has a cancer or for prevention of relapse of the cancer disease in a person who was successfully treated of a cancer disease or for prevention of cancer in a person having increased risk for development of cancer.

Another aspect of the present invention refers to an immune stimulant for non-invasive treatment of primary cancer and its metastases or for prevention of relapse of the cancer disease when used in association with radiofrequency waves using capacitive coupling in a condenser arrangement. Thus, the present invention refers an immune stimulant for non-invasive treatment of primary cancer and its metastases or for prevention of relapse of the cancer disease, wherein the immune stimulant is administered in conjunction with radiofrequency waves using capacitive coupling in a condenser arrangement. Furthermore, the present invention refers to immune stimulant for the treatment of a mammal having cancer or for prevention of relapse of a cancer disease in a mammal, who was putatively successfully treated of a cancer disease, wherein the immune stimulant is administered in conjunction with radiofrequency waves using capacitive coupling in a condenser arrangement. Thereby the immune stimulant activates numerous non-specific immune reactions and converts the local effect of the radiofrequency waves using capacitive coupling into systemic effect.

A further aspect of the present invention refers to Xiao-Aiping for non-invasive treatment of primary cancer and its metastases or for prevention of relapse of the cancer disease, when used in association with radiofrequency waves using capacitive coupling in a condenser arrangement. Thus, a preferred embodiment of the present invention refers Xiao-Aiping for non-invasive treatment of primary cancer and its metastases or for prevention of relapse of the cancer disease, wherein the Xiao-Aiping is administered in conjunction with radiofrequency waves using capacitive coupling in a condenser arrangement. Moreover, the present invention refers to Xiao-Aiping for the treatment of a mammal having cancer or for prevention of relapse of a cancer disease in a mammal, who was putatively successfully treated of a cancer disease, wherein the immune stimulant is administered in conjunction with radiofrequency waves using capacitive coupling in a condenser arrangement.

Surprisingly it was found that common immune stimulants are highly useful for treatment of primary cancer and its metastases or for prevention of relapse of the cancer disease when used in association with radiofrequency waves using capacitive coupling in a condenser arrangement. The inventors could show that radiofrequency waves using capacitive coupling in a condenser arrangement alone did not have any effect on far-away situated tumor or metastases. Immune stimulant (LPS, Xiao-Aiping) administration did not either have an effect on tumor regression. However, immune stimulant administration in conjunction with radiofrequency waves using capacitive coupling provides an abscopal effect and results in the shrinkage of far-away situated tumors. Thus, radiofrequency waves using capacitive coupling and immune stimulant administration in association resulted in systemic effects.

The present invention would not work with radiative coupling, because radiative coupling would burn the cells. Thus, no antennas like in RF arrangement with radiative coupling are used for administering the radiofrequency waves in association with the immune stimulant according to the present invention. The radiofrequency waves according to the present invention are administered using a condenser arrangement comprising at least one electrode and at least a counter electrode, wherein the patient is the dielectric material in between.

A preferred embodiment of the present invention refers to an immune stimulant used in association with radiofrequency waves systemically administered.

The radiofrequency waves using capacitive coupling in a condenser arrangement according to the present invention do not increase the body temperature of the patient or the temperature of the treated area.

All common immune stimulants can be used in the present invention. Immunostimulants, or immunostimulators, are substances that stimulate the immune system by inducing activation or increasing activity of any of its components. Within the present invention non-specific immunostimulants which act irrespective of antigenic specificity to augment immune response of other antigen or stimulate components of the immune system without antigenic specificity, are preferred. Examples of possible immune stimulants useful within the present invention are lipopolysaccharides, extract of *Bacillus* Calmette-Guérin, Picibanil, Ancer, Xiao-Aiping, Leukine® (sargramostim; recombinant granulocyte macrophage colony-stimulating factor), killed *Corynebacterium parvum* bacteria and its extract, moderate whole-body hyperthermia, Ipilimumab (an antibody against cytotoxic T-lymphocyte-associated antigen 4), Levamisol, KLH (Keyhole Limpet Hemocyanin), low-dose cisplatin or carboplatin (<0.4 mg/kg), Juzentaihoto (JT48) and deoxycholic acid (DCA). The immune stimulant according to the present invention may be selected from the group comprising or consisting of bacterial preparations, biological response modifiers, TLR receptor agonist agents, natural or synthetic agent acting the TLR pathway, herbs and herbal extracts, Traditional Chinese medicine (TCM), Kampo (Japanese adaptation of Chinese medicine), like Juzentaihoto (JT48). Particularly preferred immune stimulants are Xiao-Aiping, Leukine®.

Figure 48:
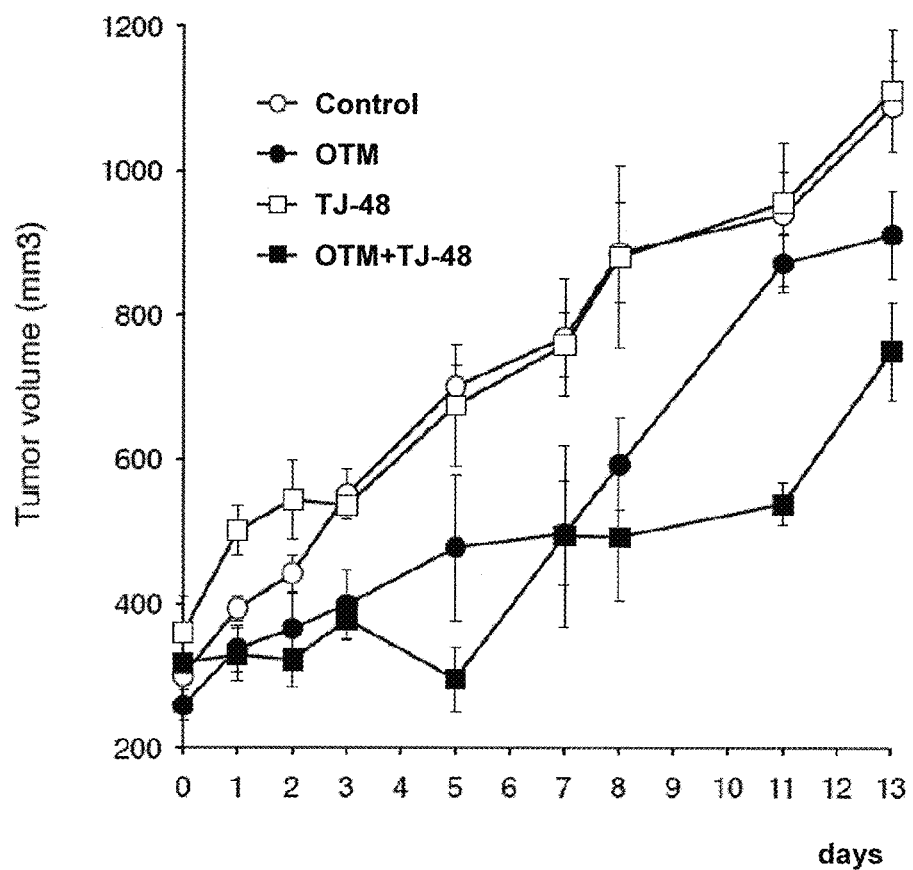
FIG. 48 shows the beneficial effect on the reduction of the tumor volume in orthotopic 4T1 tumor model provided by the vaccine.

In Example 14 the immune stimulant JT48 was used and the result is shown in FIG. 48. Administration of the immune stimulant alone (TJ-48) without administration of radiofrequency waves using capacitive coupling in a condenser arrangement has almost no effect, while the RF treatment (OTM: oncothermia treatment) alone has a considerable effect but both together, i.e. immune stimulant with oncothermia has a remarkably effect. Same results could be obtained by using any other of the herein disclosed immune stimulants such as the immune stimulants of the previous paragraph.

Bacterial preparations are preferably selected from the group comprising or consisting of lipopolysaccharides, extract of *Bacillus* Calmette-Guérin, Picibanil (OK-432), killed *Corynebacterium parvum* bacteria and its extract.

Biological response modifiers, (Biologicals; BRMs), are substances that the human body produces naturally, but which may be produced identical or very similar by biotechnology methods and other technologies, too. These substances arouse the body's response to an infection. Biologicals are preferably selected from the group comprising or consisting of monoclonal antibodies, Interleukin-2, Interferon, various types of colony-stimulating factors (CSF, GM-CSF, G-CSF), human TNF receptor, substance produced by the body's thymus like thymic protein A or thymic humoral factor (THF), and Ipilimumab (an antibody against cytotoxic T-lymphocyte-associated antigen 4).

Herbs and herbal extracts are preferably selected from the group comprising or consisting of *Echinacea angustifolia* (Purple coneflower), *Ginseng* root, Xiao-Aiping (extract from Marsdenia tenacissima), Juzentaihoto (JT48) and Chinese *astragalus* root.

Changes to sex hormone levels in the body cause particular symptoms. These vary from person to person. The symptoms may be mild but for some people can be severe and need treatment. Some cancers (breast, prostate) are hormone sensitive and need estrogen or testosterone to grow. Therefore it is preferred that the immune stimulant according to the present invention is no hormone and further preferred no sexual hormone.

The inventive immune stimulant described herein activates the immune system of the patient and in association with the administered radiofrequency waves using capacitive coupling in a condenser arrangement provides a vaccine-effect against the cancer diseases by building up a memory to recognize and kill the cancer cells and thus, to prevent relapse of the cancer disease.

As used herein, the term "vaccine-effect" refers to the immune response developed by the patient following the administration of the immune stimulant in association with radiofrequency waves using capacitive coupling in a condenser arrangement, immune response enabling the recognition of antigens of the cancer cells and the activation of the defense mechanisms for complete eradication of the cancer cells.

Another aspect of the present invention relates to a non-invasive method for treatment of primary cancer and its metastases in a patient having cancer or for prevention of relapse of a cancer disease in a patient that was successfully treated of cancer by administering to the patient an immune stimulant together with radiofrequency waves using capacitive coupling in a condenser arrangement.

As used herein, the term "successfully treated of cancer" refers to patients in a period after initial cancer treatment having an improvement and in which no cancer could be detected anymore. These patients have an increased risk for a return of a cancer disease. Thus they are potentially successfully treated of cancer as it is possible that a few of the original cancer cells survived the initial treatment, for example by spreading to other parts of the body and being too small to be detected by the current diagnosis methods. Mammals being completely cured having no cancer cell or malignant cell are not able to develop the vaccination effect of the present invention since no tumor specific or tumor associated antigens can be detected and attacked by the immune system Nevertheless, the risk for relapse is so high that currently radiation is applied to many patients after common anti-cancer treatment, even after a successful surgery, to prevent relapse. One advantage of the present method is a reduction in side effects treating persons only susceptible to cancer and the systemic effect of the inventive treatment so that spread cells can be treated also as it is not known where in the patient's body these are located. Thus the methods according to the present invention are suitable for patients having a risk of incomplete clearance of cancer cells after initial cancer treatment.

A patient suffering from primary cancer and/or metastases or a patient after a successful cancer treatment having the risk of developing a relapse or having developed a relapse is treated locally or systemically with an immune stimulant and in addition is subjected to a hyperthermia treatment with radiofrequency waves using capacitive coupling in a condenser arrangement. The hyperthermia treatment with radiofrequency waves using capacitive coupling in a condenser arrangement is administered as needed, for instance, once a day or each second day or once a week or as scheduled by a medical practitioner. The hyperthermia treatment with radiofrequency waves using capacitive coupling takes normally one to several hours per session. The immune stimulant is also administered as needed. The immune stimulant for non-invasive treatment of primary cancer and its metastases or for prevention of relapse of the cancer disease may be applied in parallel or sequentially with the radiofrequency waves using capacitive coupling in a condenser arrangement. Thereby in parallel means that the immune stimulant and the radiofrequency waves using capacitive coupling in a condenser arrangement are applied to the patient at the same day (within 12 hours) but refers also to an administration scheme wherein administration of the immune stimulant and application of the radiofrequency waves are done alternating (interval between 12 and 48 hours). A sequential application refers to an application wherein the immune stimulant is administered before or subsequently after the radiofrequency waves but preferably before the hyperthermia treatment.

In a preferred embodiment of the present invention, the radiofrequency waves using capacitive coupling in a condenser arrangement are administered first and after this first period administering only the radiofrequency waves using capacitive coupling in a condenser arrangement an immune stimulant is administered additionally. For example 48 h after first administration of radiofrequency waves using capacitive coupling in a condenser arrangement, or more preferably 72 h post administration, the immune stimulant is administered for the first time. Thereafter there is a parallel administration of both immune stimulant and radiofrequency waves. Therefore the present invention refers to an immune stimulant for non-invasive treatment of primary cancer and its metastases or for prevention of relapse of the cancer disease when used in association with radiofrequency waves using capacitive coupling in a condenser arrangement wherein in a first interval the radiofrequency waves are administered only and in a subsequent interval the immune stimulant is administered simultaneously with the radiofrequency waves. The administration of the immune stimulant as well as of the radiofrequency waves using capacitive coupling in a condenser arrangement can be daily, every two days or every three days repeated during a therapy. The duration of the complete therapy depends on different parameters such as the situation of the patient (short for prevention of relapse but perhaps longer or repeatedly for patients having an increased risk because of relevant mutations), the kind of cancer or the size of the primary cancer.

The use of hyperthermia in cancer treatment is well known in the state of the art. However, the activation of the adaptive immune system of the patient in a way that highly personalized in situ vaccination occurs, was never reported in the state of the art literature.

Thus, a preferred embodiment of present invention refers to an in-situ and in vivo vaccination method of a patient, who has a cancer or was successfully treated of cancer with or without the method according to the present invention or of people with increased risk of cancer.

In the present method of treatment of cancer and metastases or prevention of relapse of the cancer, the radiofrequency waves are administered using capacitive coupling in a condenser arrangement comprising at least one electrode and a counter-electrode, wherein the patient is the dielectric material in between.

One of the advantages of the present method of non-invasive treatment and prevention of cancer is that the administration of radiofrequency waves does not require the use of antennas like in the RF arrangement with radiative coupling. Another significant advantage of the present method in respect to prior art is that the administered radiofrequency waves do not increase the body temperature of the patient or the temperature of the treated area.

In a preferred embodiment of the present invention, the method of treatment and prevention of relapse of cancer involves the systemic administration of the radiofrequency waves using capacitive coupling in a condenser arrangement.

Moreover, the present invention also relates to a vaccine composed of at least one immune stimulant and radiofrequency waves in capacitive coupling in a condenser arrangement for treatment of primary cancer and its metastases or for prevention of relapse of the cancer disease. The combination of at least one immune stimulant and radiofrequency waves using capacitive coupling is useful for treatment of primary cancer and its metastases or for prevention of relapse of the cancer disease.

Thus the present invention also relates to the use of at least one immune stimulant to achieve a vaccination against cancer cells in a patient in case the at least one immune stimulant is administered in combination with radiofrequency waves applying capacitive coupling in a condenser arrangement. The present invention also relates to the use of at least one immune stimulant to achieve a vaccination against cancer cells in a patient in case the at least one immune stimulant is used in combination with radiofrequency waves applying capacitive coupling in a condenser arrangement. The present invention also relates at least one immune stimulant used or useful to achieve a vaccination against cancer cells in a patient in case the at least one immune stimulant is used in combination with radiofrequency waves applying capacitive coupling in a condenser arrangement.

Thus, the present invention refers to the use of an immune stimulant for the preparation of a vaccine for the treatment of primary cancer and its metastases in a patient, who has cancer or for prevention of relapse of the cancer disease in a patient, who was successfully treated of a cancer disease, wherein the immune stimulant is administered to the patient in conjunction with radiofrequency waves using capacitive coupling in a condenser arrangement. This vaccine is especially useful for in-situ vaccination and preferably for the above mentioned cancer types. The vaccine according to the present invention is particular useful for vaccination of people with increased risk to develop cancer and/or for vaccination of a patient to prevent relapse of the successfully treated cancer disease.

Another aspect of the present invention refers to the use of Xiao-Aiping for the preparation of a vaccine for the treatment of primary cancer and its metastases in a patient, who has cancer or for prevention of relapse of the cancer disease in a patient, who was successfully treated of a cancer disease, wherein the immune stimulant is administered to the patient in conjunction with radiofrequency waves using capacitive coupling in a condenser arrangement.

It is important to mention that within any inventive use or method disclosed herein, the application and/or administration of the radiofrequency waves does not involve an invasive step. The radiofrequency waves are applied from outside the body without the need to insert or implant electrodes or antenna arrangements into the body of the patient or into the blood stream or into the tissue. Moreover, no radiative coupling is used and preferably no direct application or generation of heat is used or involved (cf. FIG. 1). The wavelength used within the present invention is between 10 kHz and 50 MHz, more preferably between 130 kHz and 42 MHz and most preferably the values 135.6 kHz±5%, 339 kHz±5%, 678 kHz±5%, 1,356 MHz±5%, 3.39 MHz±5%, 6.78 MHz±5%, 13.56 MHz±5%, 27.12 MHz±5%, and 40.68 MHz±5%.

Moreover the present invention does not apply phase array adjustment as done by the radiative coupling with the antenna arrangement. The radiofrequency waves are formed in a condenser arrangement between the electrodes, i.e. at least one electrode and at least one counter-electrode, wherein the body of the patient is the dielectricum (i.e. the dielectric material).

In addition, the present invention relates to a method for vaccination of a patient by administration of a vaccine composed of at least one immune stimulant and radiofrequency waves using capacitive coupling. Such vaccination enables the immune system of the patient to recognize so far unrecognized cancer cells, and furthermore to generate a memory in the patients' immune system to recognize also cancer cells in other parts of the body, especially during metastases formation and also to recognize new cancer cells, which relapse after a successful cancer treatment of the patient. This multidisciplinary method is able to cause an in-situ and in vivo personalized tumor vaccination and to enable the immune system, and especially the adaptive immune system to recognize and eliminate cancer cells and especially single cancer cells before a cancer disease occurs and to eradicate metastases and to recognize and eliminate new cancer cells, which relapse after successful cancer treatment. Thus, the present invention enables the immune system to recognize cancer cells and metastases previously non-recognized and therefore to kill the cancer cells, finally leading to successful treatment of primary cancer and its metastases and prevention of relapse of a malignant metastatic disease.

The mode of action of the vaccine of the present invention could probably be explained as outlined in the following. The vaccine of the present invention stimulates the immune system in a specific manner in comparison with the immune stimulant alone. The malignant lesion is not attacked by the innate immune system, and the adapted immune system is not able to recognize the tumor, so remains also inactive. This is the reason, why simple immune stimulation cannot be effective to destroy the developed malignancy. Radiofrequency waves using capacitive coupling in a condenser arrangement (oncothermia) alone stimulates the immune system when applied systemically, so faces the same non-specificity as the immune stimulants. Locally applied oncothermia causes apoptosis or local effects, but the mean malignant forces the dissemination of the cells and the metastatic formation is out of the scope of this treatment. The vaccine or combination of the present invention composed of at least one immune stimulant and radiofrequency waves using capacitive coupling attacks the malignant cells in the whole body.

Thus, the vaccine of the present invention is also highly useful for treatment of primary cancer and its metastases and for prevention of relapse of the cancer disease in patients with weak immune system or with suppressed immune system, because the inventive vaccine triggers the immune response and activates the immune system.

In the following a summary of the status of current tumor immunotherapy possibilities, especially antitumor vaccination methods are given. Table 1 summarizes some clinical trials showing the present antitumor vaccination possibilities (M. Vergati, C. Intrivici, N.-Y. Huen, J. Schlom, K. Y. Tsang, Strategies for Cancer Vaccine Development; *J. Biomed. Biotech.* 2010, Article ID 596432, doi: 10.1155/2010/596432).

TABLE 1

Clinical studies with tumor-vaccination (Abbreviations: OS = overall survival; RR = response rate; PFS = progression free-survival; BSC = best supportive care; DFS = disease free survival).

| VACCINE | PHASE | TUMOR | No. of Patients | NOTE |
|---|---|---|---|---|
| Vaccines with viral vectors | | | | |
| PSA-TRICOM | II | Prostate | 122 | 8.5 m OS, improvement vs. placebo |
| | II | Prostate | 32 | >16.4 m OS, improvement in HPS >18 m group |
| PANVAC-VF | III | Pancreas | 255 | Failed >OS Pts. with life expectancy <3 m |
| Vaccines with peptides | | | | |
| Provenge | III | Prostate | 512 | 4.1 m OS improvement vs. placebo |
| Oncophage | III | Melanoma | 322 | Prolonged OS in M1a and M1b subpopulation |
| | III | Renal | 818 | No differences in DFS and OS |
| gp100:209-217(210M) | III | Melanoma | 185 | Significant improvement in RR and PES |
| Stimuvax | IIB | Lung | 171 | 17.3 m OS, improvement vs. BSC in locoregional stage IIB |
| Vaccines with tumor cell or tumor-cell lysate | | | | |
| OncoVAX | III | Colon | 254 | Significant improvement in DFS and OS in stage II |
| Reniale | III | Renal | 558 | Significant improvement in DFS and OS |
| GVAX | III | Prostate | 626 | Failed to improve OS vs. docetaxel |
| | III | Prostate | 408 | Failed. Higher death-rate in combination arm (vaccine + docetaxel) vs. docetaxel alone |
| Vaccines with RNA | | | | |
| mRNA from Pca cell-lines | I/II | Prostate | 19 | Immunological responses |

Multiple cancer vaccinations such as these listed by Table 1, the very complicated off-situ method, or the robotic DC-culturing have been developed. However, the above mentioned cancer vaccines can be applied only in very limited conditions. The main reason of the failures and low efficacy of the prior art cancer vaccines is the low immunogenic activity of the tumor-cells in general cases. The immune-system is not able to recognize or identify the tumor-cells, and therefore cannot eliminate them. Immune-stimulation without specific immune-identification processes (e.g. cytokine therapies with IL-2, IL-8, TNF, etc.) cannot reach the desired efficacy. In this context, the cancer vaccination according to the present invention is superior over the known state of the art in cancer vaccinations. The present invention relates to an in-situ and in-vivo vaccination and generates the following beneficial effects:

1. The RF electric field applied within the present invention, and more specifically the amplitude modulated (AM) RR electric field induces immunogenic cell death.

Proofs:
1.1. Apoptotic cell death with apoptotic body formation (see FIG. 14)
1.2. Immunogenic DAMP (damage associated molecular pattern)/SAMP (stress associated molecular pattern) formation:
1.2.1. HSP overexpression and externalization (see FIGS. 3, 18, 28 and 30)
1.2.2. DR5 (TRAIL) overexpression (see FIG. 17)
1.2.3 HMGB1 (high mobility group box) externalization (see FIG. 15)
1.2.4 Calreticulin externalization (see FIG. 16)

2. Immunogenic cell death induced by RF waves using capacitive coupling creates strong local immune reaction against the tumor. The unhidden tumor antigens became recognizable by APCs. Due to RF waves induced immunogenic cell death the patients unique TSA are presented by dentritic cells (DCs) to T-cells creating specific immune reactions against the patient's malignancy.

Proofs:
2.1. Leukocyte invasion ring around the destroyed tumor tissue
2.2. Presence of the T cells in this ring 3. The effect of the immune stimulant, such as bacteria derived immune stimulants (like for example Picibanil, Ancer, C. parvum, Coley-extract, Leukine, other LPS-extracts, etc.), in combination with the locally induced RF waves using capacitive coupling is systemic. Thus, far metastases are destroyed by cytotoxic T-cells, which are activated by TSA loaded DCs.

Proofs:
3.1. LPS study, human abscopal effects, experimental abscopal actions (see FIGS. 4, 5, 6, 29, and 40)

The vaccine, as well as the method of the present invention causes a systemic effect (the adaptive immune system acts in the whole body) and this is one of the most important advantages of the present vaccine, namely to make a local treatment systemic. The systemically acting vaccine of the present invention discovers the hidden tumor antigens, which were presented under the application of the radiofrequency waves using capacitive coupling and treats cancer without causing extreme artificial fever. The inventive vaccine makes this immune support without inducing artificial fever and without any extra load on a weak patient.

Thus, the present invention relates to an immune stimulant useful for the treatment of primary cancer and its metastases even in disseminated cell states, which cannot be detected by state of the art imaging methods and is useful for prevention of relapse of the cancer disease when or under the condition that radiofrequency waves are present and that capacitive coupling in a condenser arrangement are used. The immune stimulant under this condition causes a systemic vaccination activating the immune system and especially the adaptive immune system without causing artificial fever, which is especially useful for the treatment of metastases and primary cancer which cannot be detected by state of the art methods as well as especially useful for the prevention of relapse of a successfully treated cancer.

In addition, the present invention relates to a method for the treatment of primary cancer and its metastases even in disseminated cell states, which cannot be detected by state of the art imaging methods and useful for prevention of relapse of the cancer disease by administration of an immune stimulant to a patient and subjecting the patient to radiofrequency waves using capacitive coupling, while the immune stimulant stimulates the immune system of the patient. Thus, while the immune stimulant is active in the patient's body, the radiofrequency waves using capacitive coupling are applied.

Such an effect cannot be achieved only by methods for immune stimulation. In accordance with the present invention the following administration routes for immune stimulation can be used:
1. Systemic (subcutaneous intramuscular) administration of immuno-stimulant
2. Local (intratumoral) administration of immuno-stimulant (direct local immunostimulation via TLR pathway, cross-presentation, and secondary generated cytokines stimulation)
3. Intratumoral injection
4. Targeted compound delivery to tumor by liposomes (electro-sensitive liposomes)

These immune stimulants of the present invention could be directly injected into the tumor lesion, or applied systemically (orally, i.v. or i.m. injection). When applied systemically they may be directed to the tumor lesion by special tumor targeting methods (such as liposome carrier, magnetic targeting, nanoparticle carriers, etc.). The directed targeting strongly intensifies the cross-priming, when the immune stimulants (e.g. the bacterial endotoxins, like LPSs or LPS-like materials) are acting through the TLR receptor pathways. Said immune stimulants are bonded to the APC cells (e.g. DC) together with the TSAs, inducing therefore stronger and longer effective immune reactions. In case of liposome delivery some immunological adjuvants (like aluminium oxide (alumina), zeolite) could be added.

The systemic effect of the present methods generates strong immune memory against the tumor, preventing the relapse of the cancer disease. Thus, the vaccine of the present invention has a prophylaxis-like effect. For example, colorectal cancer or pancreatic cancer creates metastases in liver in >90%. In these cases, the place of likely-to-be-metastatic could be treated locally, even when the primary tumor is operated out. The inventive vaccine could be applied even if no imaging proof of metastasis exists, but forming of metastasis or relapse is likely. This is important in most of the cases of the primary tumor treatment, even after complete remission. The complete remission as clinical response does not mean complete cure, only means that the present imaging systems cannot see the malignancy at that particular place and particular time.

The inventors found that the radiofrequency waves using capacitive coupling are useful as a physical stimulant, and more precisely are useful for the treatment of primary cancer and its metastases, as well as for prevention of relapse of a cancer disease by inducing a specific defensive immune-response against cancer cells. Especially, the radiofrequency waves using capacitive coupling are useful as a vaccination to eradicate cancer cells, which are normally not recognized by the immune system.

The most important differences between prior art methods and the RF waves using capacitive coupling as used within the present invention are summarized below:

RFA method (state of the art):
uses short wavelength and high frequency alternating current [130 MHz-2400 MHz];
is an invasive method (intratumoral insertion of needles);
only local treatment is possible;
the lesion is burned out/the tumor is burned;
only heat causes the therapeutic effect;
causes vehement necrosis;
uses "antennas" in form of needles;
uses radiative coupling;
requires phase array adjustment for tuning purposes;
the needles are guided by ultrasound or imaging methods such as X-ray screening, CT scan within the patient's body;
is only useful for solid tumors.

The intravascular pulsed radiofrequency stimulation describes by WO 2011/078686 is characterized in that:
it is an invasive method (a needle-like electrode is intravascularly introduced);
it is unspecific blood-treatment method leading to the boost of the immune system by stimulating and attracting the lymphocytes;
it results in direct heating;
it uses a maximal radiofrequency of 1 MHz;
it results in the heating of a macro region;
it does not lead to the induction of apoptotic cell-death.

The inventors found that the RF waves using capacitive coupling and a condenser arrangement (WO 2009/092612, WO 2010/0437372) have the following advantages, which make them suitable for an efficient vaccination method according to the present invention:
RF waves in the range of preferably 10 kHz to 50 MHz of preferably 13.56 MHz, but not more than 50 MHz are used; more preferably from 10 kHz to 45 MHz and most preferably 13.56 MHz or any value obtained by multiplication or division by an integer, preferable division by 40. Thus, the following frequencies are most preferred: 13.56 MHz, or $1/100$, $1/40$, $1/20$, $1/10$, $1/2$ times, 2 times or 3 times, etc. this value of 13.56 MHz (i.e. 6.78 MHz, 27.12 MHz or 40.68 MHz).
it is not an invasive method;
it makes the systemic treatment possible;
it uses heat, which in combination with immune stimulants and the activated patient's own immune system succeeds in fighting against the cancer cells, and thus makes use of an synergistic effect of the heat with the patient's immune system;
it does not cause (undesired) side effects;
it can be used in combination with common cancer therapies such as chemo-therapy and radiation therapy;
it induces tumor-cells apoptosis;
it does not cause tumor cells necrosis;
it uses a condenser arrangement, wherein the patient's body between the electrodes is the dielectric material and is part of the conductive circuit
it uses capacitive coupling;
it does not require support by ultrasound or any imaging method;
it is especially useful for destroying single cancer cells and thus, to treat cancer at the very beginning stage, in its very initial state and also to treat the relapse of a cancer disease at the very beginning stage, in the very initial state;
it induces the ability in the immune system to recognize cancer cells. More specifically, it triggers the adaptive immune system to recognize the cancer cells thus, establishing a long-term memory in the adaptive immune system to recognize the cancer cells, thus providing a vaccination against the cancer cells. This might be the most important difference to all known cancer treatment methods.

Thus, the present vaccination method is particularly useful for the eradication of "hidden" tumor-cells, being the first vaccination method in the field having this unexpected beneficial effect. As know to the person skilled in the art, the "hidden" tumor-cells present the most aggressive behavior as the immune system either recognizes them as itself, or does not recognize them at all. Three categories of hidden tumor-cells can be differentiated:

- the first and the worst category comprises the "dormant tumor cells", which do not show a malignant character while studied, are chemoresistant, but not heat resistant. These cells are mostly in the tumor-mass, so they are not affected by a far away heating. Thus, due to the intensive heat-exchange with the large volume of circulating blood, the PRF intravascular stimulation having a short-range effect in thermodynamical meaning, does not have any effect on the "dormant tumor cells". However, these cells are targeted by the vaccination method according to the present invention.
- a second category of hidden cells are the disseminated cells, which are circulating in the blood. Because of their low concentration, their presence in the blood is currently impossible to be detected.
- a third category of hidden cells is the micrometastases. The micromestastases are the most dangerous and invisible parts of the malignant development. The resolution of the currently used imaging systems (PET, MRI, CT, SPECT, Usound, etc) allow the detection of micrometastases only after they form aggregates composed of few millions of cells, as their resolution is in the range of mm. At our knowledge none of the prior art methods affects the micrometastases. However, the vaccination method according to the present invention provides a benefic effect against these cancer cells.

Furthermore, the present invention is directed to immune stimulants for treatment of metastases even in the cases when the present imaging methods are not able to detect these; or for prevention of relapse of the cancer disease, wherein the immune stimulant is applied in association with radiofrequency waves using capacitive coupling. The radiofrequency waves can be generated by any conventional RF hyperthermia device using radiofrequency (RF) waves in a condenser arrangement of at least two electrodes, which are preferably equipotential over their total surface, using RF-current of preferably 13.56 MHz (see WO 2009/092612 or WO 2010/0437372). The at least one RF-electrode and the at least one counter electrode are the electromagnetic energy transfer means, which are part of a condenser for directing energy to a target. The RF hyperthermia device applied in the present invention uses capacitive coupling, alternating current (AC) and radiofrequency (RF).

The radiofrequency (RF) used by the RF hyperthermia device is low and does not exceed 50 MHz. In contrast, the radiation hyperthermia devices have to use a high frequency of at least 100 MHz, otherwise accurate focusing is impossible. Generally, the antenna (radiative) has to be optimized to 50 Ohm (this is the accepted standard). This function is made by the tuner. In the present invention the low frequency of preferably 6.78 MHz, 13.56 MHz, 27.12 MHz, or 40.68 MHz or any value in between is preferred. In contrast common radiative hyperthermia uses short wavelength and high frequency in the range of 70-2400 MHz.

The radiofrequency (RF) hyperthermia device itself comprises at least a radiofrequency source, an amplifier, a sensor, optional a feedback amplifier and optionally a modulation signal generator. Suitable RF hyperthermia devices are for example disclosed in the U.S. application Ser. No. 13/123,838 or the U.S. application Ser. No. 12/863,418. The RF hyperthermia device used within the present invention is quite different from the hyperthermia devices of the state of the art as outlined in the following.

A state-of-the-art hyperthermia device is described in US 2004/0230263 A1. It differs from the RF hyperthermia device applied in the present invention in the following features:

- In the device of US 2004/0230263 A1 dipole antennas (radiative coupling) are used. Radiative RF is applied through the patient or more precisely through the target tissue by using absorbed RF radiation.
- In the radiative solution the target is independent from the circuit, the feedback is made by the standing-wave-ratio (SWR) only, which measures the reflected power in comparison to the forwarded. The RF hyperthermia device applied in the present invention does not use dipole antennas; a condenser arrangement is used, wherein the patient's body between the electrodes is the dielectric material which is part of the conductive circuit. This enables a direct control of the target as a part of the circuit, and generates a more precise and accurate feedback for controlling the process. The RF hyperthermia device applied in the present invention uses condenser electrodes (capacitive coupling) for the application of RF waves through the respective body cross section.
- The conventional hyperthermia device induces phase-shifted interference between the antennas and interference of their standing wave radiation in order to tune the focus on the desired area. The device used in the present invention uses conductivity differences of the respective tissues (e.g. malignant tumor tissue has a higher conductivity than healthy tissue), thus leading to an automatic selection of the focus to the malignant tumor tissue. This has immediate consequences on expansible organs like the lung or the heart, or if the patient moves during a treatment session which may exceed one hour.
- Moreover, while the focus in the conventional device remains at the spot on which it was focused before, independent from the actual position of the tumor, the device used by the present invention follows any movement of the target because the RF current automatically flows in the correct direction.
- In the conventional hyperthermia device the target is treated like an electrically independent object absorbing the radiated energy thereby causing burns and vehement necrosis. The present invention uses the target as a part of the electric circuit, as a dielectric material of a condenser in a resonant circuit. Consequently, the heating process is carried out and controlled in a different fashion. The conventional hyperthermia device uses SAR (specific absorption rate) absorbed energy as the only heating mechanism for achieving a beneficial effect, thus by heating up the tumor, the tumor cells are burned. The present invention uses Joule heat ($Q=I^2R$) by converting the current flow into heat as well as the potential difference for an electric field effect, thereby causing apoptosis in the cancer cells and thus, triggering the immune system to an immune response. Thus, the patient's own immune systems starts fighting against the recognized single cancer cells, wherein the fight is supported by the administered immune stimulants thus, becoming an effective cancer therapy especially for the very first initial stadium of cancer development, which is undetectable by any known diagnostic methods and for the treatment of metastases due to the fact that the treatment is systemic and not local as in the state of the art.

The conventional hyperthermia device controls temperature only as a tool for reproducing and standardizing the therapy. In contrast, the device applied in the present invention uses the absorbed energy (J/kg) and the conductivity of the patient (S=1/R) for strict control of the therapy conditions. The conventional hyperthermia device implicitly assumes that the success of the therapy depends only on the heat effect relative to the achieved temperature. By such a method mainly necrosis is caused in the target tissue. The device used in the present invention, however, does not require achieving such high temperatures at which necrosis occurs, because the field effect causes apoptosis at lower temperatures. Thus the RF hyperthermia device applied in the present invention treats tumorous or malignant tissue, cancer, tumors and especially metastases and single cancer cells by inducing and/or causing apoptosis and by enabling the immune system to recognize the cancer cells, and to start fighting against them, while common devices using radiative coupling induce necrosis and are not even able to treat metastases and single cancer cells in the initial state of cancer development or the initial state of cancer relapse. The RF hyperthermia device applied in the present invention does not use radiative coupling and uses capacitive coupling, wherein the patient is the dielectric material or dielectricum as part of the electric circuit.

The differences can be summarized as follows:
1. RFA devices use RF-radiation/absorption;
2. The inventive vaccination uses RF current conduction;
3. RFA devices use a needle as antenna for radiative coupling;
4. The inventive vaccination uses electrodes for capacitive coupling;
5. RFA devices require high frequencies (above 130 MHz);
6. The inventive vaccination requires frequencies below 50 MHz and preferably 6.78 MHz, 13.56 MHz, 27.12 MHz, or 40.68 MHz and most preferably 13.56 MHz;
7. RFA devices cause necrosis (no vaccination possible);
8. The inventive vaccination causes apoptosis and recognition of cancer cells and thus leads to vaccination;
9. RFA devices are used invasively and locally;
10. The inventive vaccination is used not invasively and systemically;
11. RFA devices are only useful to treat solid tumors
12. The inventive vaccination is especially useful to treat isolated and widespread cancer cells, such as metastases and the initial stadium of cancer development The common immuno-therapeutic vaccination methods are applicable only in very limited conditions by the state of art. The modality faces with various requests of the modern era. It has to be:
Effective
Personalized (specific)
Applicable for all the tumor-lesions
Suitable for blocking the relapse and metastases
Simple applicable
Not too expensive These criteria are not fulfilled by the state of the art tumor vaccination methods. The applied therapies were not effective in general, only in some special fields. The main reason of the failures and low efficacy resides in the low immunogenic activity of the tumor cells in general cases. The immune system did not recognize the tumor cells, and thus was not active to eliminate them. The immune stimulation without specific immune identification processes (e.g. cytokine therapies with IL-2, IL-8, TNF, etc.) could far not reach the desired efficacy. Most of the therapies are working off-situ, taking the immuno-potential from the patients, off-situ manipulating said cells and giving the said off-situ manipulated cells or labor-made vaccine back to the patient. The off-situ therapies are very complicated, very expensive and tedious, but most of the time not effective enough: The "foreignness" and the low concentration of the off situ manipulated cells, as well as the missing further reproduction (continuing the process) of said cells limit the complete action.

The methods (or also called vaccination methods) of the present invention apply a radiofrequency field generated by capacitive coupling and not by a dipole antenna and this radiofrequency field or the radiofrequency waves thereof enable the immune system of the treated patient to recognize cancer cells, which were so far not recognized by the immune system of the patient. It is assumed that the radiofrequency field generated by capacitive coupling or respectively the radiofrequency waves of this radiofrequency field cause stress in the cancer cells, which leads to the effect that the cancer cells cannot keep hiding their surface recognition sequences or structures and/or are destroyed by the heat generated by the radiofrequency waves in the cancer cells and/or are forced by the radiofrequency field and the radiofrequency waves thereof to undergo apoptosis thus, enabling the patient's immune system to recognize the no longer hidden surface structures or the degradation products of the destroyed or apoptotic cancer cells. The immune stimulant administered in addition to the radiofrequency field/radiofrequency waves further supports the immune system to attack and destroy the cancer cells effectively. In addition, a memory of the immune system is created thus, enabling the immune system to recognize cancer cells, and especially single cancer cells in other parts of the body. Thus, the present invention is directed to a method or vaccination method, which may also kill cancer cells directly but first of all, enables the patient's own immune system to first recognize the cancer cells and then kill the cancer cells effectively. Thus, the method or vaccination method of the present invention supports the immune system to fight against the cancer cells and thus, the cancer disease and can therefore be regarded as indirect method to treat cancer and especially primary cancer, single cancer cells, and metastases and prevent relapse of a cancer disease.

The present invention provides immune stimulants, vaccines and vaccination methods for the primary cancer, as well as for the treatment of metastases and also for the prevention of relapse of the cancer disease especially after a successfully treated cancer disease by supporting patients' own immune system to recognize hidden cancer cells and kill the recognized cancer cells. The inventive vaccination method is very sensitive and enables the immune system to recognize cancer cells before they can be detected by any analytical state of the art method. Moreover, due to the very low toxicity and very low side effects of the vaccination method disclosed herein, the method can be used after treatment of a cancer disease in order to prevent relapse of the cancer disease.

"In-vivo" means in our nomenclature, that the appropriate antigen formation is made inside the patient's body, so that no invasive process is involved. Thus, the vaccination method of the present invention can also be called in vivo vaccination method. The in-situ nomenclature means that the immunization, i.e. the recognition of the specific TSA, is processed actually in the tumor. Thus, the vaccination method of the present invention can also be called in-situ vaccination method or in-situ and in vivo vaccination method.

As used herein, the term "personalized" refers to the fact that the immunization is done with the patient's own TSA (tumor specific antigen). As mentioned above, most of the tumor vaccinations use artificial antigens, which are in many cases not identical to the patient's own tumor specific (TSA) or tumor associated (TAA) antigens. In most of the cases, the major challenge is the use of general (non-personalized) proteins or protein-cocktails for immune effects, which could be effective for some patients and some kinds of cancer, but far not for all. These conditions make the treatment uncontrollable and unpredictable. In accordance to the invention, the vaccination uses the own unique protein molecule pattern of the patients malignant cells and no artificial ones. The inventive vaccination creates the patient's own, very individual and incomparable TSA "cocktail" for actual and precise immune identification. In the state of the art such a personalized, simple and cheap tumor vaccination does not exist. The existing processes are too sophisticated, highly complicated, very expensive and rarely effective. For example, the TSA could be obtained from the out-operated specimen. After its in-vitro recognition process with dendritic cells (DC) and after special immune activation the "vaccine" is injected directly into the tumor or systemically administered to the patient. The inventive vaccination induces specific highly immunogenic cell death. The vaccination method of the present invention can also be called personalized in-situ vaccination method, or personalized in vivo vaccination method, or personalized in-situ and in vivo vaccination method.

The term "apoptosis induction": The inventive vaccine can induce special immunogenic apoptosis with apoptotic body formation. Apoptotic bodies (loaded with tumor cell components, including the patient's very own TSAs) can be phagocytized easily by the appropriate APC (antigen presenting cells, DCs). Research results in the past show a major immuno-stimulative effect of the stress-induced apoptosis. The apoptotic bodies produced in this process contain a large amount of HSPs together with the specific TSA. Their phagocytosis by APC induces strong and specific immune reactions.

The term "DAMP/SAMP": The inventive vaccine can induce unique molecular changes such as Damage-associated molecular pattern molecules (DAMP) and -stress-associated molecular pattern molecules (SAMP) in the tumor cells that can be on one side immune stimulative and on the other side can promote the immune recognition of the tumor cells. Although it was thought that apoptotic cells, when rapidly phagocytozed, underwent a silent death that did not trigger an immune response, in recent years a new concept of immunogenic cell death (ICD) has emerged. The immunogenic characteristics of ICD are mainly mediated by damage-associated molecular patterns (DAMPs), which include surface-exposed calreticulin (CRT), secreted ATP and released high mobility group protein B1 (HMGB1).

The term "HSP overexpression": HSP chaperone proteins have important and primary role in tumor immunology processes. HSPs of the cytosol such as Hsp70 and Hsp90, and of the ER, such as gp96, bind antigenic peptides generated within the cell. These antigenic peptides are transported by HSPs to the MHC class I molecules present on the cell surface for presentation to lymphocytes. Moreover, peptides that are chaperoned by HSPs are released extracellularly and these HSP-peptide complexes are taken up by APCs, i.e., macrophages and dendritic cells, via receptor-mediated endocytosis. Thus HSPs promote antigen recognition by APCs. The terms "HSP overexpression" and "HSP externalization" refer to the following: By application of an immune stimulant in association with radiofrequency waves using capacitive coupling several HSP proteins are expressed in the malignant cells in an increased rate (being over the rate of untreated cells) and further more HSPs are present on the cell surface or are secreted by these cells.

The term "TRAIL (DR5) overexpression" refers to an increased expression of the gene encoding for TRAIL: According to many publications this molecule has key role in the antitumor immune reactions. The tumor distortion generated by the inventive vaccine causes such DAMP and SAMP, which result in major tumor specific immune reactions by liberation of the patient's own tumor specific antigens (TSA). In this way, the vaccination is in-situ and no labor manipulation is necessary for its success. The inventive vaccination fulfills all the above listed requirements of vaccinations, especially when applied together with other immune stimulative processes. The inventive vaccination affects systemically (abscopal or bystander effect) and the treatment is active on the disseminated malignant cells and on the far distance formed metastases too, especially when applied together with other immune stimulative processes. The induced immune reaction also forms proper immune memory, which blocks the relapses of the disease, i.e. the cancer disease.

Advantages of the inventive vaccine are summarized as follows:
  Immunogenic apoptotic body formation
  TSA-HSP cross priming
  Effective antigen recognition by APCs
  APC cell activation and maturation
  Specific cytotoxic T cell activation by APCs
  Destruction of distant metastases far away from the treated tumor
  Development of the specific immune memory preventing the tumor recurrence and the cancer relapse.

The inventive vaccination achieves effects, which could not be reached by common cancer treatment strategies. One mode of action of the inventive vaccine could probably be explained as follows: The TSAs in apoptotic bodies produced by the inventive vaccination became reachable by APCs. Due to the identification of the TSA and the adjuvant HSP enrichment by the strong stress of the treatment with the inventive vaccine, the APCs induce remarkable immune reactions, including
  1. The activation of the CTL system to obtaine the patient's specific TSA information. This immune reaction allows finding and destroying the malignant cells in far distant metastases or in disseminated form.
  2. The creation of an effective immune memory that results in the blockage of the later relapse of the malignancy.

The complete process is well promoted by the immune stimulants, which converts the local effect into systemic effect. The abscopal (bystander) effect could be oriented and controlled.

Treatment of the following primary cancer types can be achieved and metastases of the following cancer types can be treated and also relapse of the following cancer types can be prevented by the present invention: adenocarcinoma, choroidal melanoma, acute leukemia, acoustic neurinoma, ampullary carcinoma, anal carcinoma, astrocytoma, basal cell carcinoma, pancreatic cancer, desmoid tumor, bladder cancer, bronchial carcinoma, non-small cell lung cancer (NSCLC), breast cancer, Burkitt's lymphoma, corpus cancer, CUP-syndrome (carcinoma of unknown primary), colorectal cancer, small intestine cancer, small intestinal tumors, ovarian cancer, endometrial carcinoma, ependymoma, epithelial cancer types, Ewing's tumors, gastrointestinal tumors, gastric cancer, gallbladder cancer, gall bladder carcinomas, uterine cancer, cervical cancer, cervix, glioblastomas, gynecologic tumors, ear, nose and throat tumors, hematologic neoplasias, hairy cell leukemia, urethral cancer, skin cancer, skin testis cancer, brain tumors (gliomas), brain metastases, testicle cancer, hypophysis tumor, carcinoids, Kaposi's sarcoma, laryngeal cancer, germ cell tumor, bone cancer, colorectal carcinoma, head and neck tumors (tumors of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumors gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarial carcinoma, pancreatic carcinoma, penile cancer, plasmocytoma, squamous cell carcinoma of the head and neck (SCCHN), prostate cancer, pharyngeal cancer, rectal carcinoma, retinoblastoma, vaginal cancer, thyroid carcinoma, Schneeberger disease, esophageal cancer, spinalioms, T-cell lymphoma (mycosis fungoides), thymoma, tube carcinoma, eye tumors, urethral cancer, urologic tumors, urothelial carcinoma, vulva cancer, wart appearance, soft tissue tumors, soft tissue sarcoma, Wilm's tumor, cervical carcinoma and tongue cancer. Particularly suitable for treatment are, for example, astrocytomas, glioblastomas, pancreatic cancer, bronchial cancer, breast cancer, colorectal cancer, ovarian cancer, gastric cancer, laryngeal cancer, malignant melanoma, oesophageal cancer, cervical cancer, liver cancer, bladder cancer, and renal cell cancer.

In other words, the vaccination method disclosed herein enables and supports the immune system of the patient to fight against the above-mentioned cancer types or to kill cancer cells of the above-mentioned cancer types.

Moreover, the present vaccine does not have and does not cause any serious side effects, so that the inventive vaccination is suitable to be combined with common cancer therapies such as chemotherapies with one or more of the following chemotherapeutic agents: actinomycin D, aminoglutethimide, amsacrin, anastrozol, antagonists of purine and pyrimidine bases, anthracycline, aromatase inhibitors, asparaginase, antiestrogenes, bexaroten, bleomycin, buselerin, busulfan, camptothecin derivates, capecitabin, carboplatin, carmustine, chlorambucil, cladribin, cyclophsphamide, cytarabin, cytosinarabinoside, alkylating cytostatics, dacarbacin, dactinomycin, daunorubicin, docetaxel, doxorubicin (adriamycin), doxorubicin lipo, epirubicin, estramustine, etoposid, exemestan, fludarabin, fluorouracil, folic acid antagonists, formestan, gemcitabin, glucocorticoides, goselerin, hormone antagonists, hycamtin, hydroxy urea, idarubicin, ifosfamid, imatinib, irinotecan, letrozol, leuprorelin, lomustin, melphalan, mercaptopurine, methotrexate, miltefosin, mitomycine, mitosis inhibitors, mitoxantron, nimustine, oxaliplatin, paclitaxel, pentostatin, procarbacin, tamoxifen, temozolomid, teniposid, testolacton, thiotepa, thioguanine, topoisomerase inhibitors, topotecan, treosulfan, tretinoin, triptorelin, trofosfamide, vinblastine, vincristine, vindesine, vinorelbine, antibiotics with cytotoxic activities.

Abbreviations

APC: antigen presenting cell
CTL: cytotoxic T lymphocyte
DAMP: Damage Associated Molecular Pattern
DC: dendritic cell
DR5 (TRAIL): death receptor (TNF-related apoptosis-inducing ligand)
GM-CSF: granulocyte-macrophage colony stimulating factor
HMGB1: high mobility group box
HSP: heat shock protein
IHCH: immunohistochemical analysisIL: interleukin
LPS: lipopolysaccharide
NK: natural killer cell
OTM: oncothermia method (radiofrequency waves using capacitive coupling in a condenser arrangement)
SAMP: Stress Associated Molecular Pattern
TAA: tumor-associated antigen
TLR: toll like receptor
TNF: tumor necrosis factor
TSA: tumor specific antigen FIG. 1 shows how the RFA method works: An antenna needle is inserted into the solid tumor and heat is produced by the applied local RF current, which burns the tumor and causes vehement necrosis. RFA is an invasive method, using RF current to produce heat and thus causing ablation by an antenna arrangement using radiative coupling.

Figure 2:
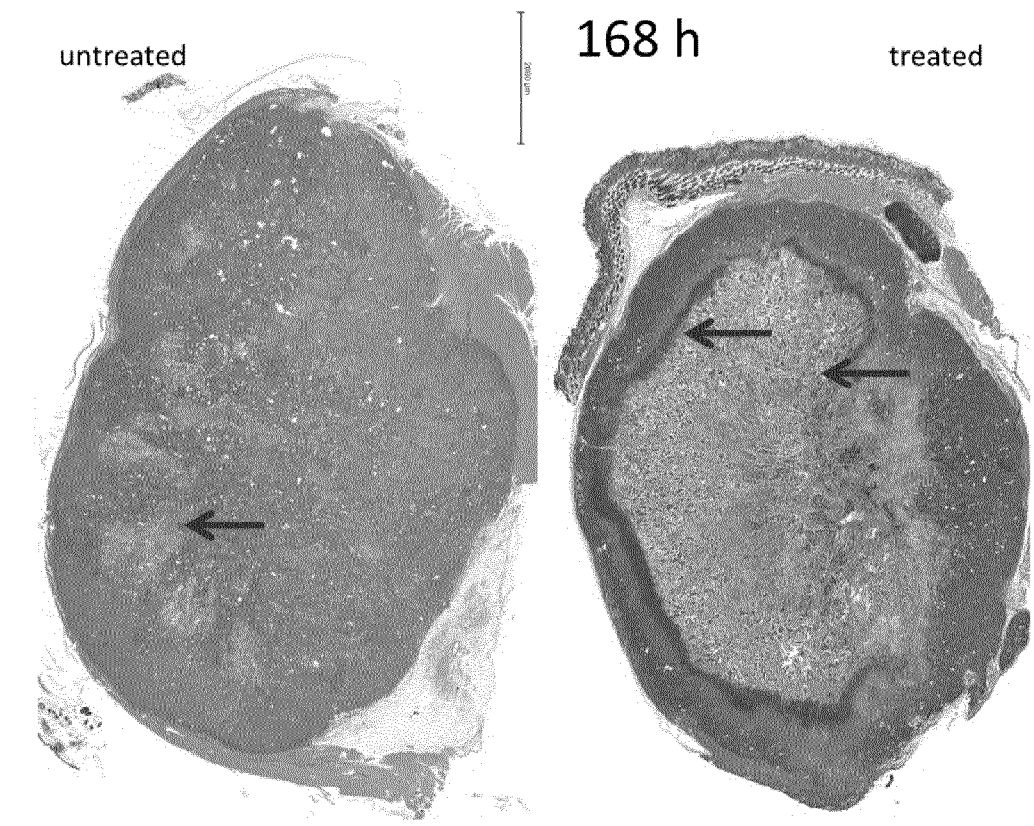
FIG. 2 shows a HE-staining on a slide of a dissected tumor.

FIG. 2 shows a HE-staining on a slide of a dissected tumor. It can be seen that a clear invasion ring appears (arrows) around the tumor. Thus, a strong immune reaction after treatment in accordance with the present invention occurs.

Figure 3A:
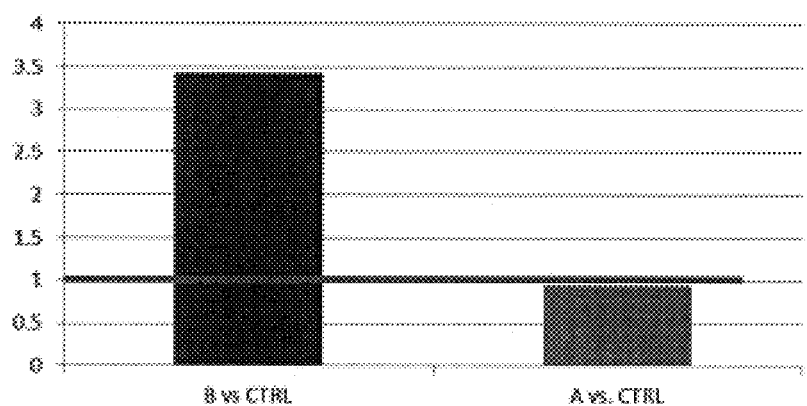
FIG. 3A shows the overexpression of HSPA1A in tumors treated in accordance with the present invention.
Figure 3B:
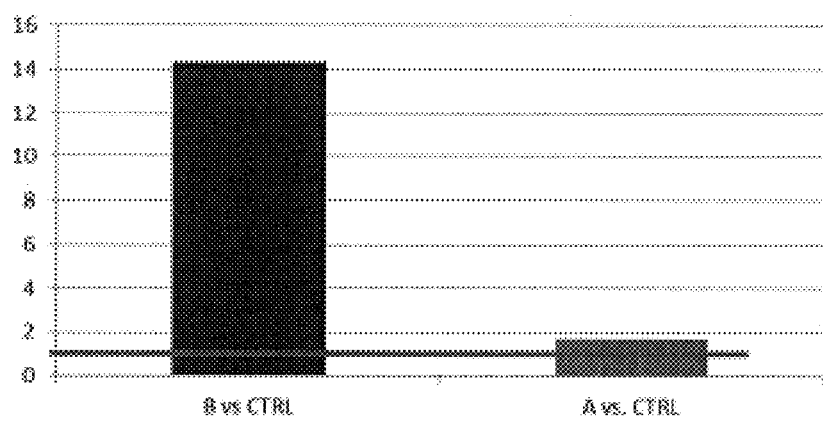
FIG. 3B shows the overexpression of HSPA6 in tumors treated in accordance with the present invention.
Figure 3C:
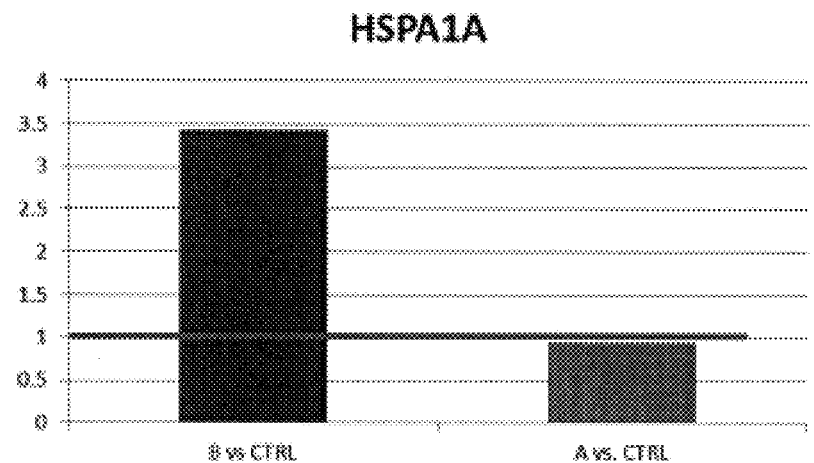
FIG. 3C shows the overexpression of HSPA8 in tumors treated in accordance with the present invention.
Figure 3D:
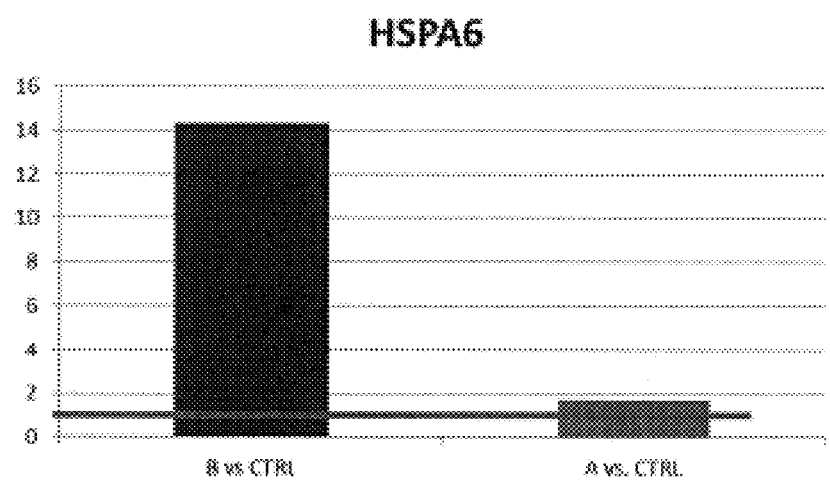
FIG. 3D shows the overexpression of HSPD in tumors treated in accordance with the present invention.

FIG. 3 shows an overexpression of different HSP (FIG. 3A: HSPA1A, FIG. 3B: HSPA6, FIG. 3C: HSPA8, FIG. 3D: HSPD) in tumors treated in accordance with the present invention. HSP production was measured on mRNA level (B corresponds to the HSP production in the treated tumor [black], A corresponds to the HSP production in the untreated tumor [gray], CTRL is the untreated control). The gray-line corresponds to the unchanged level.

Figure 4:
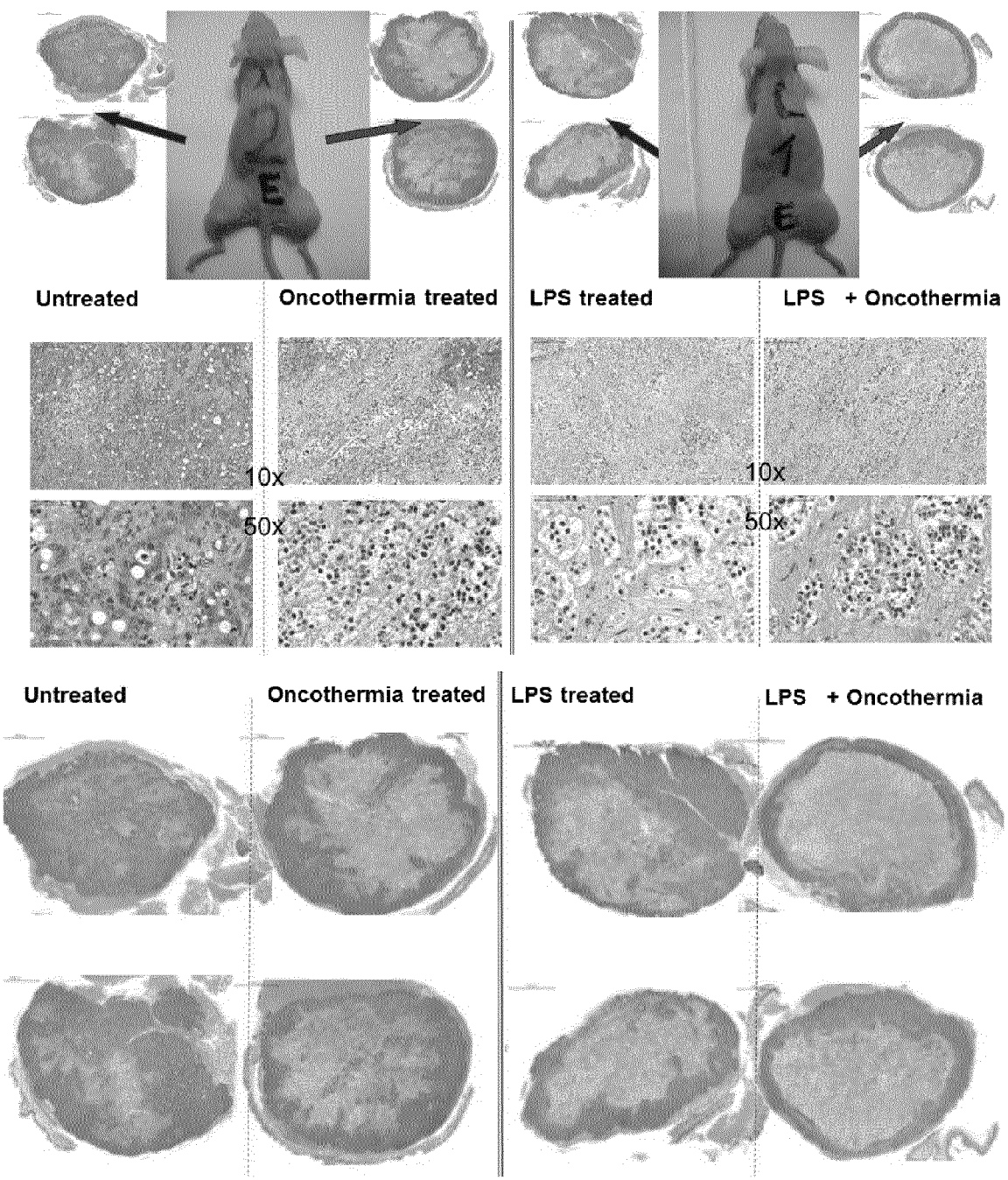
FIG. 4 shows the cell killing effect from the present vaccine.

FIG. 4 proves that the present vaccine provides a systemic effect in mice. The systemic administration of LPS (lipopolysaccharide from E. coli, 100 µg LPS in 100 µl Salsol solution) results in massive cell killing effect of the untreated far-distance tumor too.

Figure 5:
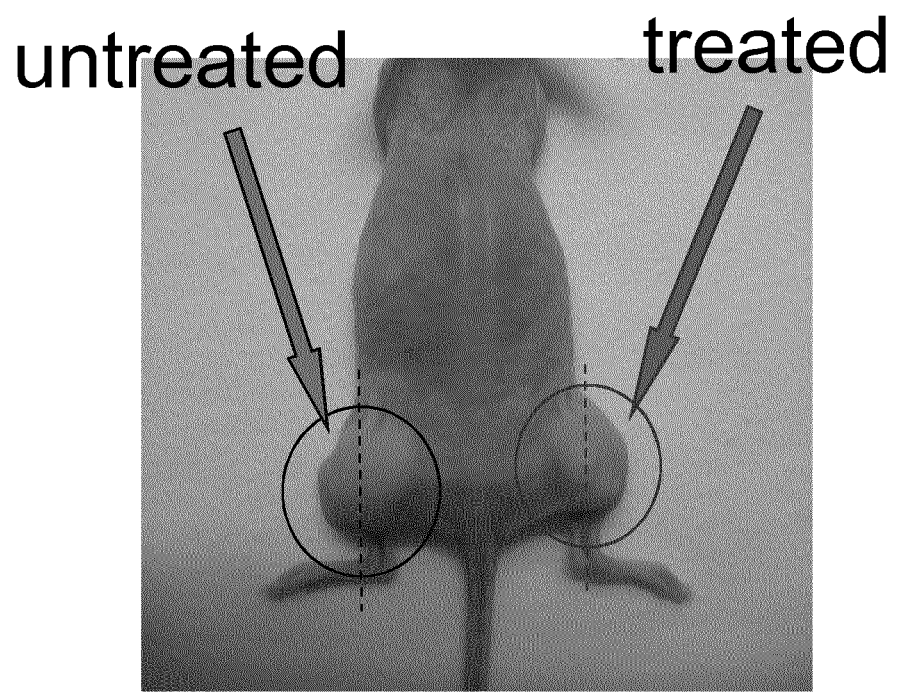
FIG. 5 depicts the mice-model used in the experiments.

FIG. 5 shows the mice-model used for the experiments: on female nude mice BALB/c (nu/nu), two symmetrically, far-distance tumors were induced by administration at the femoral region on both sides of 6×106 cells in 0.1 mL of serum free medium suitable to induce tumor growth. Only mice developing symmetrically and approximately same size tumors were used. Only the right tumor was treated.

Figure 6:
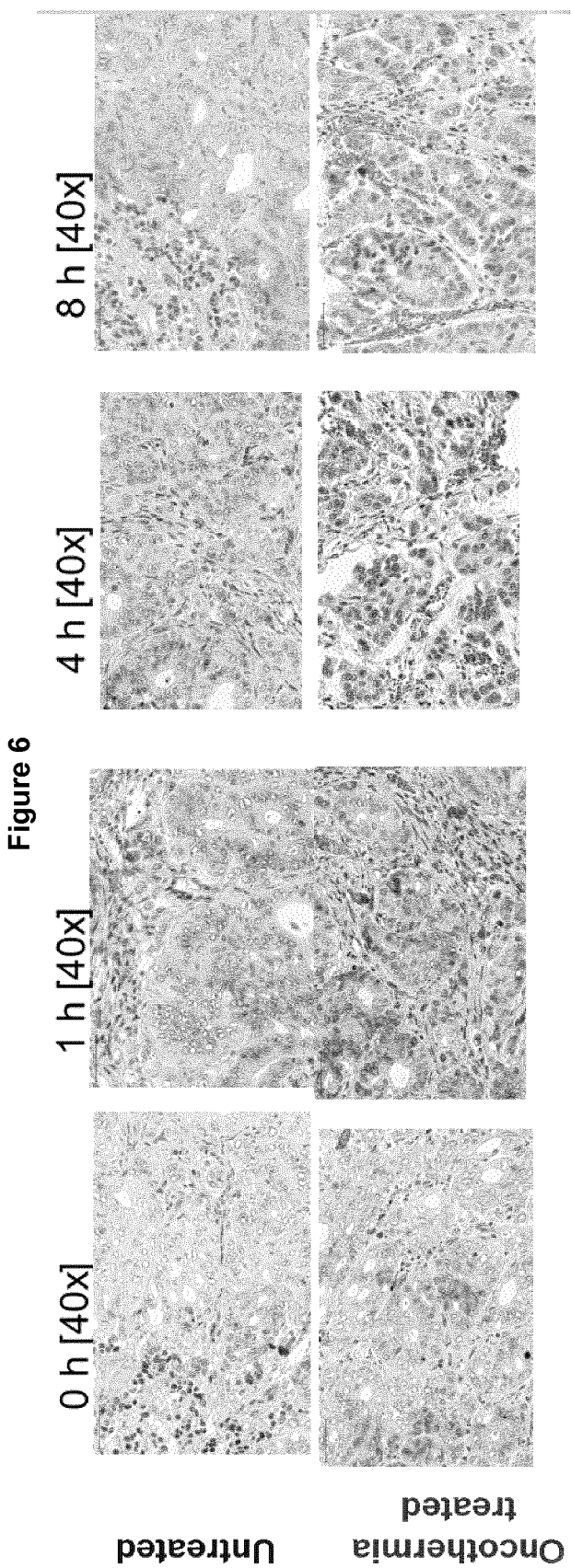
FIG. 6 shows the systemic effect of the present invention used in human treatment.

FIG. 6 shows the systemic effect of the present invention, when used in human treatment. The patient was diagnosed with non-small cell lung cancer and presents various metastases situated far away from the location of the primary cancer: in the neck, in the lumbar region, in armpit etc. Although only the primary tumor was treated with the radiofrequency using capacitive coupling (single shoot, 30 min, 42° C.), the administration of the GM-GSF (Leukine®) in association with the radiofrequency using capacitive coupling resulted in a systemic effect having a beneficial effect also on the far-distances metastases, which disappear.

Figure 7:
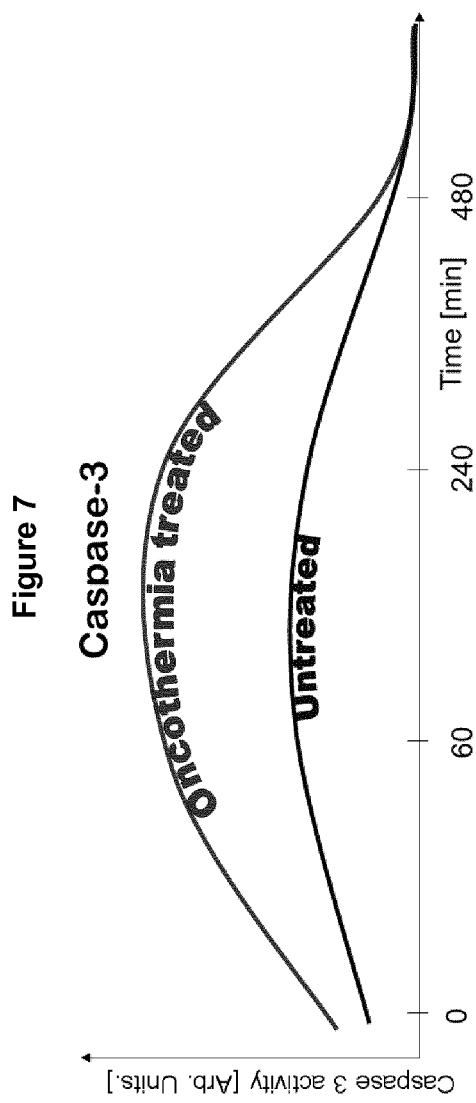
FIG. 7 shows the increase in caspase-3 activity in both treated and far-away tumors in nude mice.

FIG. 7 shows the increase in caspase-3 activity in both treated and far-away tumors in nude mice. The caspase-3 activity, which is an important marker of the apoptosis signal-pathway, increases both in treated and far-away untreated tumors in nude mice thus, showing the systemic effect of the present vaccination.

Figure 8:
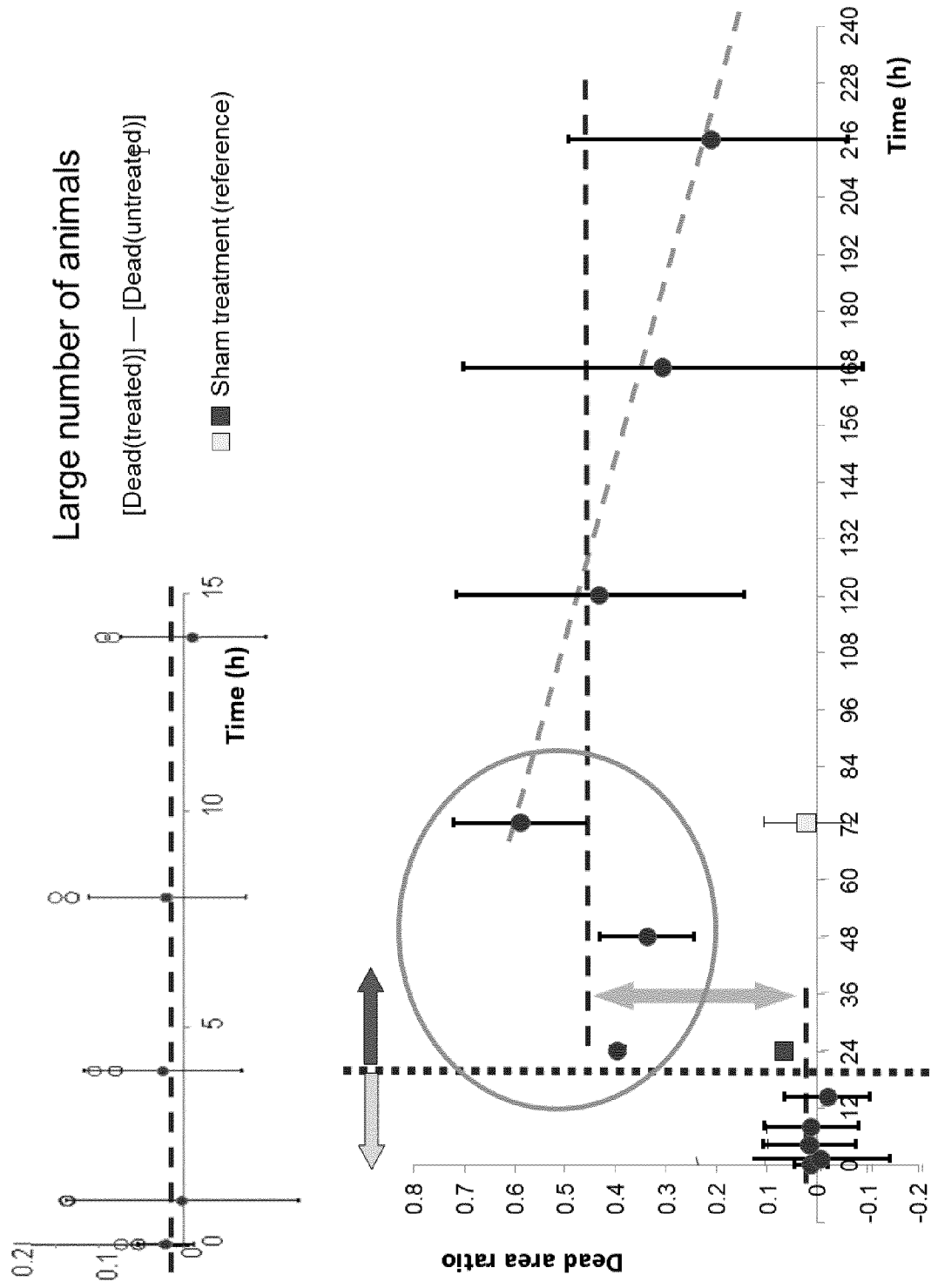
FIG. 8 shows time-series of nude mice xenograft (HT29 human colorectal), single shoot, 30 min, 42° C.

FIG. 8 shows time-series of nude mice xenograft (HT29 human colorectal), single shoot, 30 min, 42° C. Every point represents 3 double tumor-bearing animals. The sacrifice of the animals is made at the time after treatment (indicated on X-axis). The observation, that the apoptosis starts after 24 hours (the insert shows no effect in the first 8 hours) and the difference between the treated and far-away not treated tumor-death lowers, the action started far away from the local treatment.

Figure 9A:
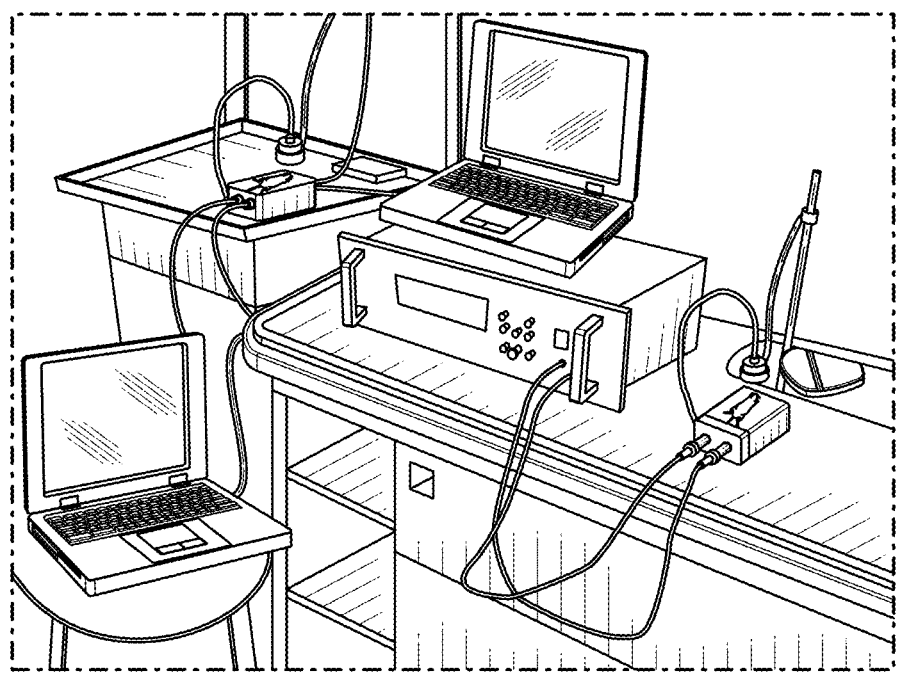
FIG. 9A shows the experimental setup used for the treatment of the animals.
Figure 9B:
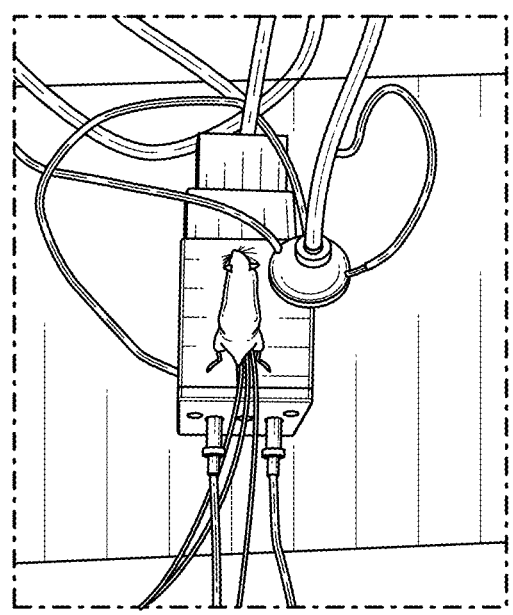
FIG. 9B shows the treatment applicator system with the temperature measurement sensor probe.

FIG. 9 shows
A. the experimental setup used for the treatment of the animals (mice);
B. the treatment applicator system with the temperature measurement sensor probe. One counter-electrode is shiny and underlying the animal and the second electrode is the round applicator above the animal which can be moved to the treatment area.

FIG. 10 sums up the sample evaluation processes. A. Method of tumor dissection; B. Analysis scheme of the tumor sample including analysis of a huge number of mRNA transcripts, 35 apoptosis related proteins, many morphological factors together with all the DAMP associated protein arrangement.

Figure 11:
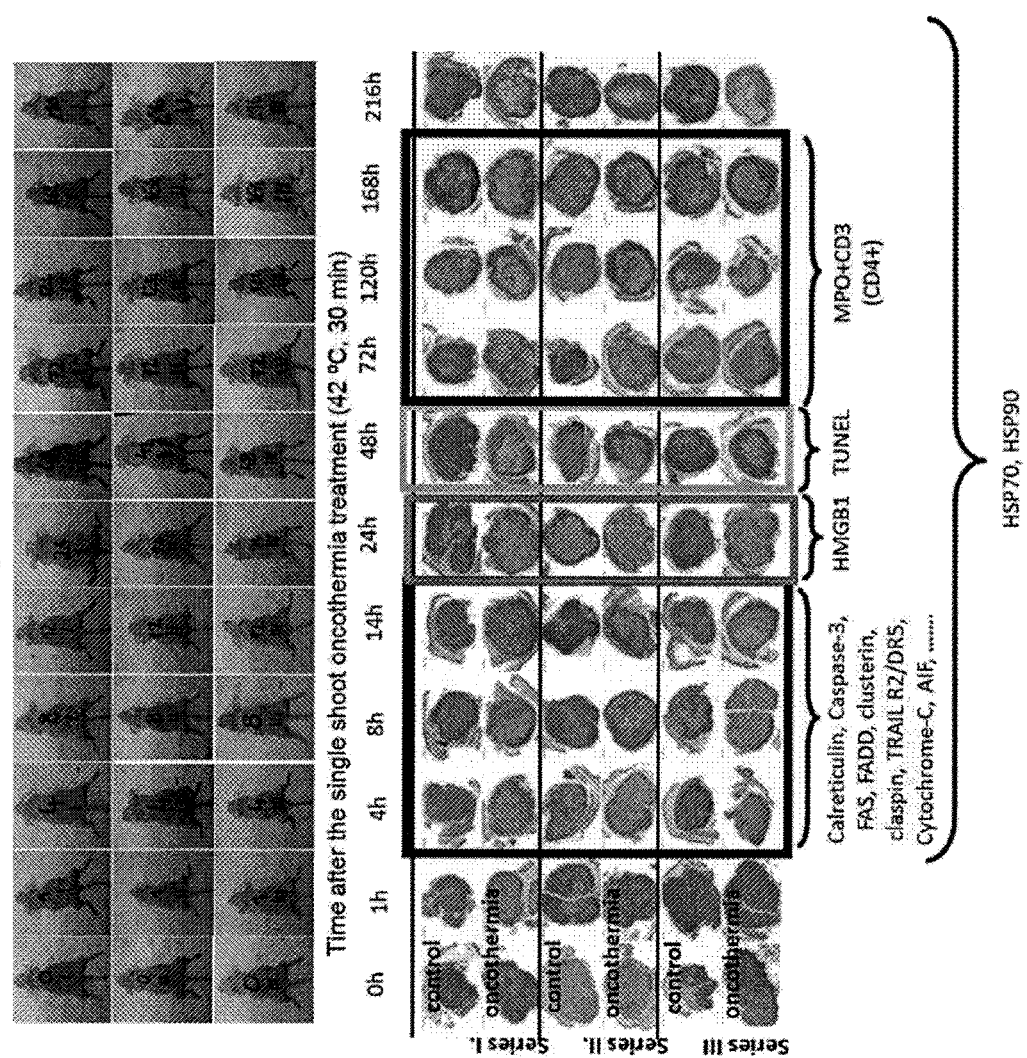
FIG. 11 shows the typical set of time-course study with the measured molecules.

FIG. 11 shows the typical set of time-course study with the measured molecules.

Figure 12:
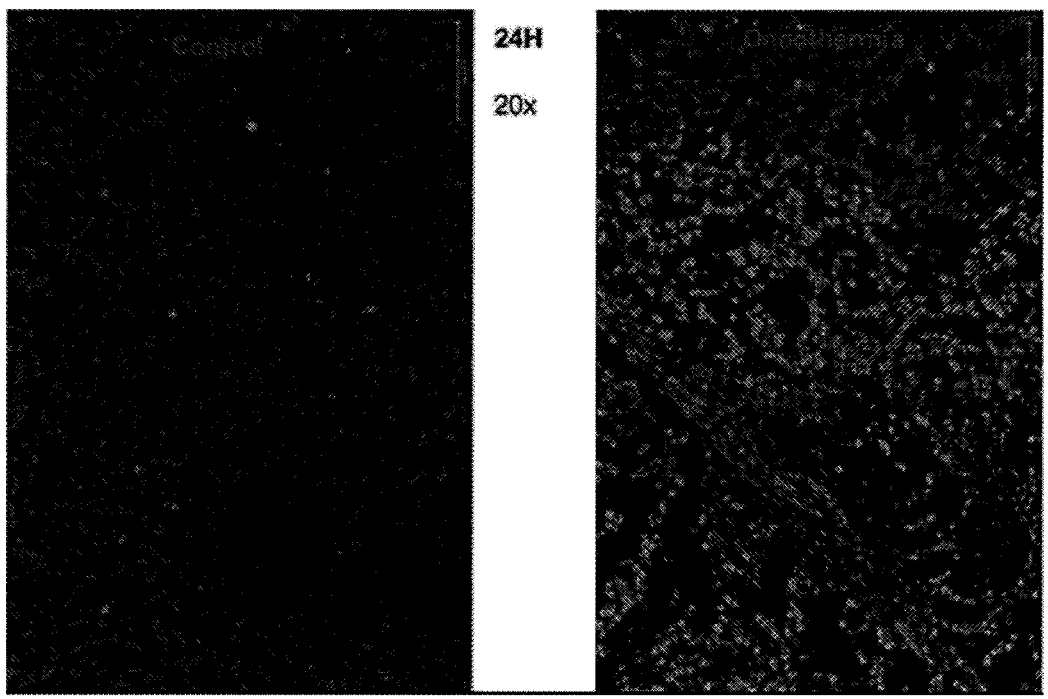
FIG. 12 shows the results of the TUNEL assay.

FIG. 12 shows the results of the TUNEL assay as a proof of apoptosis. The blue is standard DAPI staining (cell nuclei) and the green is TUNEL FITC.

Figure 13:
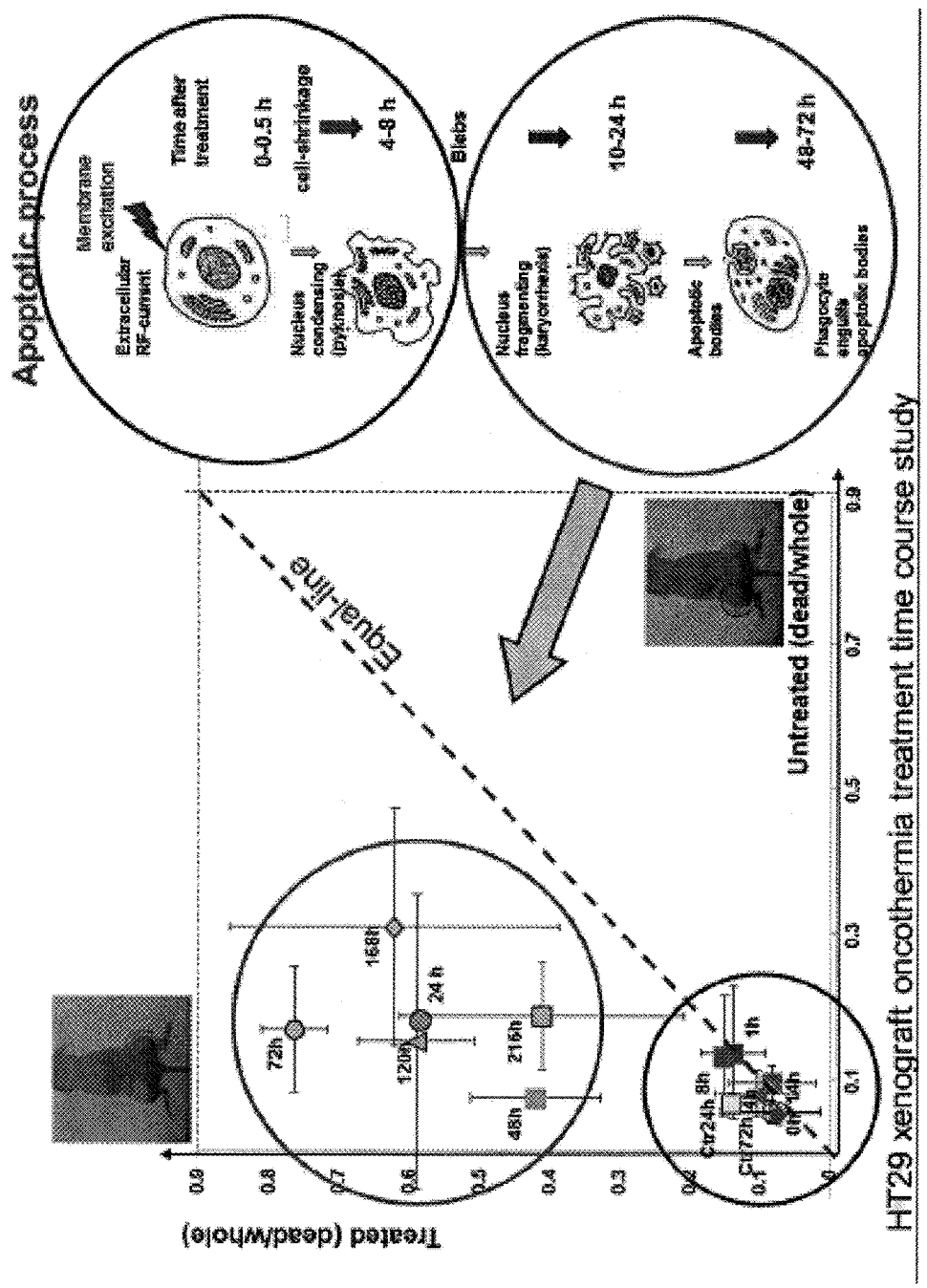
FIG. 13 shows time-course investigation corresponding to the time-scale actions.

FIG. 13 shows in how the time-course investigation well proofs the apoptotic process, having complete correspondence with the time-scale actions.

Figure 14:
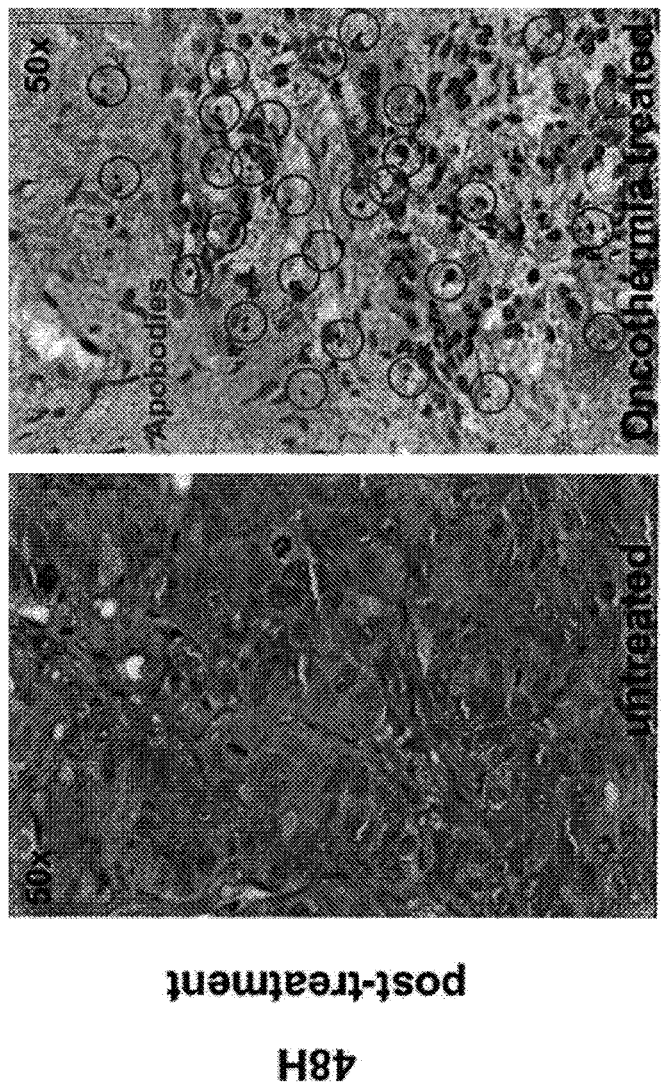
FIG. 14 shows how apoptotic bodies are induced following oncothermia treatment.

FIG. 14 shows how apoptotic bodies are induced following oncothermia treatment. A huge number of apoptotic bodies can be observed in the treated cells in comparison with the untreated ones.

Figure 15:
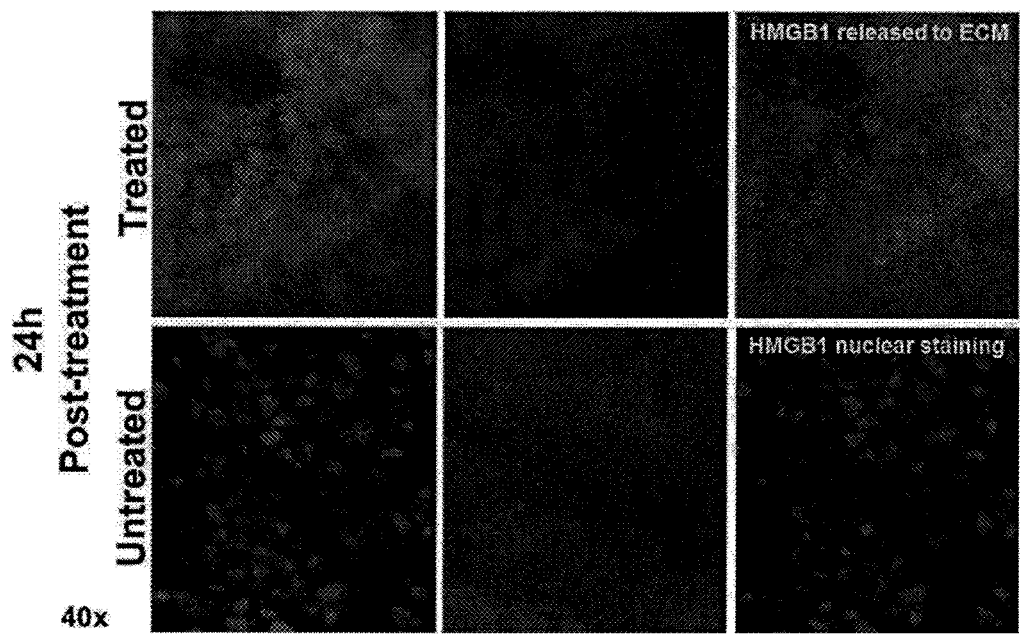
FIG. 15 shows the HMGB1 presentation and release to the extracellular matrix following oncothermia treatment.

FIG. 15 shows the HMGB1 presentation and release to the extracellular matrix following oncothermia treatment.

Figure 16:
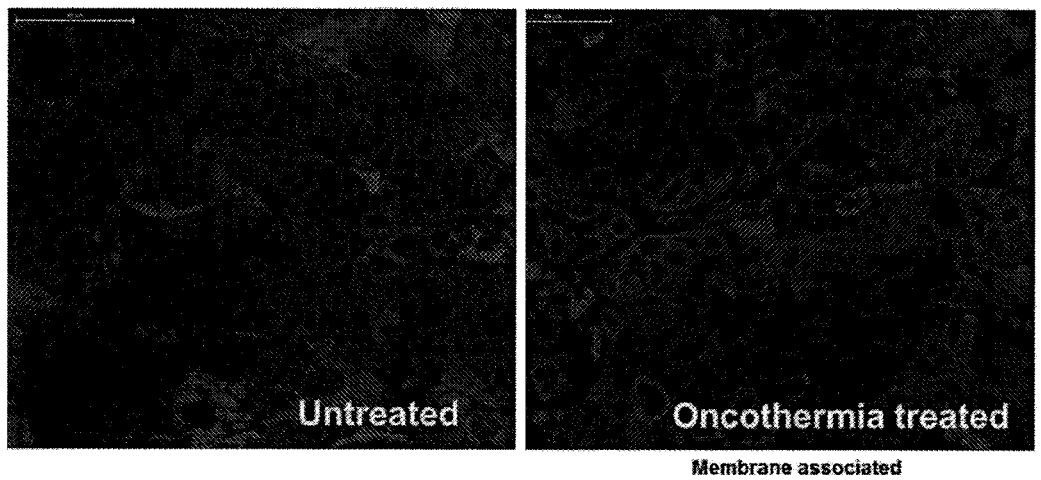
FIG. 16 shows the calreticulin expression post treatment.

FIG. 16 shows the calreticulin expression (4 h, post treatment). Calreticulin is expressed on the cell membrane of the cells treated with oncothermia (radiofrequency waves using capacitive coupling), creating optimal conditions for DAMP.

Figure 17:
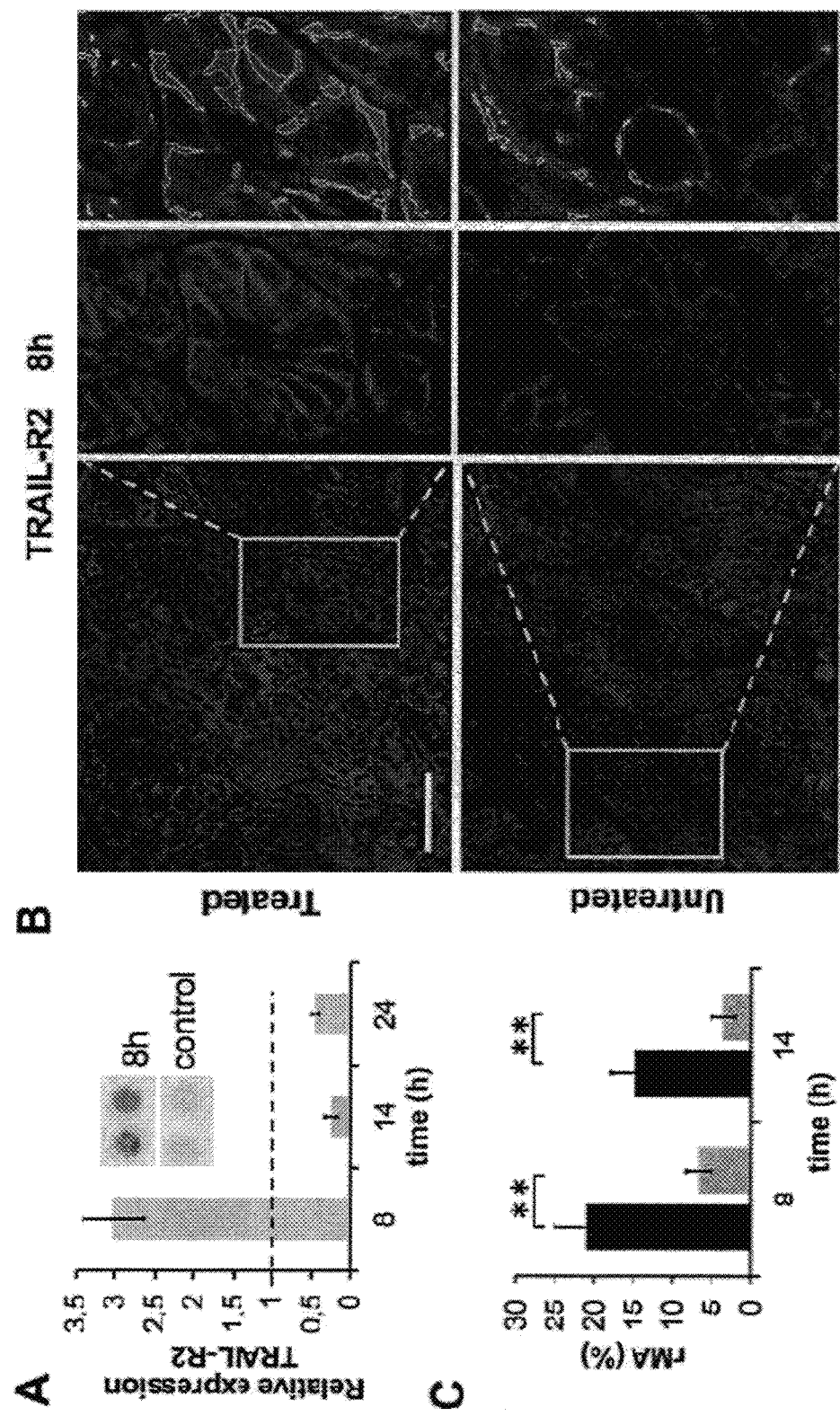
FIG. 17A depicts an upregulation of TRAIL-R2 in HT29 xenograft tumor samples 8 h after oncothermia.
FIG. 17B depicts expression of TRAIL-R2 protein in the tumor cell membranes.
FIG. 17C is a graph showing RMA values of TRAIL-R2 protein expression.
Figure 18A:
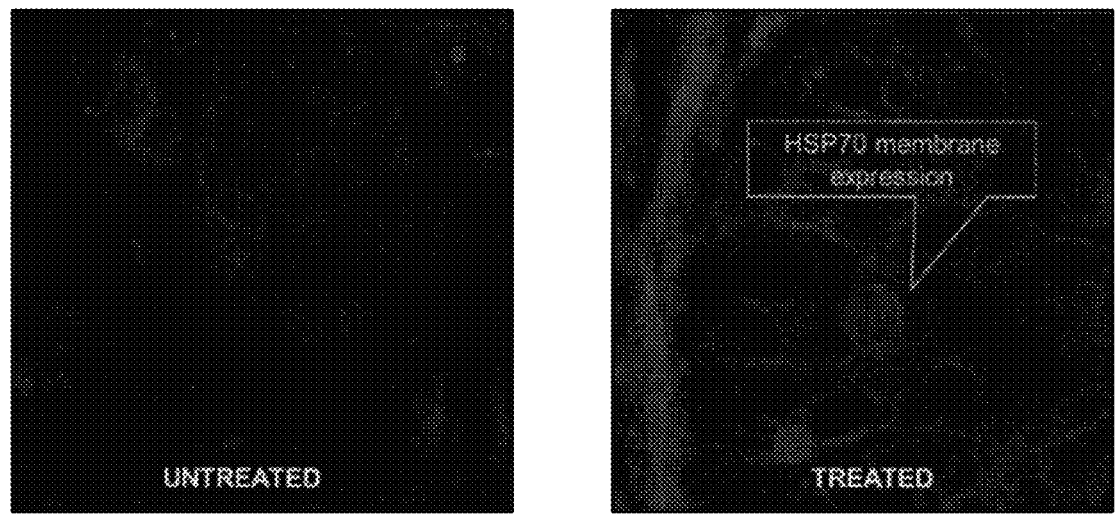
FIGS. 18A and 18B shows the immunfluorescnet detection of HSP70.
Figure 18B:
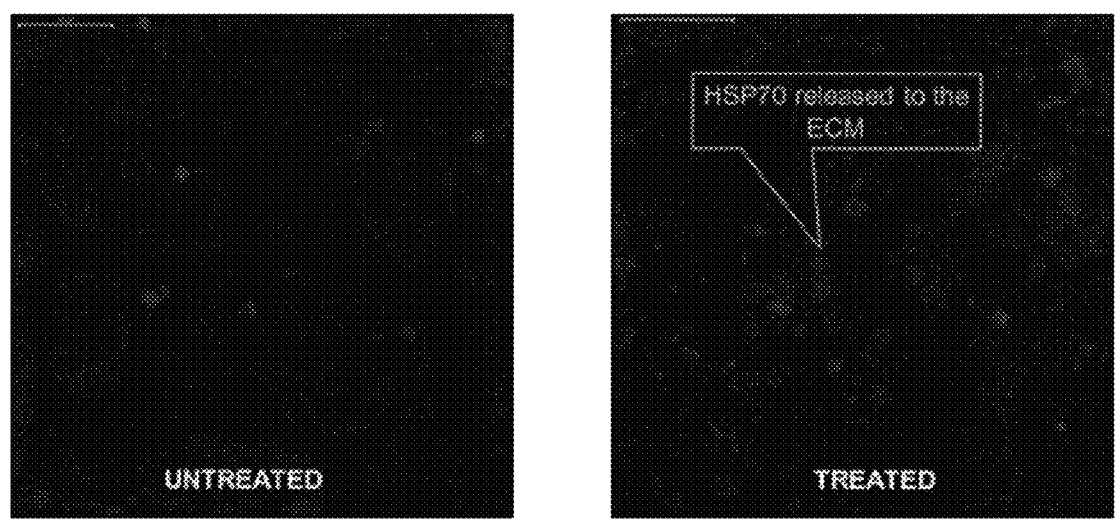

FIG. 17 shows the expression of TRAIL-R2 by measurement the protein level and immunofluorescent detection:

A Upregulation of TRAIL-R2 in HT29 xenograft tumor samples 8 h after oncothermia (radiofrequency waves using capacitive coupling in a condenser arrangement) treatment measured in apoptosis protein arrays. Double dot blots represent duplicated antibody probes and broken line shows relative TRAIL-R2 expression in the untreated controls.

B. Strong expression of TRAIL-R2 protein in the tumor cell membranes (Alexa564, red fluorescence) at 8 h post-treatment (upper row) compared to the untreated tumors of the opposite legs (lower row). Areas in rectangles are highlighted in insets at higher magnification (middle column). In the left column, lines surrounding areas where signal intensity exceeds the standard positivity threshold (masked area) measured with the HistoQuant software (right column). Relative mask areas (rMA) are calculated by dividing the means of MAs by the means of the whole areas. Bar indicates 50 μm in the left column, 15 μm in the middle column and 10 μm in the right column. C. Graph showing significantly increased rMA values (**p<0.01) of TRAIL-R2 protein expression in the treated (black columns) compared to the untreated tumors (grey columns) at both 8 h and 14 h post-treatment.

FIG. 18 shows the immunfluorescent detection of HSP70
A) the expression of HSP70 14 h post treatment with radiofrequency waves using capacitive coupling in a condenser arrangement;
B) the release of HSP70 to the extracellular matrix 72 h post treatment with radiofrequency waves using capacitive coupling in a condenser arrangement.

Figure 19:
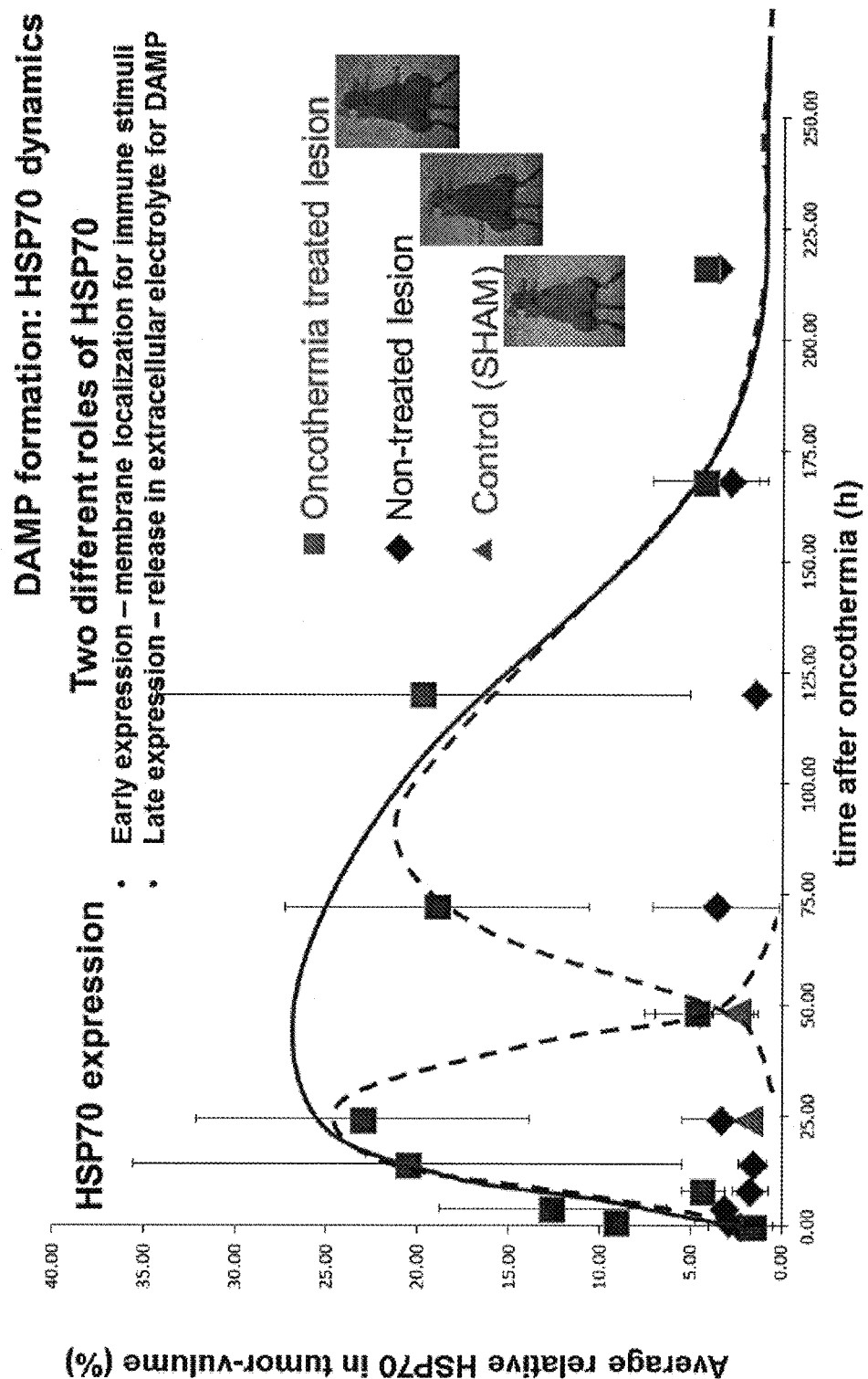
FIG. 19 shows the HSP70 dynamics during the DAMP formation.
Figure 20:
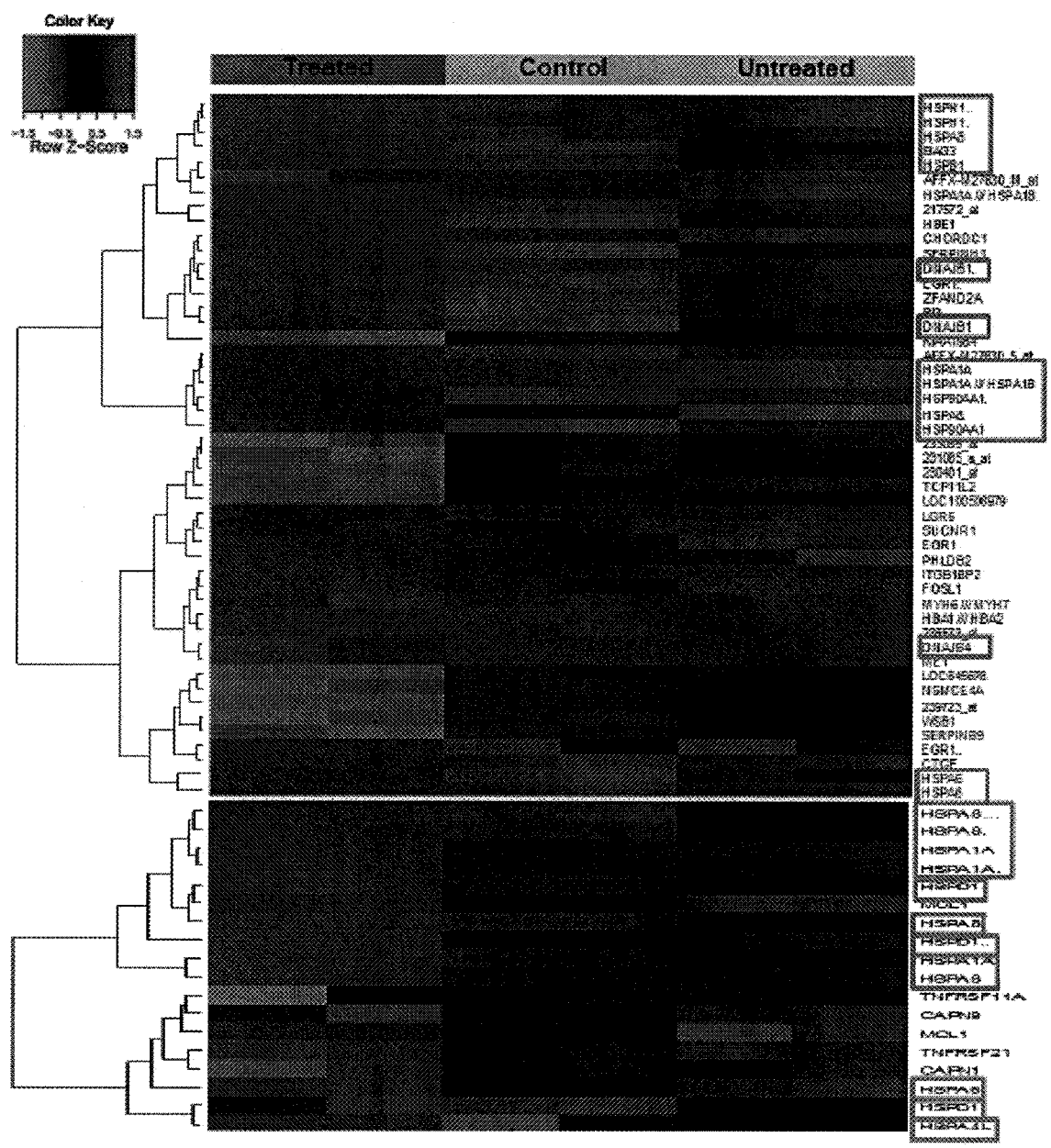
FIG. 20 shows the analysis of part of the transcript of human genome.

FIG. 19 shows the HSP70 dynamics during the DAMP formation. The complete time history of HSP70 is summarized and two independent developments could be observed:
the first development is over after 48 h from treatment with radiofrequency waves using capacitive coupling, and is connected to the direct HSP70 heat-induction;
the second development start afterwards, contributing to the immunogenic cell-death as part of DAMP FIG. 20 The gene-chip of human genome has 6500 genes and their 47000 transcripts were analyzed 4 h after-treatment with radiofrequency waves using capacitive coupling.

Figure 21:
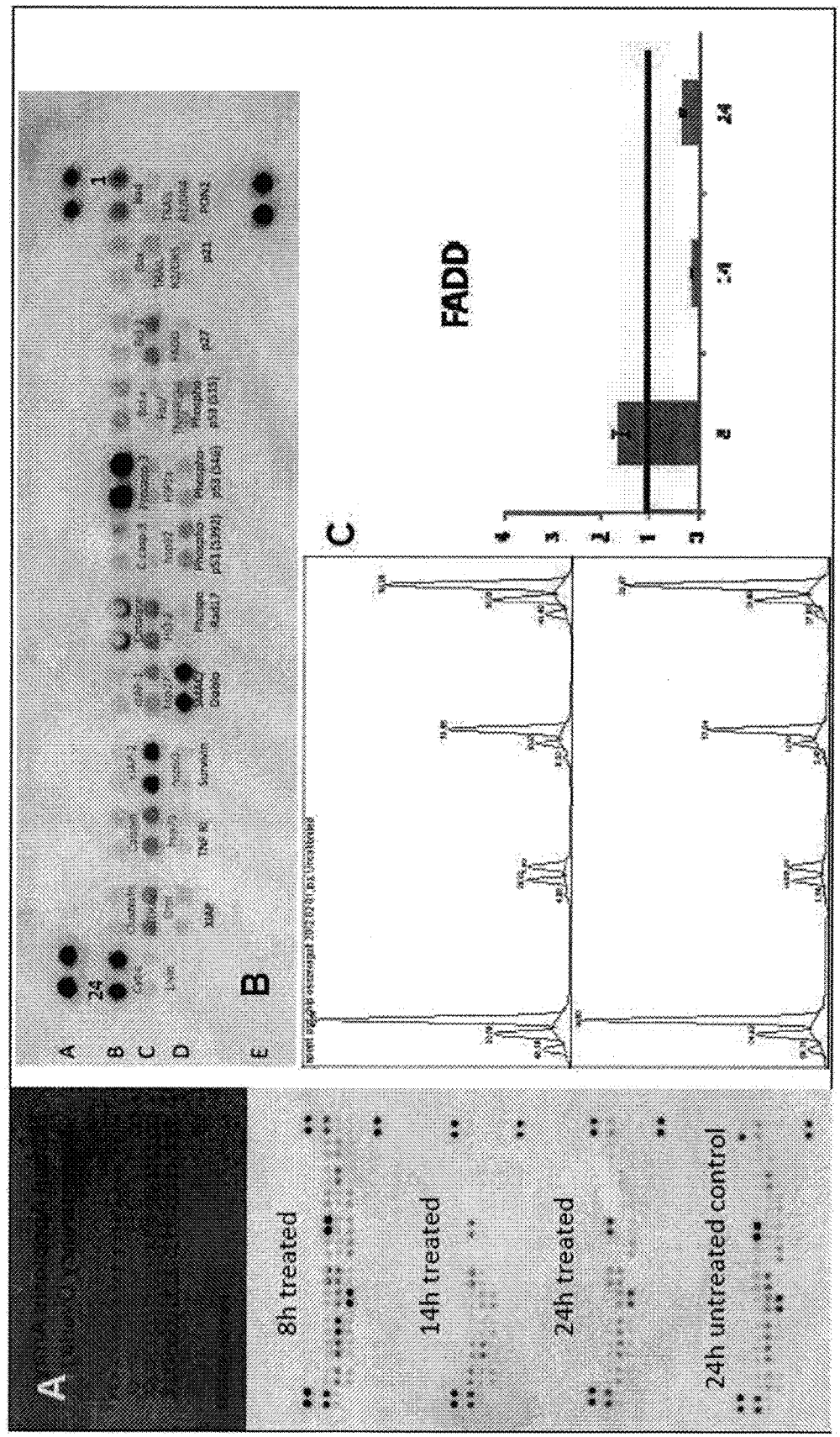
FIG. 21 is a scheme of the Proteome Profiler™ Human Apoptosis array kit analysis.

FIG. 21 shows the scheme of the Proteome Profiler™ Human Apoptosis array kit analysis: A. measured samples on the array chip; B. examined proteins on the array; C. quantitative method for protein expression level analysis.

Figure 22:
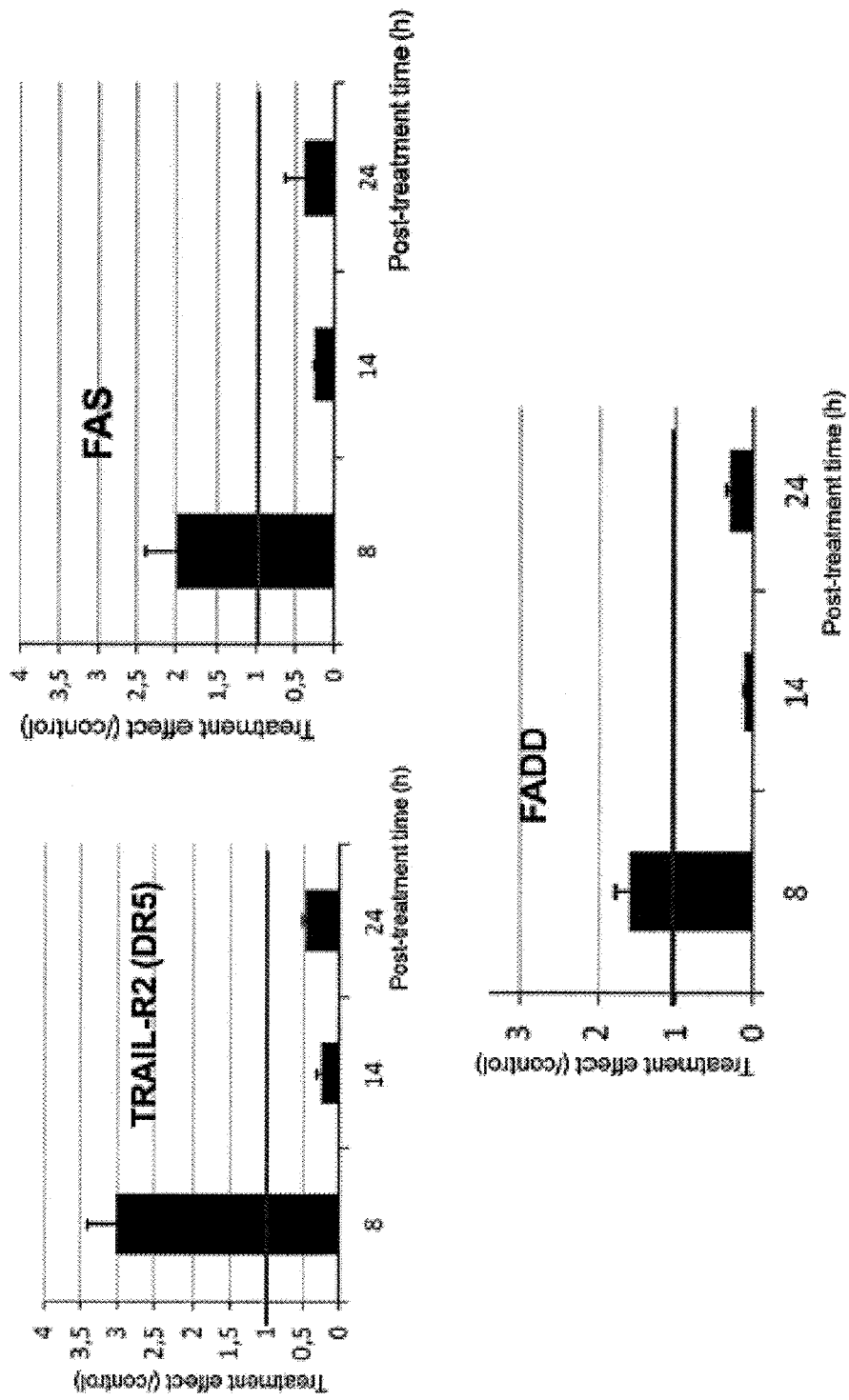
FIG. 22 shows the effect of the treatment with radiofrequency waves on the expression of proteins involved in death inducing pathways.

FIG. 22 shows the effect of the treatment with radiofrequency waves on the expression of proteins involved in death inducing pathways. These results constitute further evidences for the realization of the cell-membrane associated apoptotic pathway.

Figure 23:
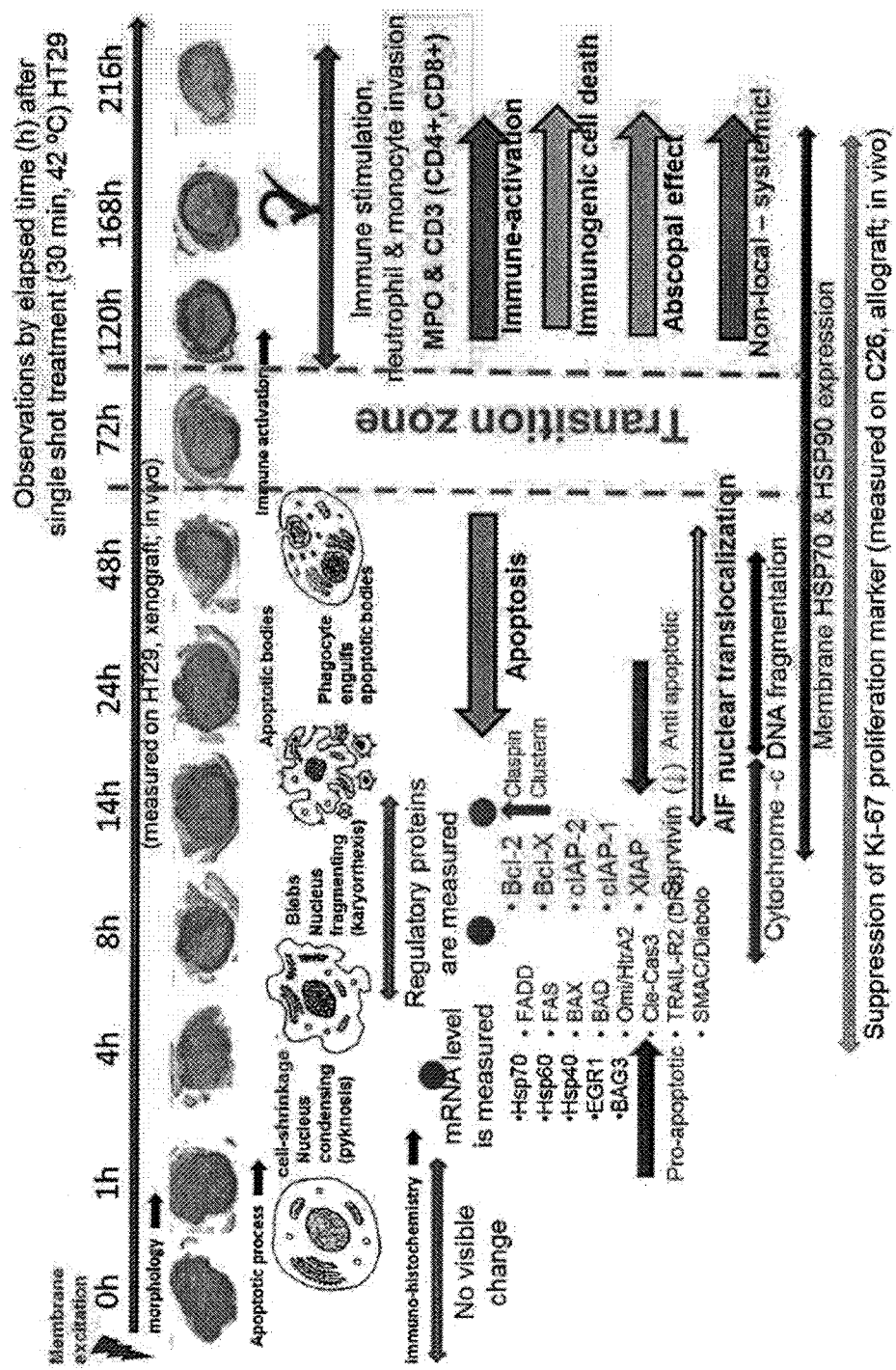
FIG. 23 shows the observations by elapsed time (h) after single shot treatment.

FIG. 23 sums up the observations by elapsed time (h) after single shot treatment with radiofrequency waves using capacitive coupling (30 min, 42° C.) on HT29 cells. The most important proteins induced by the treatment were identified. As displayed, apoptosis finished after 48 hours post-treatment, and after a transition zone, immune reactions were observed.

Figure 24:
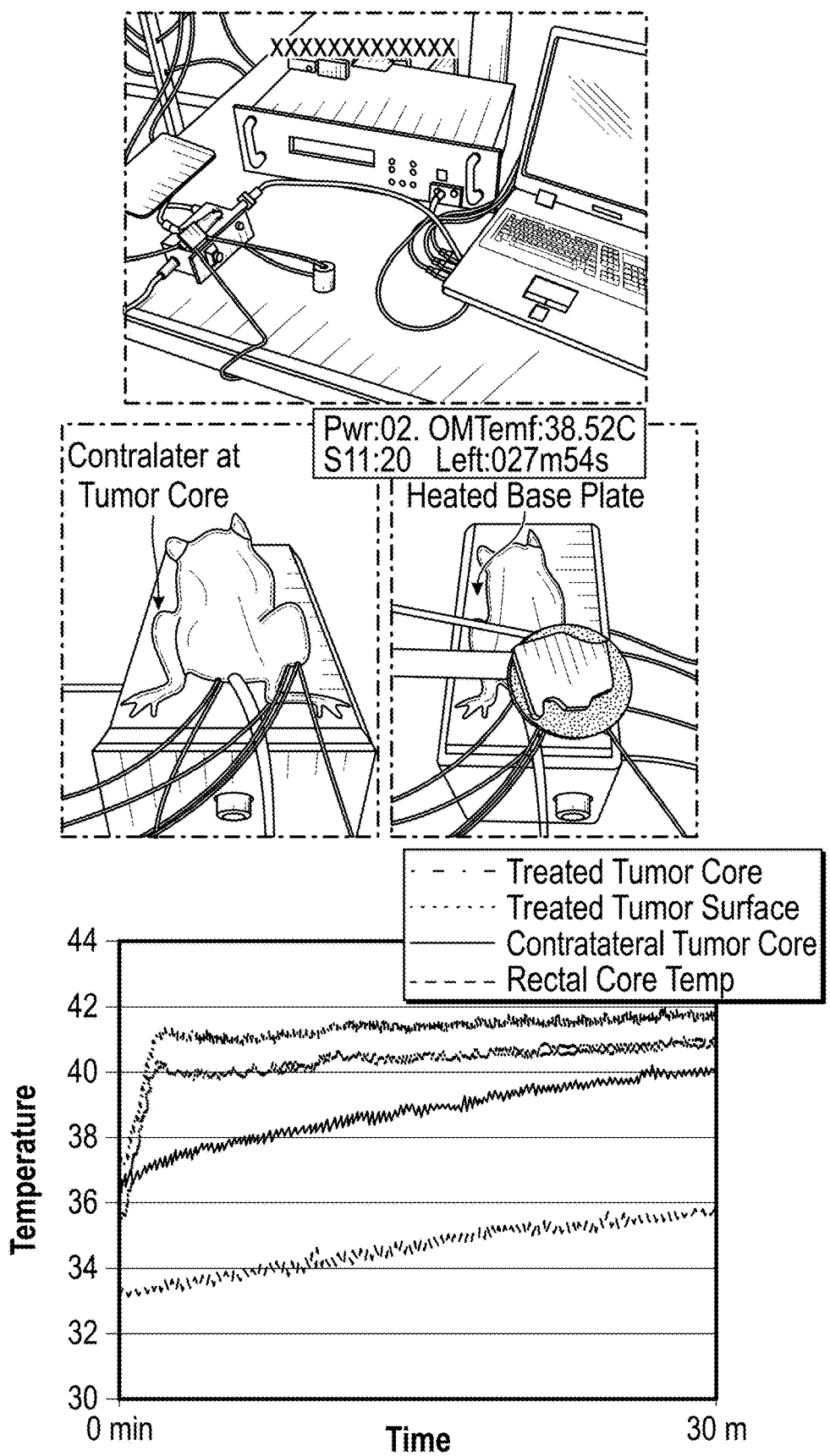
FIG. 24 shows the measurement set-up and the temperature pattern of the experiment.

FIG. 24 shows the measurement set-up and the temperature pattern of the experiment.

Figure 25:
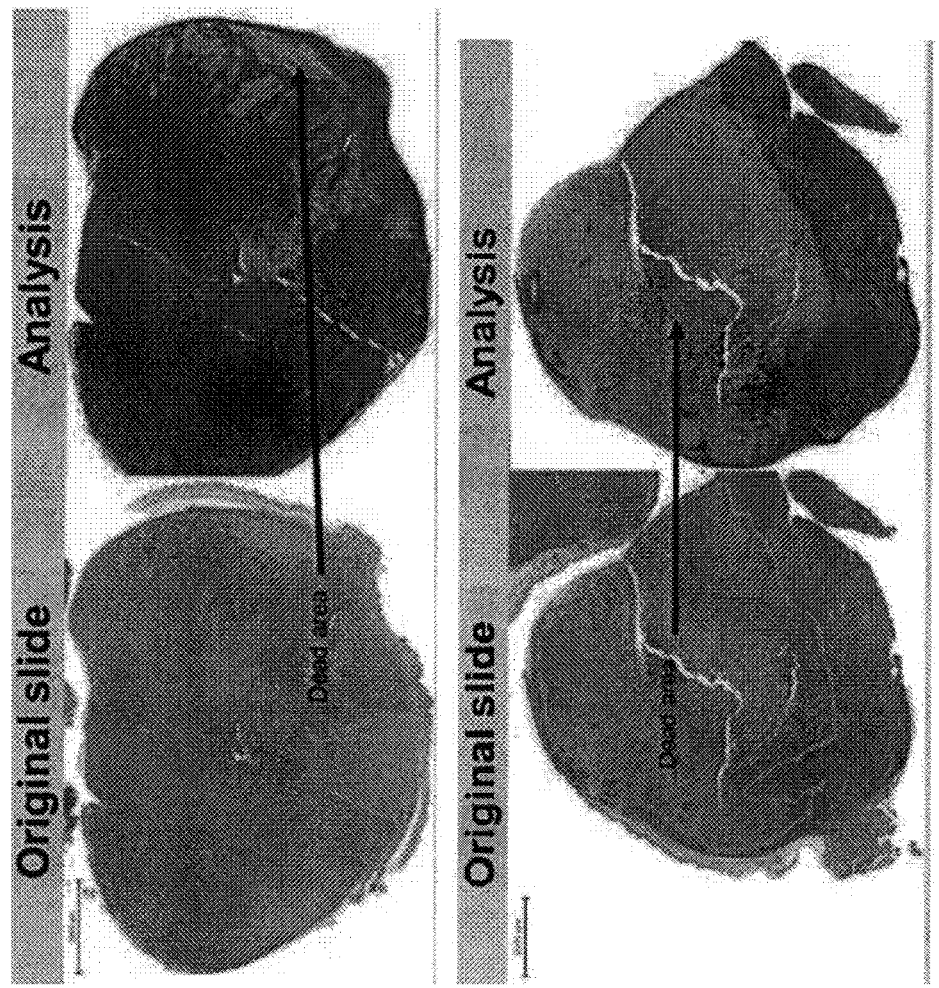
FIG. 25 shows examples of evaluation of the samples.

FIG. 25 shows examples of evaluation of the samples.

Figure 26A:
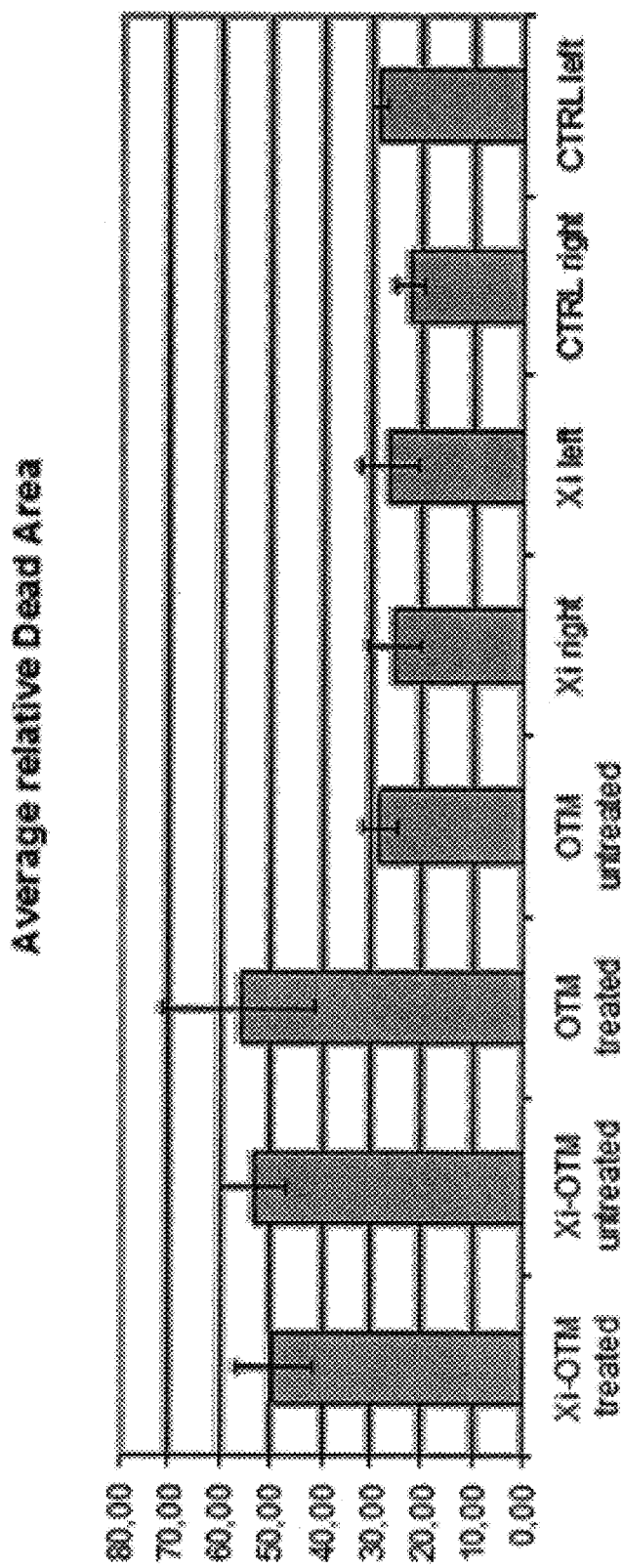
FIG. 26A shows the average relative dead area of the tumors in the study groups.
Figure 26B:
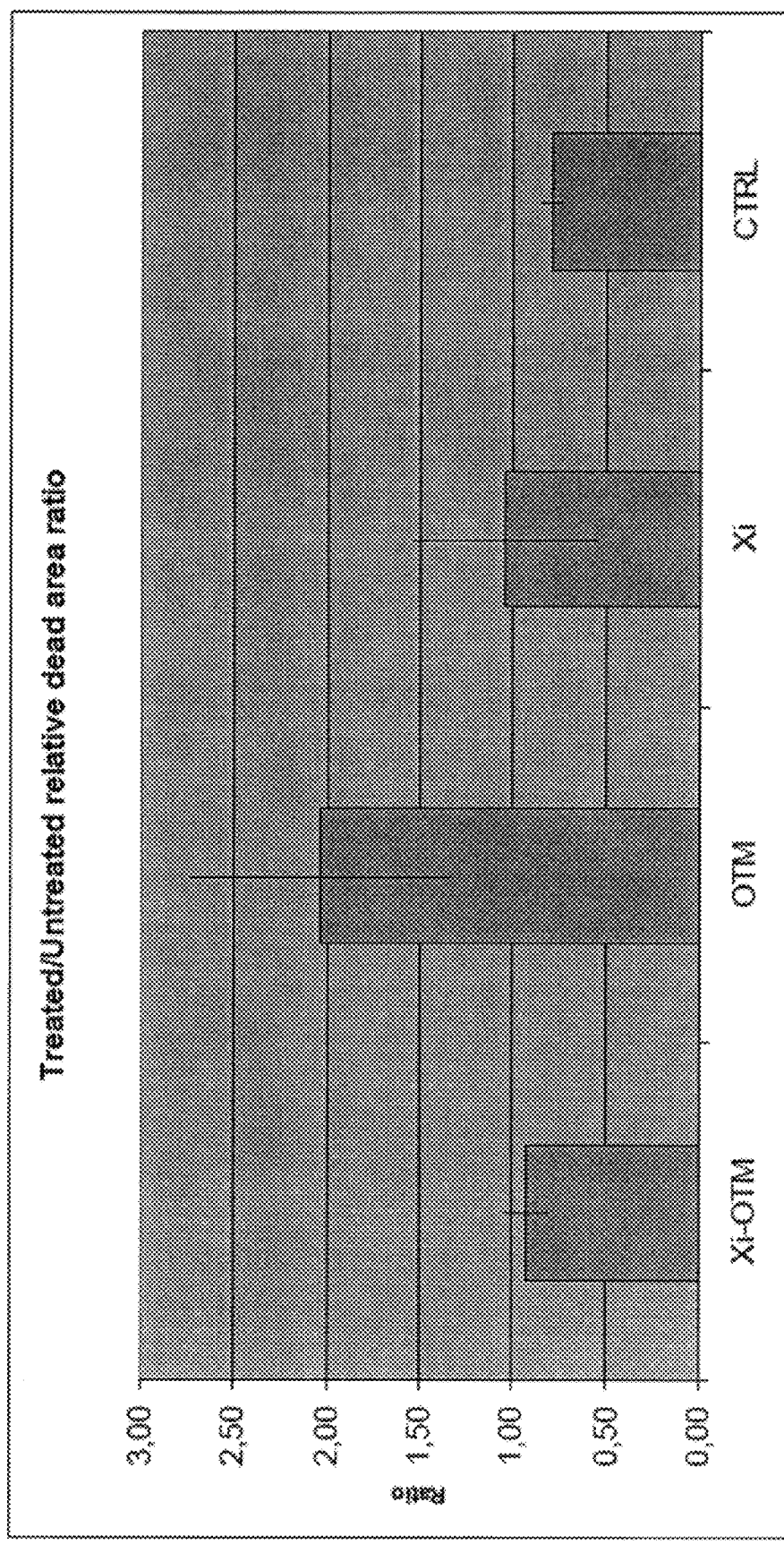
FIG. 26B shows treated/untreated relative dead area ratio of the tumors in the study groups.

FIG. 26 shows evidence for the typical abscopal effect provided by the present invention.
A. The average relative dead area of the tumors in the study groups.
B. The treated/untreated relative dead area ratio of the tumors in the study groups Thus, the combined administration of Xiao-Aiping and radiofrequency waves using capacitive coupling (Xi-OTM) had beneficial effect on both tumors, while only one tumor was treated with radiofrequency waves using capacitive coupling (Oncothermia-OTM). Treatment with radiofrequency waves using capacitive coupling (Oncothermia-OTM treatment) was effective only on the tumor, which was treated. Treatment with Xiao-Aiping (Xi) has no results compared to the control (CTRL).

Figure 27:
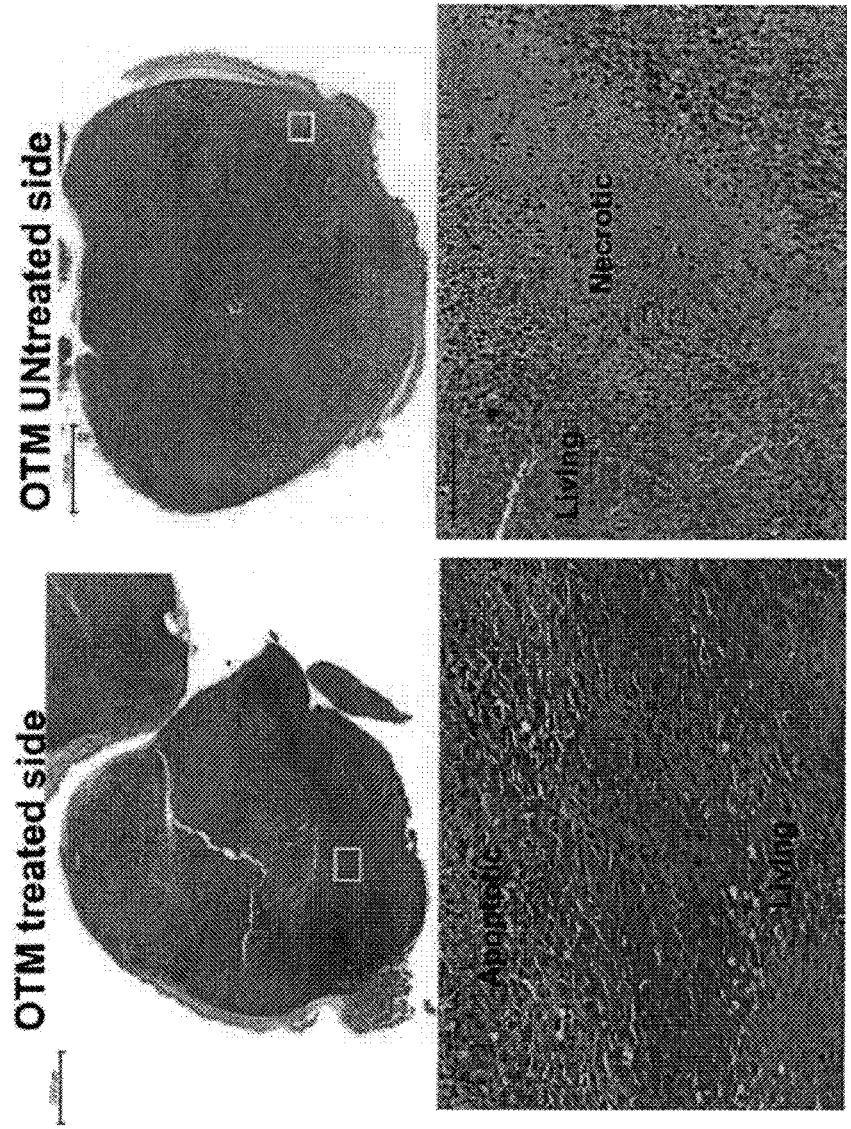
FIG. 27 shows the HE stained tumor samples from the OTM alone treated group.

FIG. 27 shows the HE stained tumor samples from the OTM alone treated group.

Figure 28:
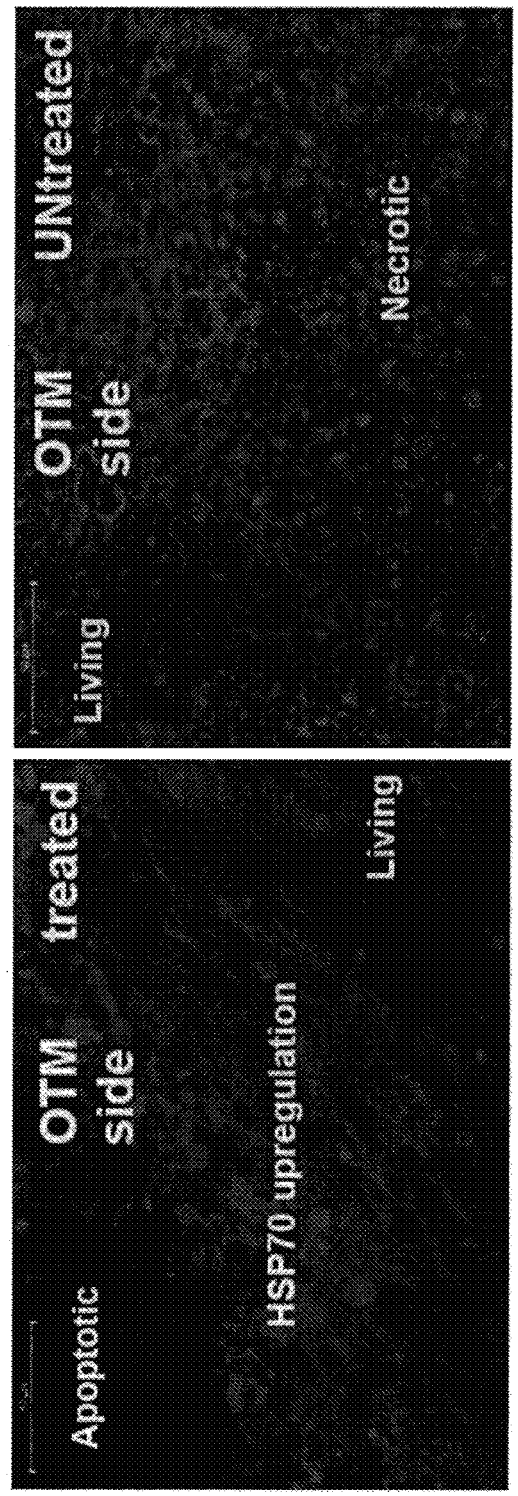
FIG. 28 shows IHCH detection of HSP70 in the tumor samples from the oncothermia alone treated group.

FIG. 28 shows IHCH detection of HSP70 (red) in the tumor samples from the oncothermia alone treated group. (cell nuclei: blue)

Figure 29:
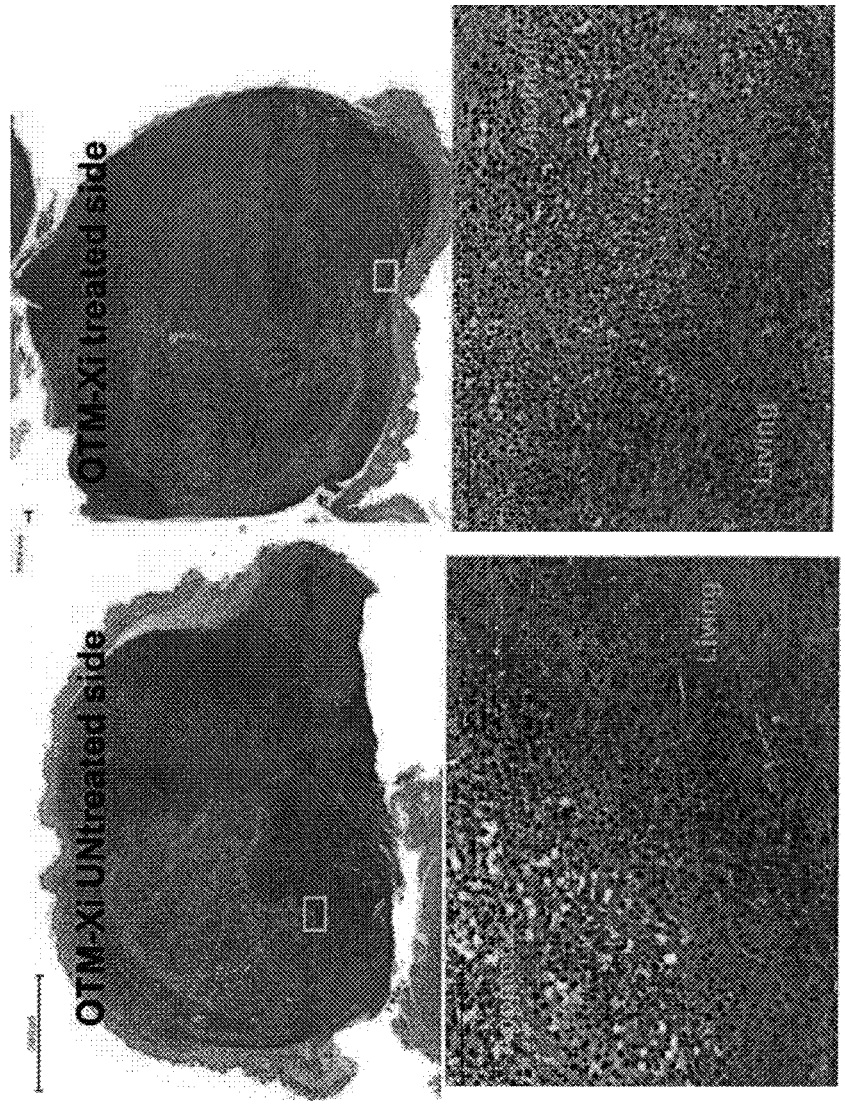
FIG. 29 shows the HE stained tumor samples from the OTM+Xi treated group.

FIG. 29 shows the HE stained tumor samples from the OTM+Xi treated group

Figure 30:
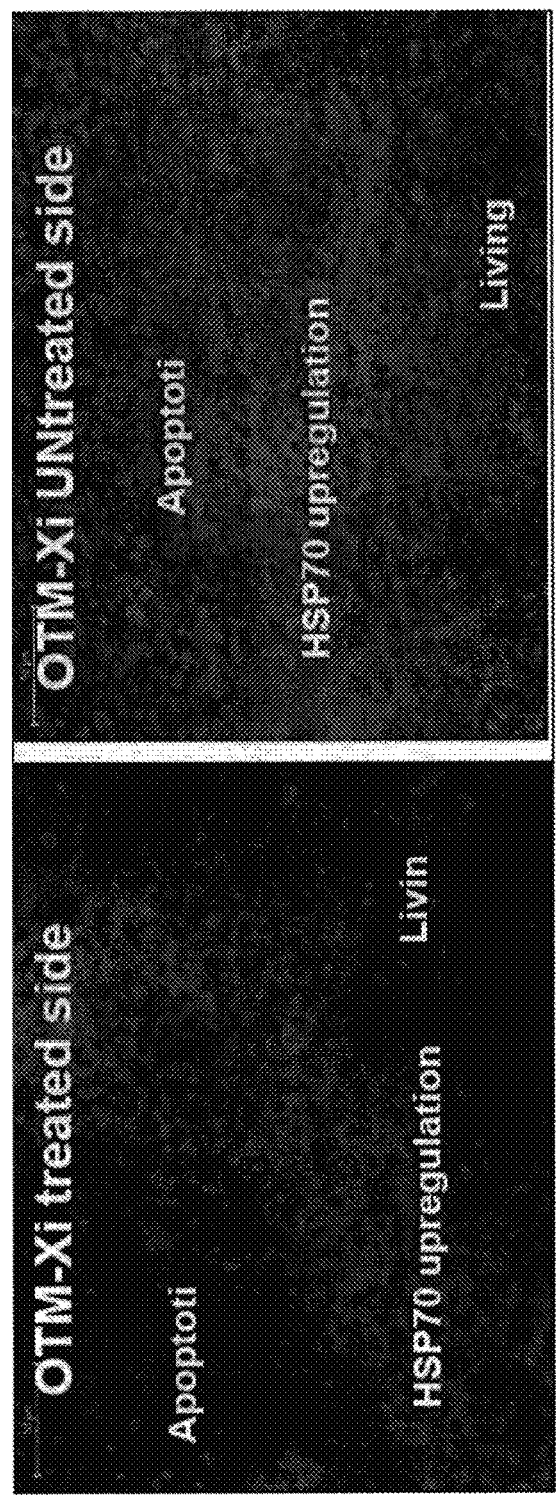
FIG. 30 shows IHCH detection of HSP70 in the tumor samples from the OTM+Xi treated group.

FIG. 30 shows IHCH detection of HSP70 (red) in the tumor samples from the OTM+Xi treated group. (cell nuclei: blue)

Figure 31:
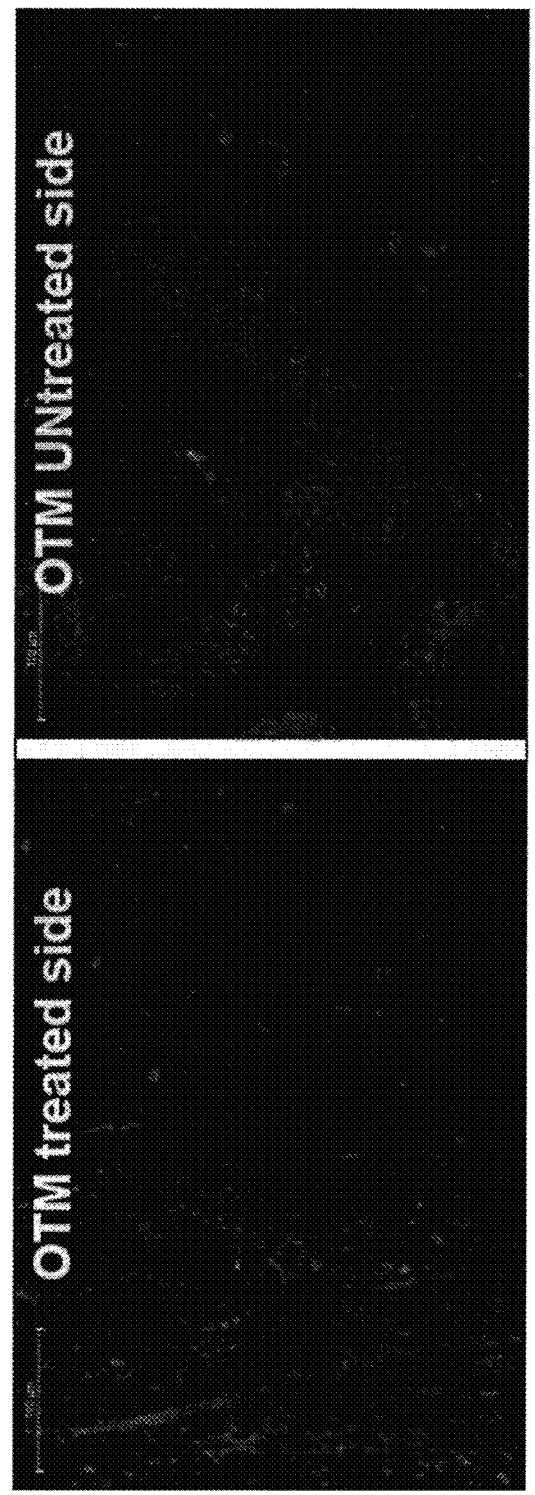
FIG. 31 shows IHCH detection of CD3+ T cells and TUNEL reaction in the tumor samples from the oncothermia alone treated group.

FIG. 31 shows INCH detection of CD3+ T cells (red), and TUNEL reaction (green) in the tumor samples from the oncothermia alone treated group. (cell nuclei: blue) (Colocalization of nucleus and TUNEL reaction means programmed cell death)

Figure 32:
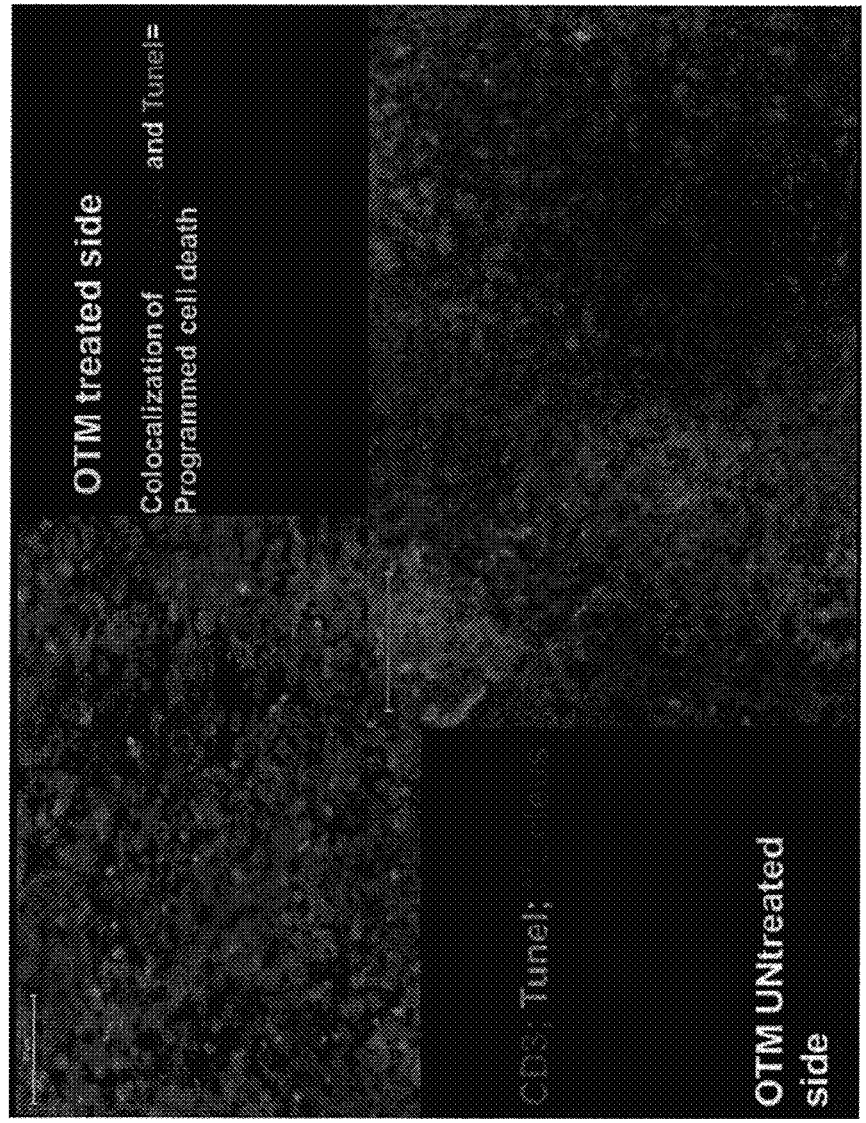
FIG. 32 shows the colocalization of nucleus and the nucleic acid fragmentation (TUNEL) induced by the treatment.

FIG. 32 shows the colocalization of nucleus and the nucleic acid fragmentation (TUNEL) induced by the treatment with radiofrequency waves using capacitive coupling (oncothermia treatment) as prove of programmed cell death. The blue is standard DAPI staining (cell nuclei) and the green is TUNEL FITC.

Figure 33:
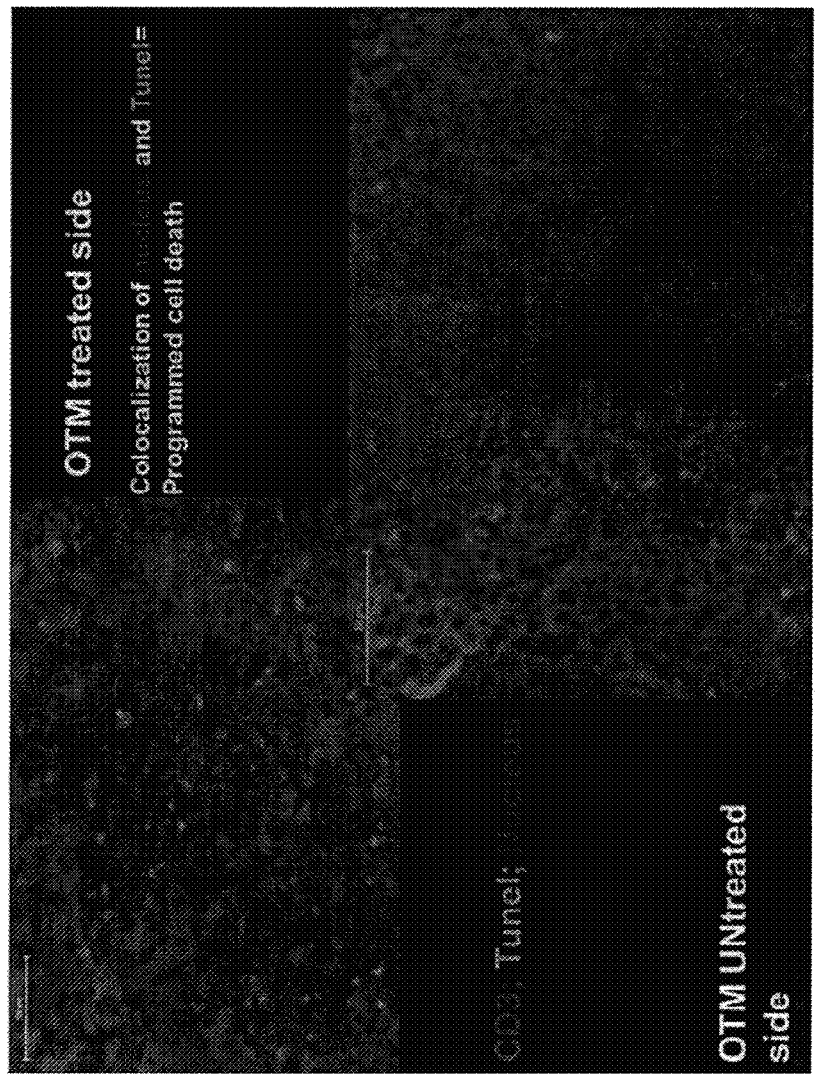
FIG. 33 shows the colocalization of nucleus and the nucleic acid fragmentation (tunnel) induced by the treatment.

FIG. 33 shows the colocalization of nucleus and the nucleic acid fragmentation (tunnel) induced by the treatment with radiofrequency waves using capacitive coupling (oncothermia treatment) as proves of programmed cell death. The blue is standard DAPI staining (cell nuclei) and the green is TUNEL FITC.

Figure 34:
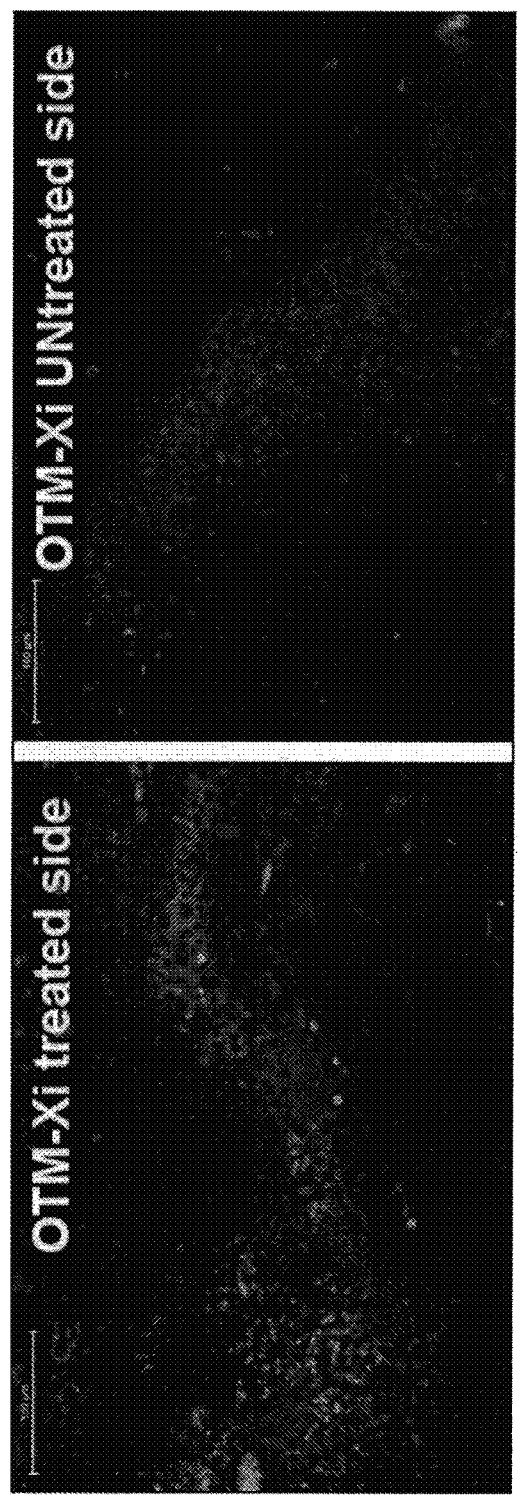
FIG. 34 shows IHCH detection of CD3+ T cells (red), and TUNEL reaction (green) in the tumor samples from the OTM+Xi alone treated group.

FIG. 34 shows INCH detection of CD3+ T cells (red), and TUNEL reaction (green) in the tumor samples from the OTM+Xi alone treated group. (cell nuclei: blue) (Colocalization of nucleus and TUNEL reaction means programmed cell death)

Figure 35:
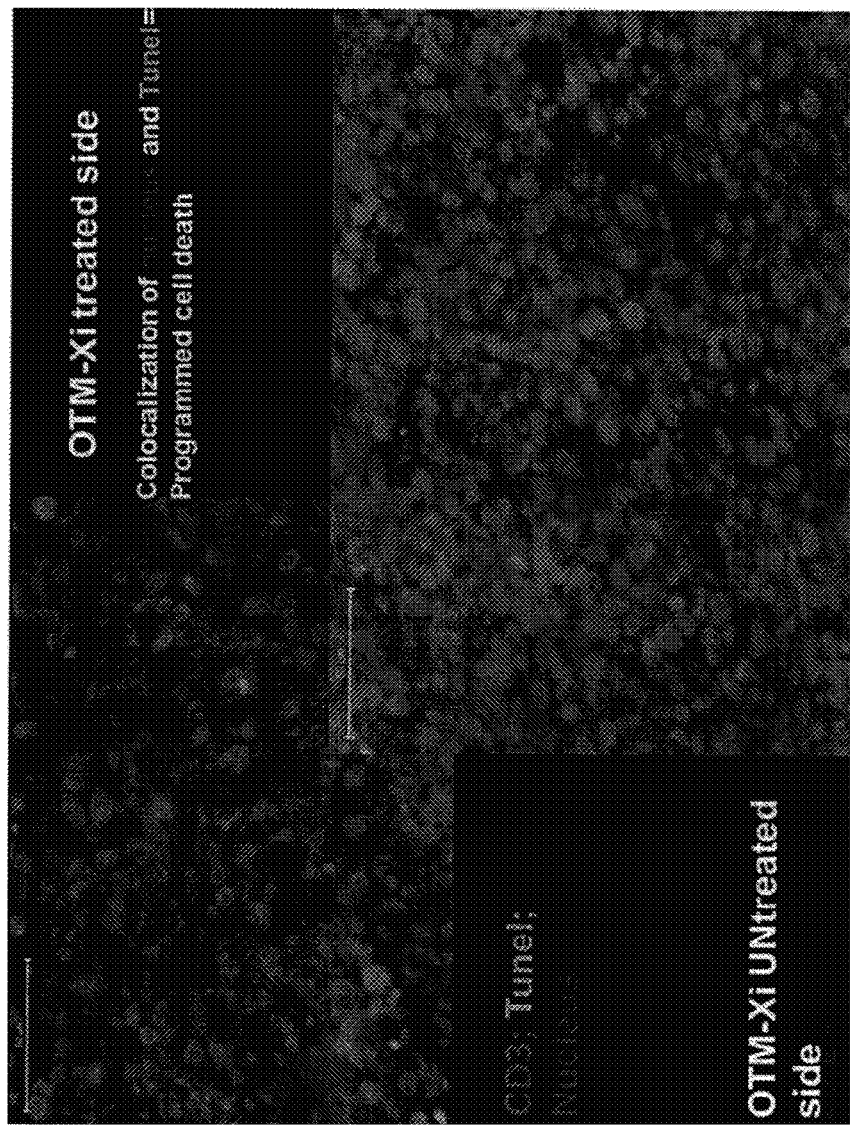
FIG. 35 shows the colocalization of nucleus and the nucleic acid fragmentation (tunnel) induced by the treatment.

FIG. 35 shows the colocalization of nucleus and the nucleic acid fragmentation (tunnel) induced by the treatment with radiofrequency waves using capacitive coupling (oncothermia treatment) as proves of programmed cell death. The blue is standard DAPI staining (cell nuclei) and the green is TUNEL FITC.

Figure 36:
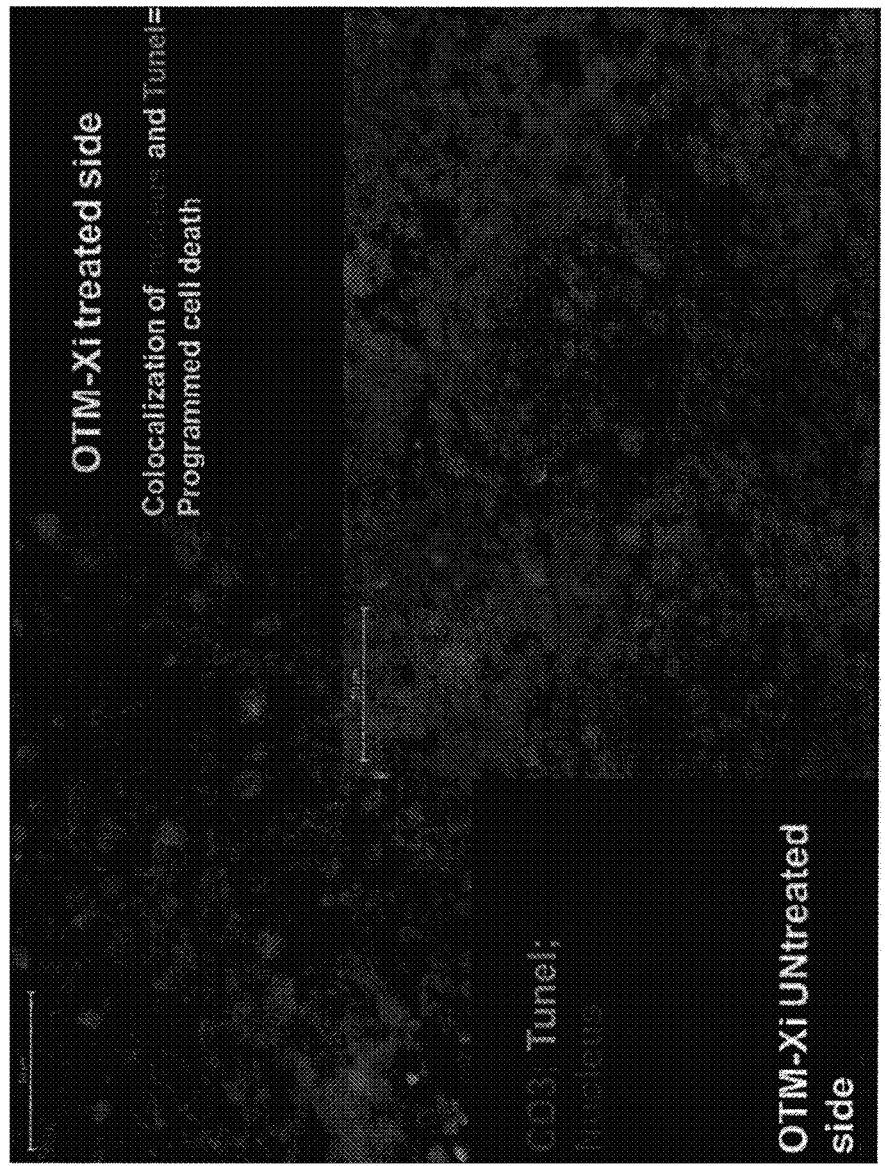
FIG. 36 shows the colocalization of nucleus and the nucleic acid fragmentation (tunnel) induced by the treatment.

FIG. 36 shows the colocalization of nucleus and the nucleic acid fragmentation (tunnel) induced by the treatment with radiofrequency waves using capacitive coupling (oncothermia treatment) as proves of programmed cell death. The blue is standard DAPI staining (cell nuclei) and the green is TUNEL FITC.

Figure 37:
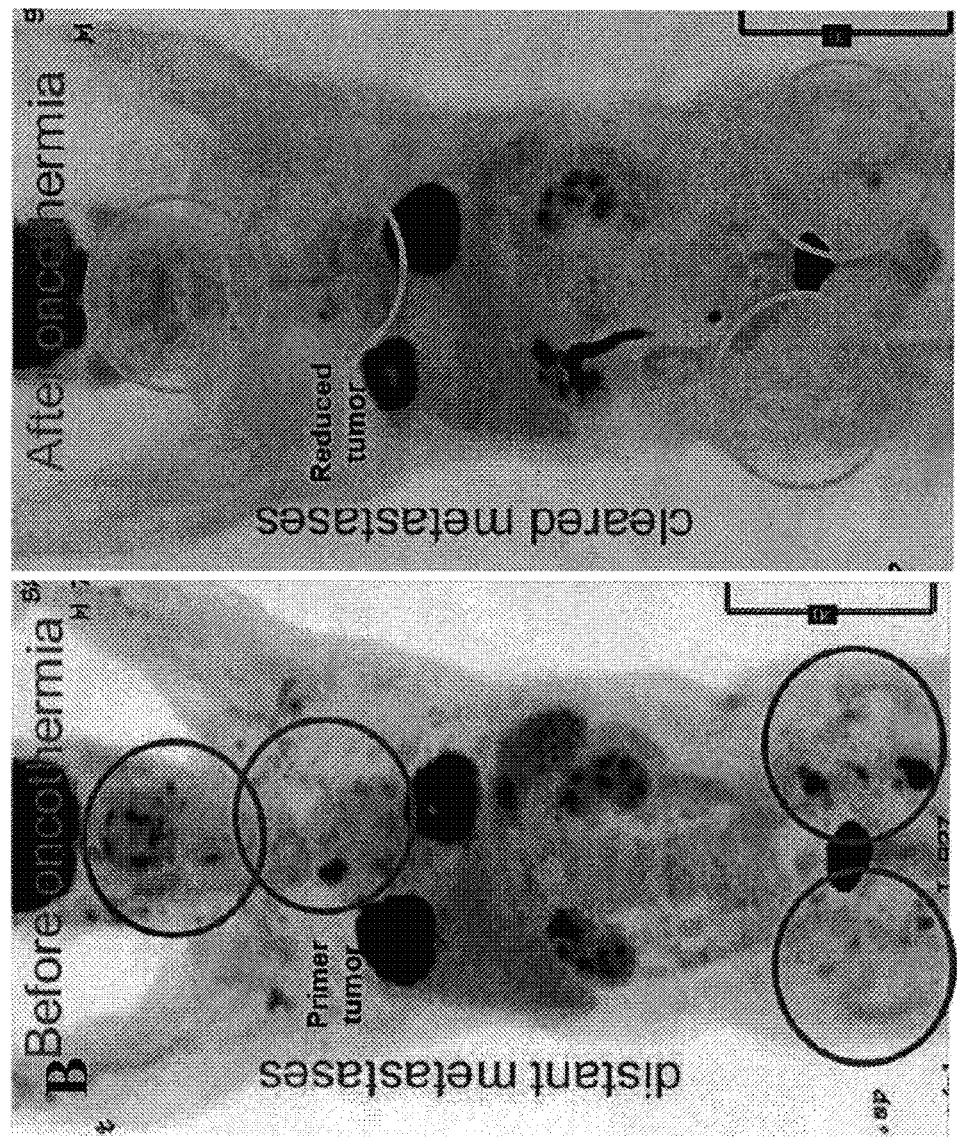
FIG. 37 shows the results obtained by applying the vaccination according to the present invention to a non-small-lung cancer patient.

FIG. 37 shows the results obtained by applying the vaccination according to the present invention to a non-small-lung cancer patient (male, 72 years old). The local tumor was treated by amplitude modulated radiofrequency waves using capacitive coupling and Leukine® as immune-stimulator was applied in parallel. The primary tumor started to shrink, while the metastases disappeared.

Figure 38:
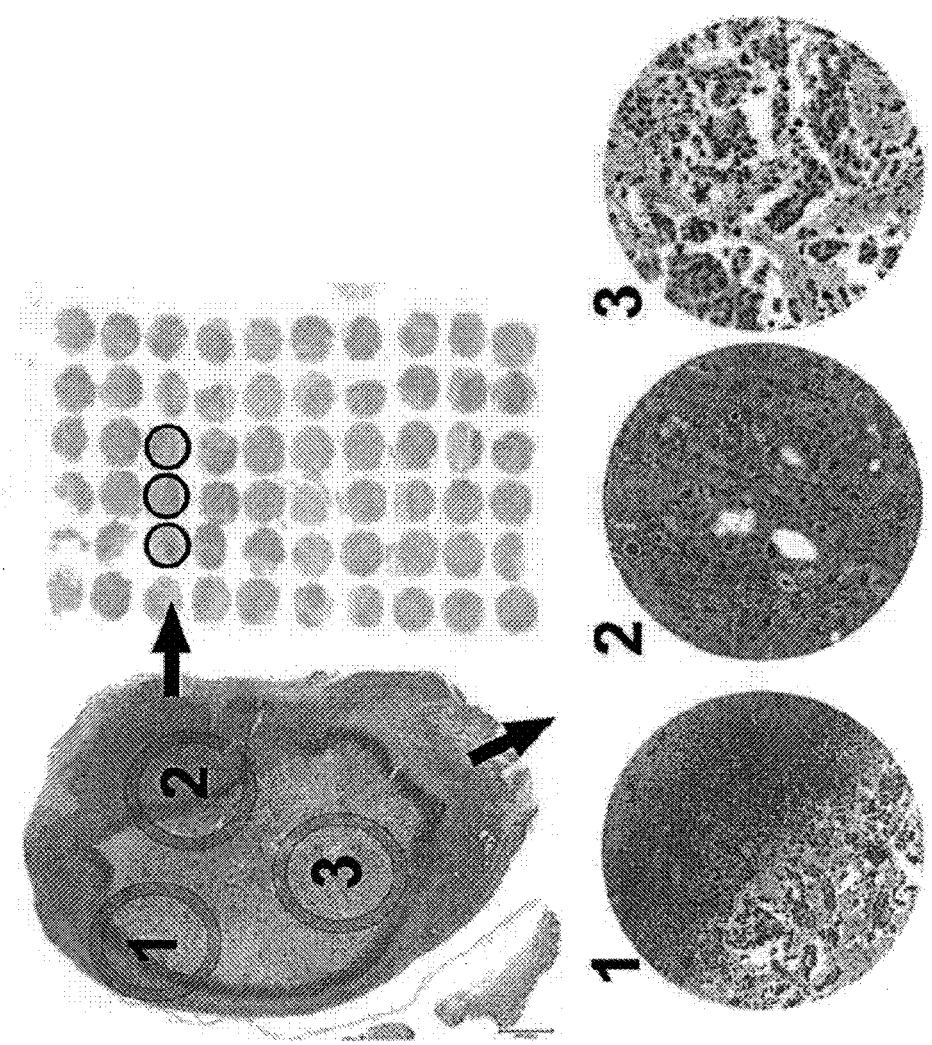
FIG. 38 shows a method of creating a tissue multiblock from a Formalin-Fixed, Paraffin-Embedded tumor sample.

FIG. 38 shows a method of creating a tissue multiblock from a Formalin-Fixed, Paraffin-Embedded tumor sample: 2 mm diameter cores selected from the damaged and the intact tumor border (1 and 2) and from the damaged tumor center (3) were taken of each sample.

Figure 39:
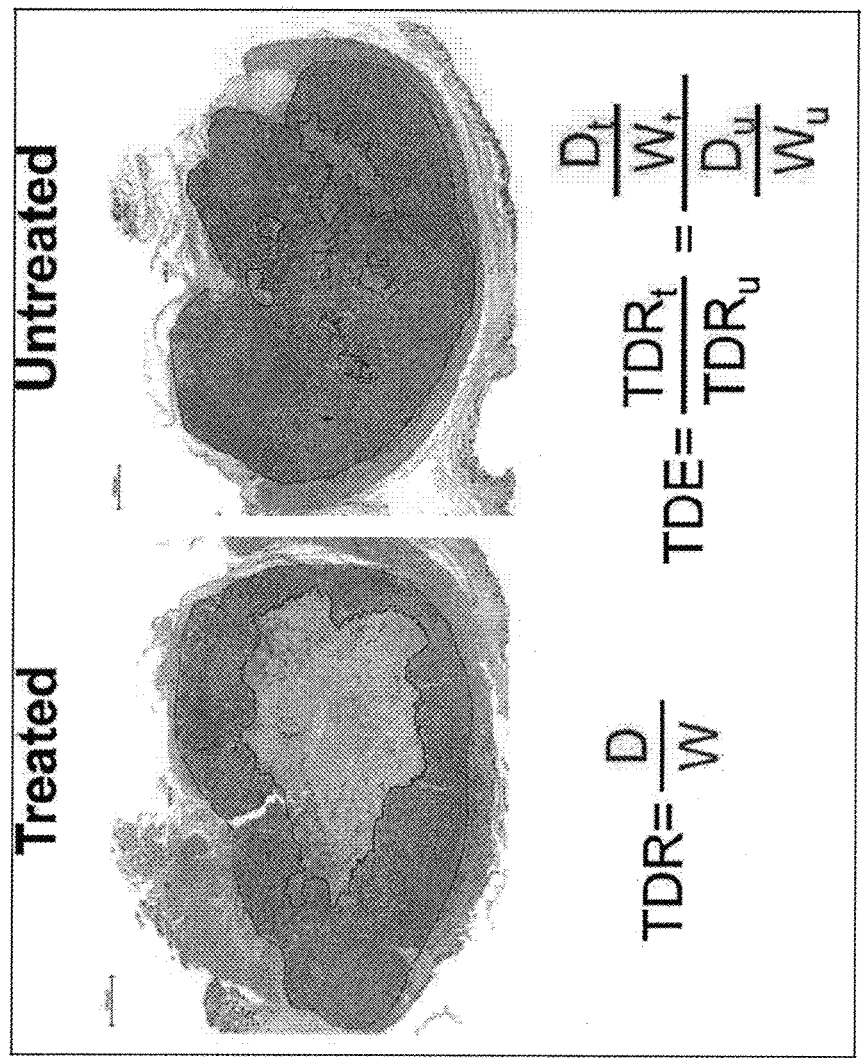
FIG. 39 shows the scheme of the method of calculating TDR and TDE using quantitative digital microscopy analysis.

FIG. 39 shows the scheme of the method of calculating TDR and TDE using quantitative digital microscopy analysis: Damaged tumor areas (labeled D and circled in red; inner circles) and the whole tumor areas (labeled W and circled in blue; outer circle) are measured with software. Tumor destruction ratio (TDR) is calculated by dividing the D by the W values both in the treated (t) and untreated (u) tumors. Tumor destruction efficiency (TDE) is a correlation between TDR values of the treated and untreated tumors.

FIG. 40 shows A. the qualitative histomorphological appearance of the oncothermia (radiofrequency waves using capacitive coupling in a condenser arrangement) treatment induced tumor destruction 24 h after a single shot treatment; B. the result of the quantitative analysis of the tumor destruction ratio (TDR): graph showing significantly higher TDR values (*p<0.05) in treated (black boxes) than in untreated (grey boxes) tumors; C. the result of the quantitative analysis of the oncothermia (radiofrequency waves using capacitive coupling in a condenser arrangement) treatment related tumor cell destruction (TDE): graph showing the treatment related increase of TDE values going up to a 7-fold difference at 72 h.

Figure 41:
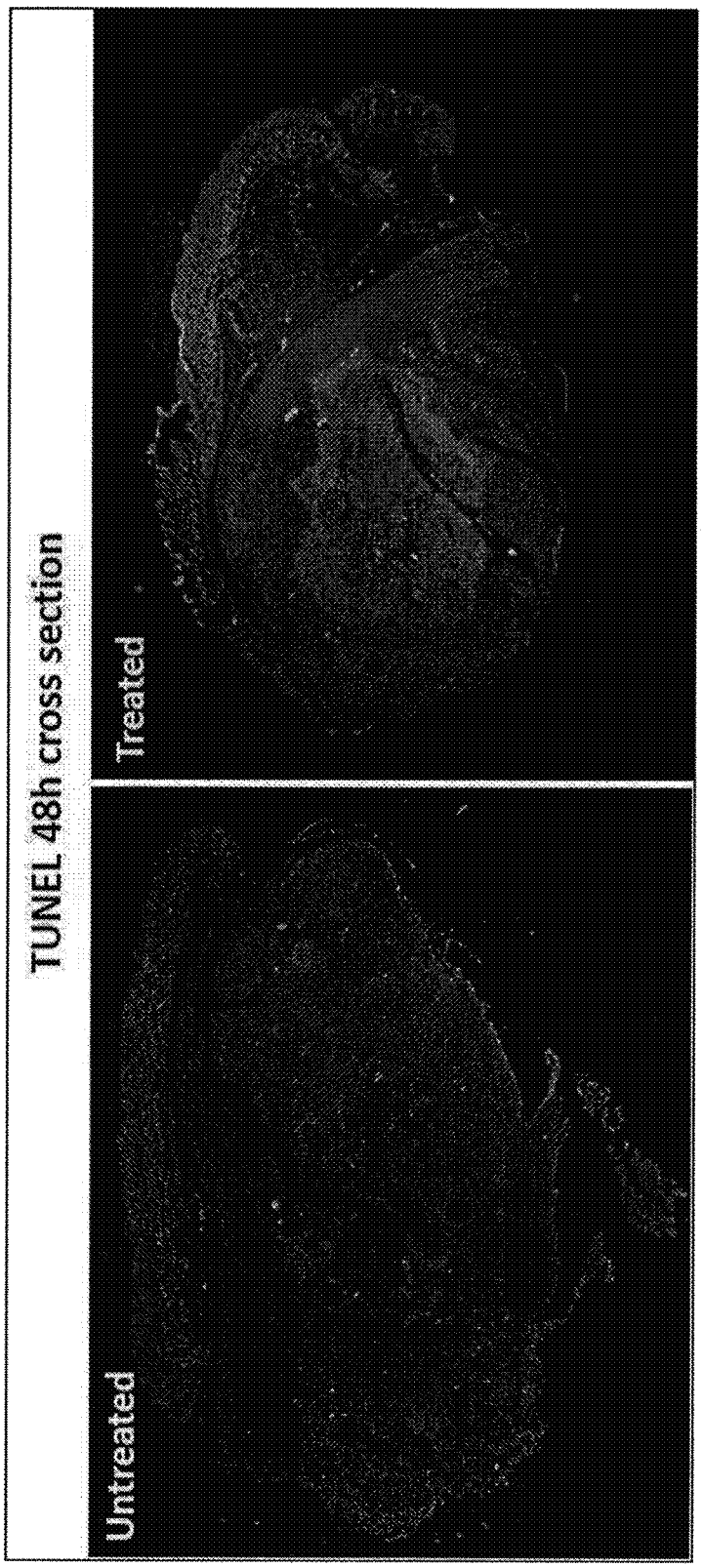
FIG. 41 is a qualitative observation of the TUNEL positivity in the whole tumor cross section 48 H after the treatment.

FIG. 41 is a qualitative observation of the TUNEL positivity in the whole tumor cross section 48 H after the treatment. Note the high TUNEL positivity at the central destructed region of the tumor.

Figure 42A:
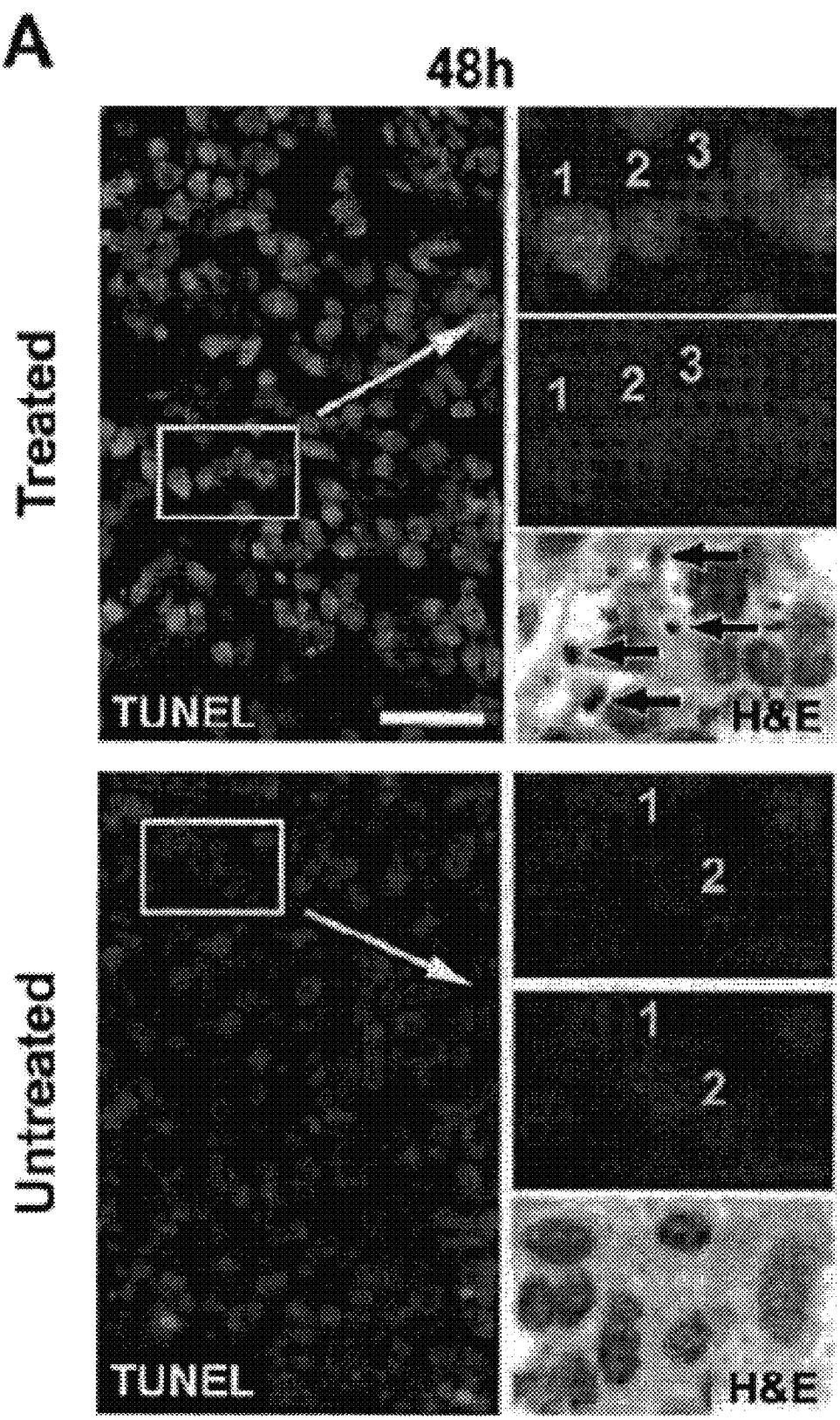
FIGS. 42A-C are a qualitative observation (at 48 h) and quantitative measurement of the TUNEL positivity and apoptotic body formation in the whole tumor cross sections after the treatment.
Figure 42B:
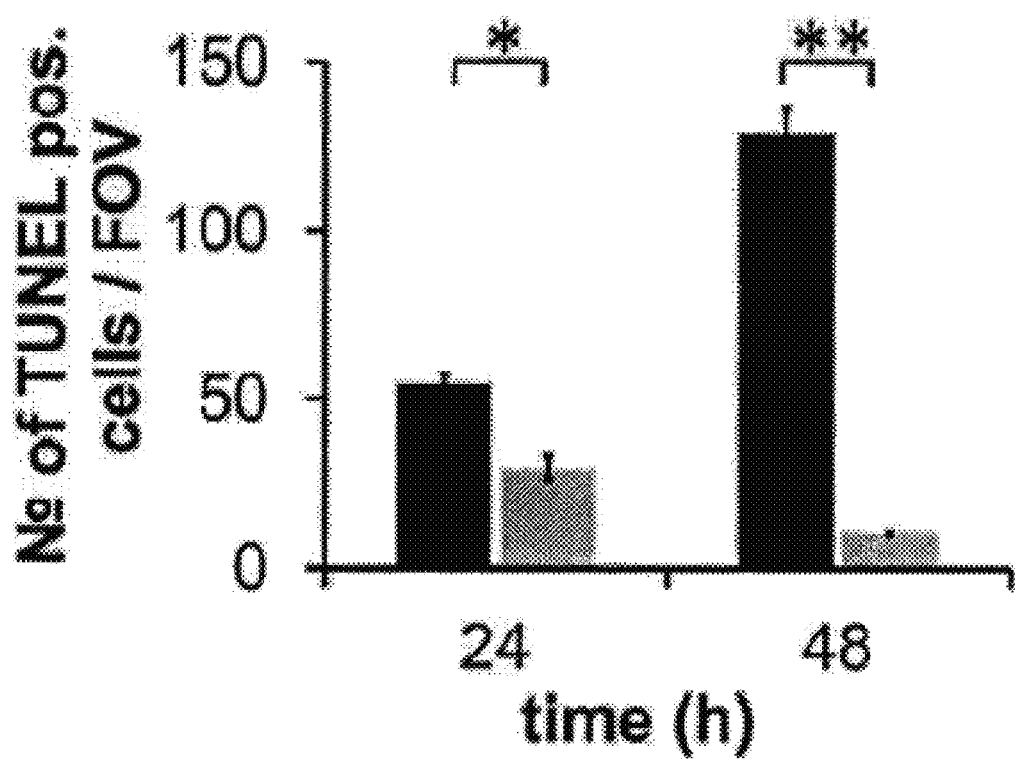
Figure 42C:
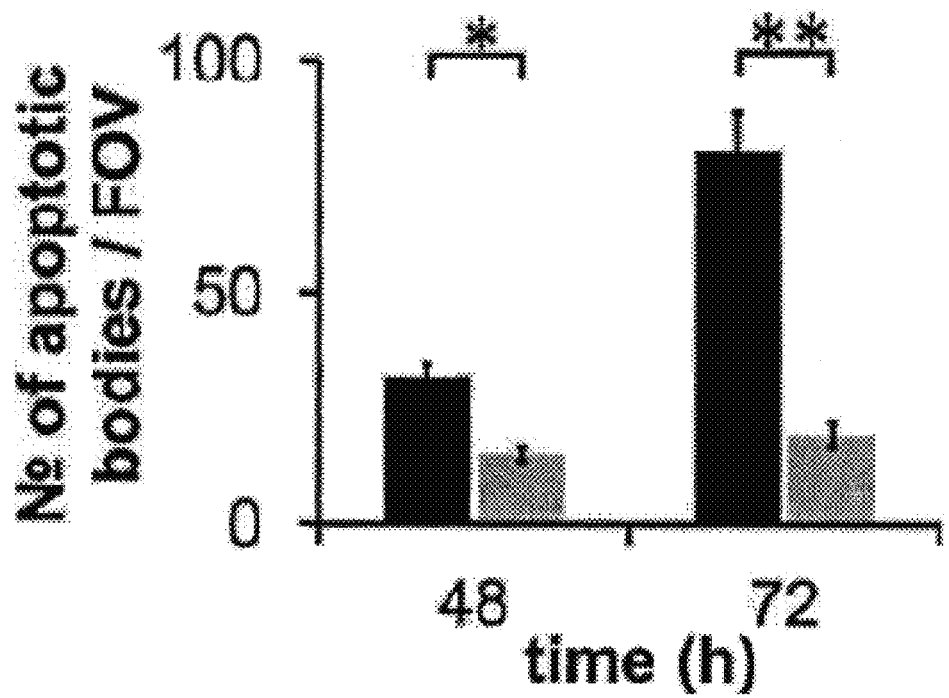

FIG. 42 is a qualitative observation (at 48 h) and quantitative measurement of the TUNEL positivity and apoptotic body formation in the whole tumor cross sections 24 h and 48 h after the treatment:

A. Significant elevation of DNA fragmentation revealed by TUNEL assay (green fluorescence in the upper picture of the cutout), nuclear shrinkage and apoptotic bodies (H&E staining; arrows in the lowest picture of the cutout) in oncothermia (radiofrequency waves using capacitive coupling in a condenser arrangement) treated (upper row) compared to untreated tumors (lower row), at 48 h post-treatment. Cutout pictures show single channel views of areas within rectangles at higher magnification. TUNEL and DAPI (blue; middle picture) double positivity verifies nuclear DNA staining in identical cells labeled 1-3. Untreated tumor cells (e.g. those labeled 1-2) show only basic green fluorescence. Bar indicates 50 μm in the left column and 15 μm in the right column.

B. Graph showing significantly increased mean number of TUNEL positive cells both at 24 h and 48 h post-treatment (black columns);

C. Graph showing significantly increased mean number of apoptotic bodies at 48 h and 72 h post-treatment (black columns) compared to the untreated controls (grey columns) (*p<0.05, **p<0.01).

Figure 43:
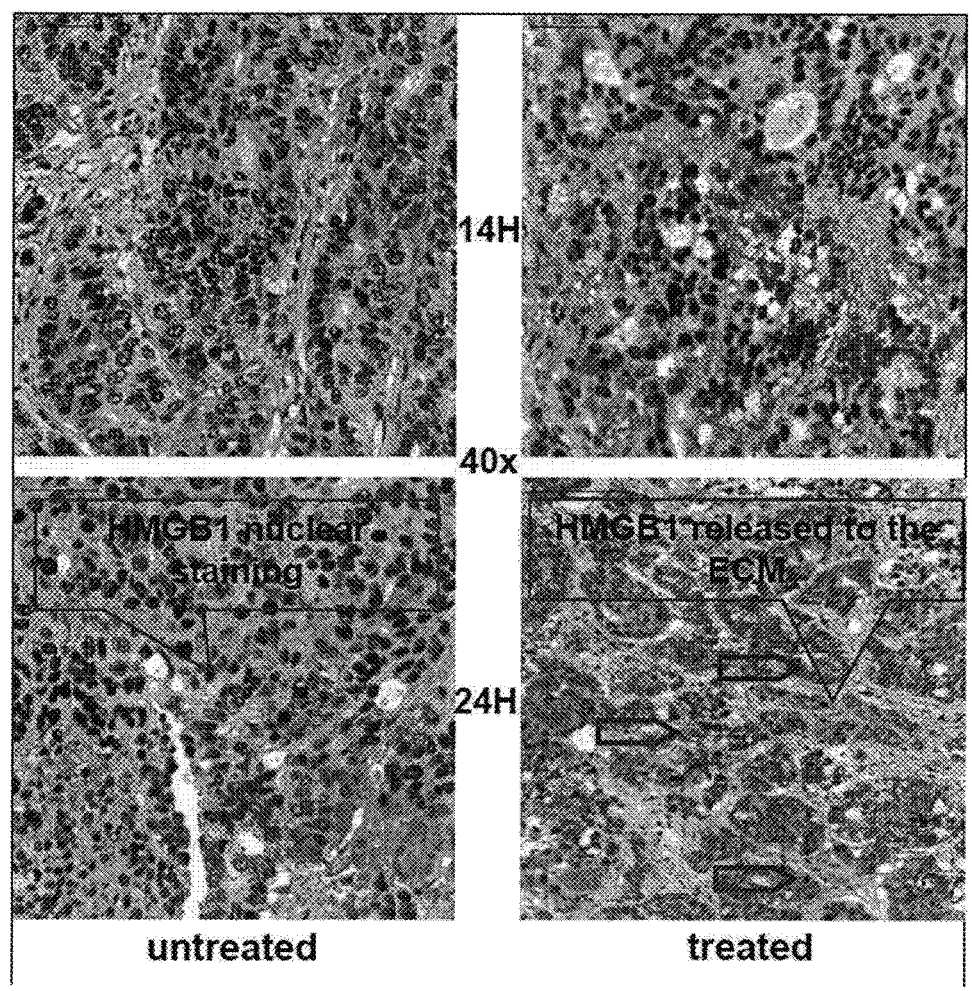
FIG. 43 shows the immunofluorescent detection of HMGB1 14 h and 24 h after the treatment.

FIG. 43 shows the immunfluorescent detection of HMGB1 14 h and 24 h after the treatment. It is clearly visible the HMGB1 is released to the extracellular matrix in oncothermia (radiofrequency waves using capacitive coupling in a condenser arrangement) treated tumors.

Figure 44A:
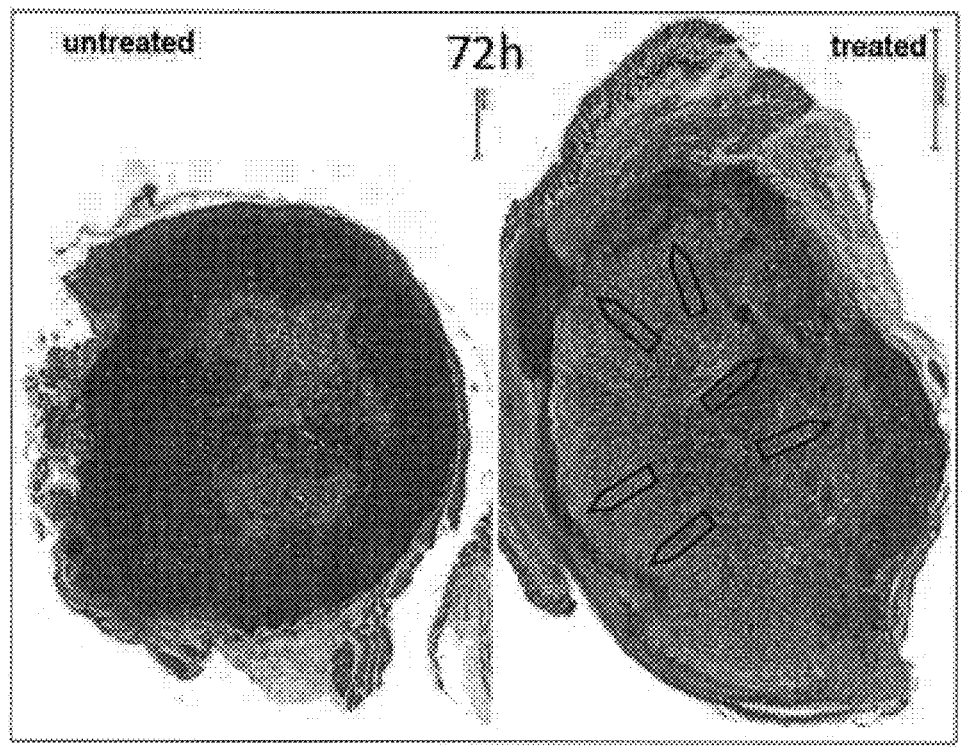
FIGS. 44A and B show HE stained whole tumor cross sections 72 h and 168 h post treatment.
Figure 44B:
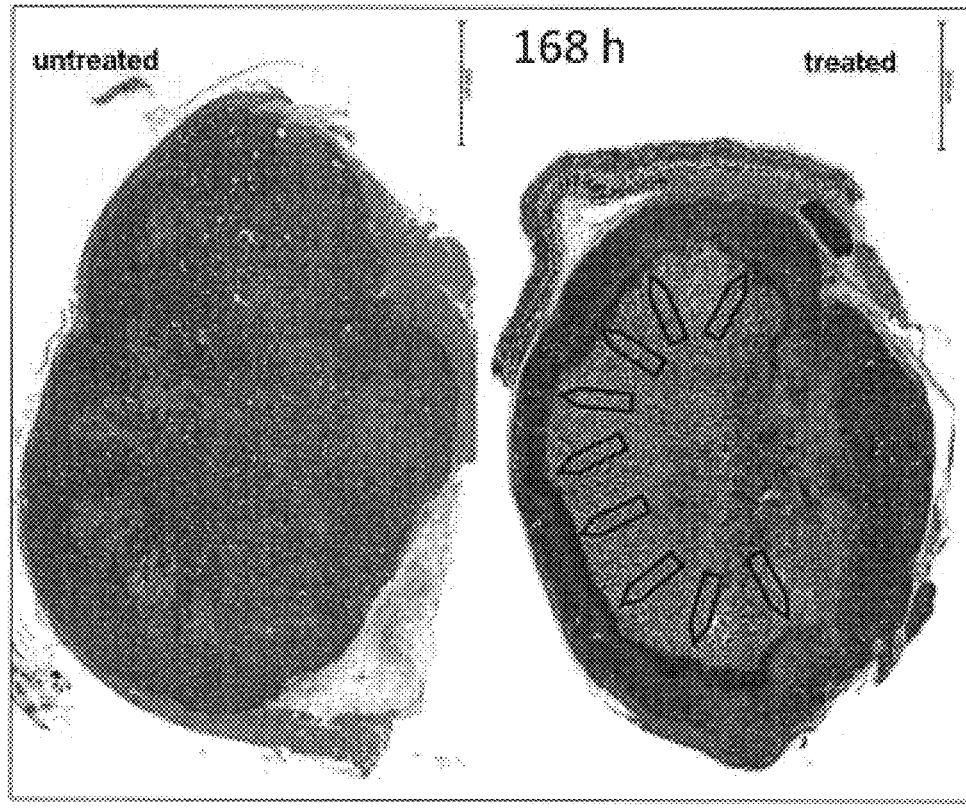
Figure 45A:
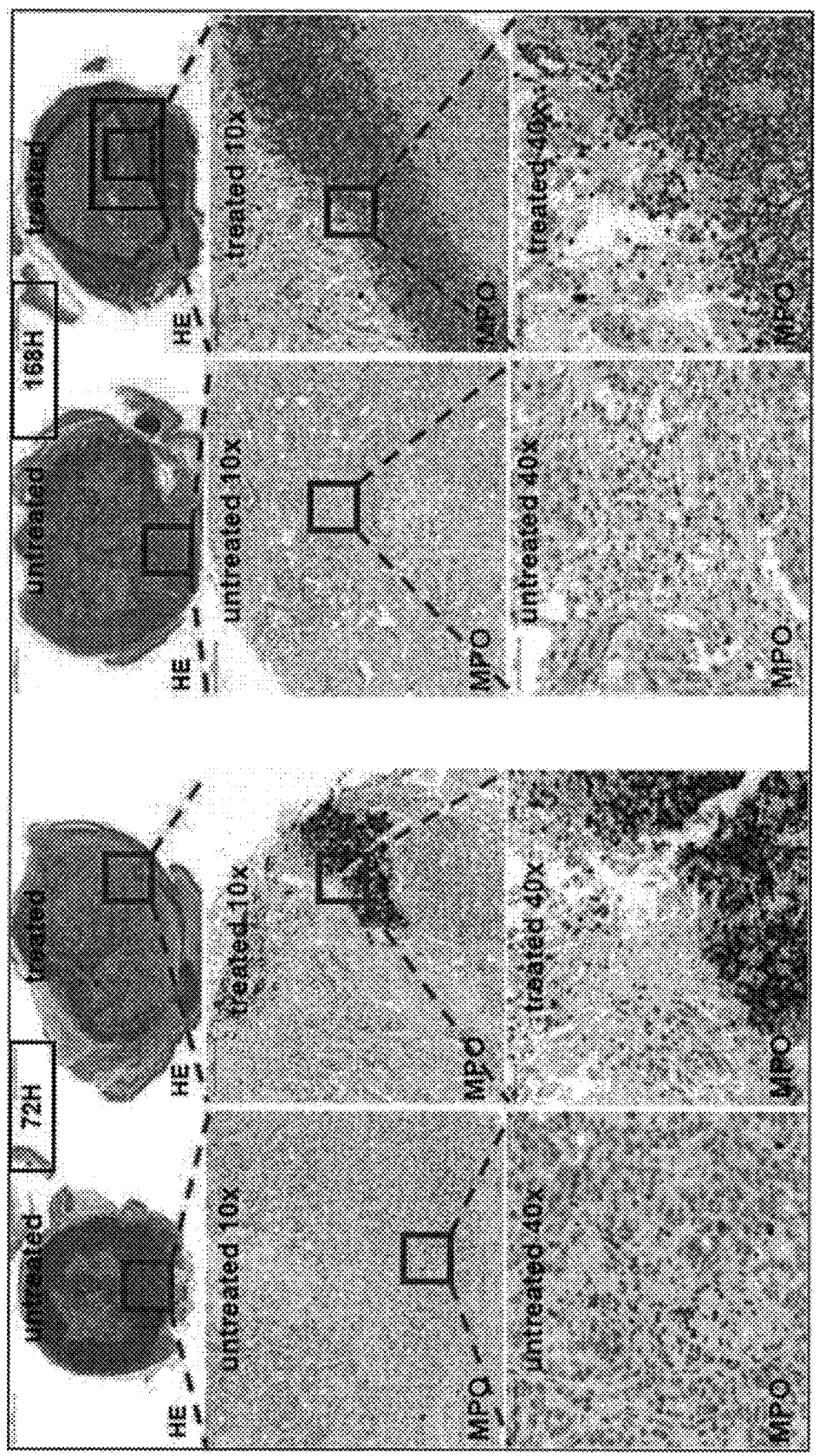
FIG. 45A shows the IHCH detection of myeloperoxidase (MPO) from TMA multiblock.
Figure 45B:
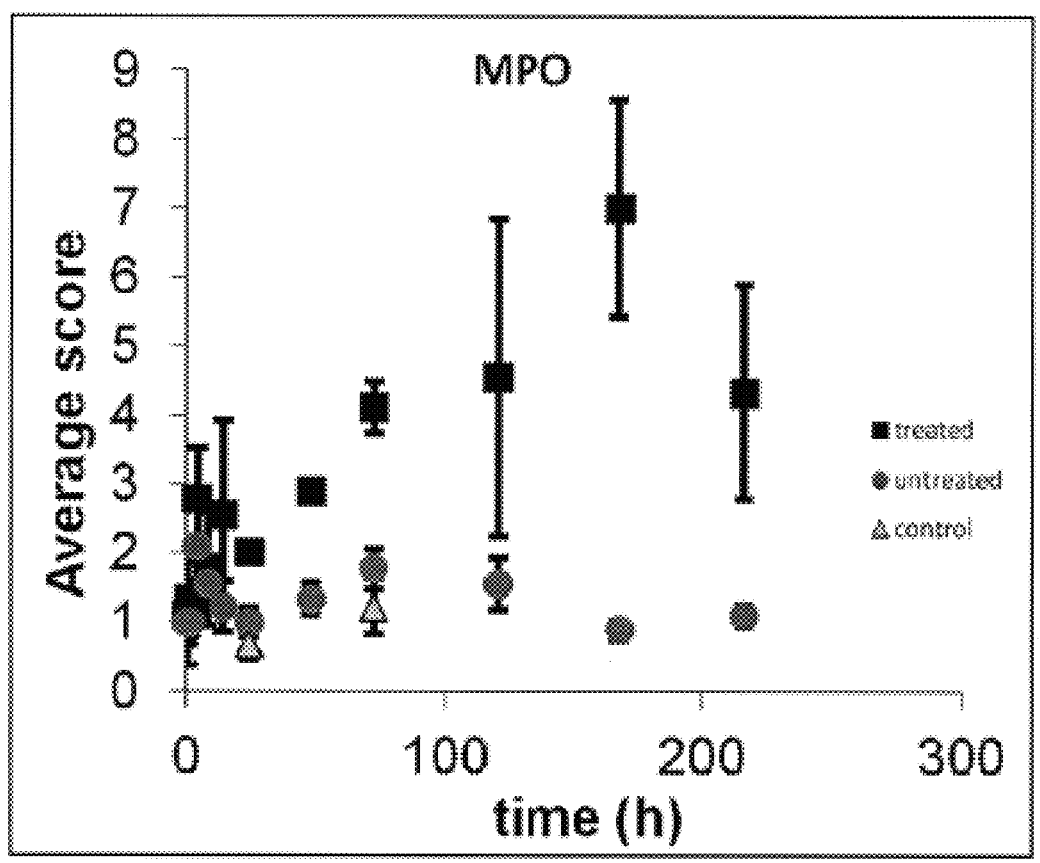
FIG. 45B shows the semi-quantitative analysis of the MPO+ cells from TMA multiblock samples.
Figure 45C:
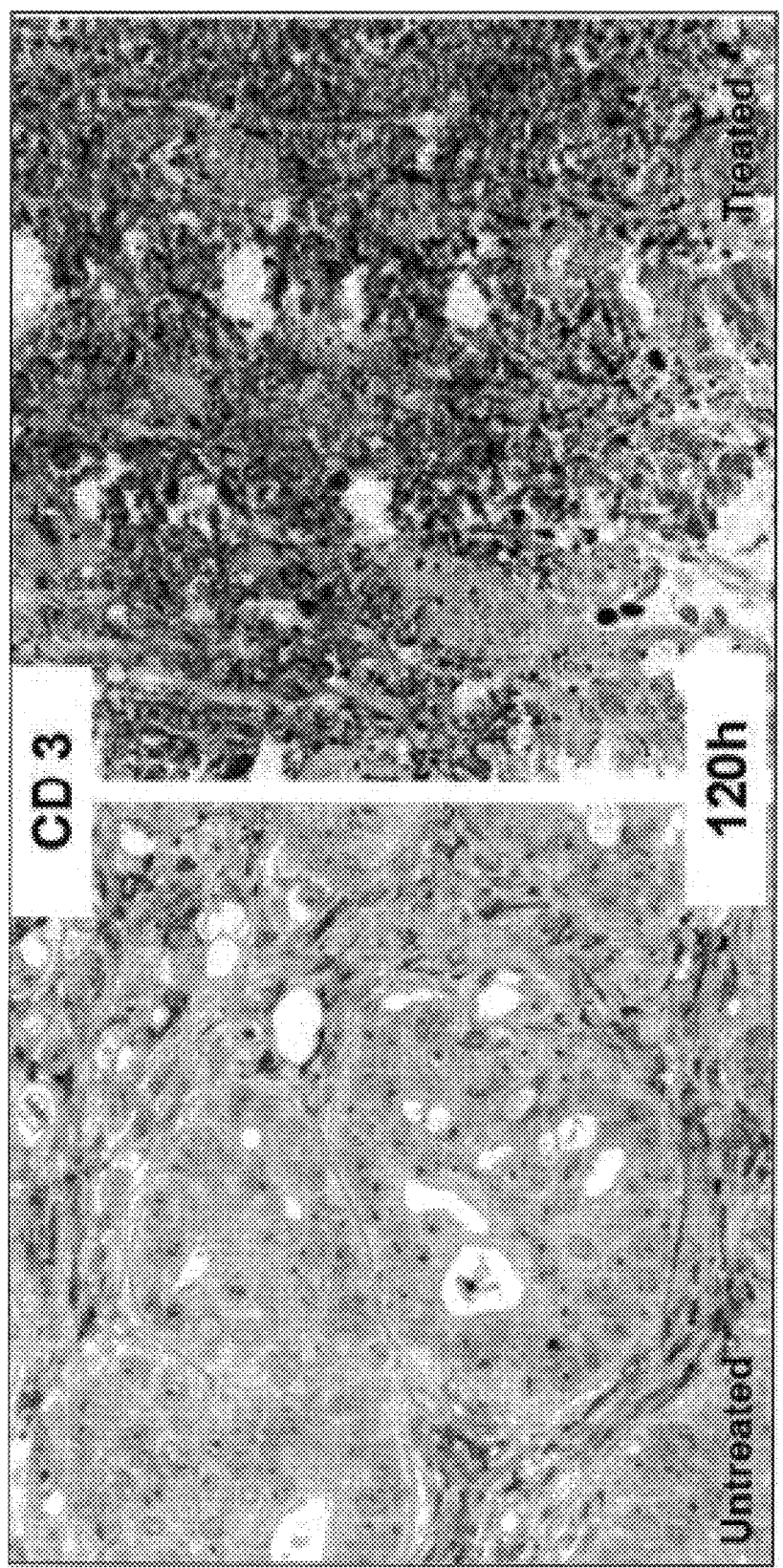
FIG. 45C shows the IHCH detection of CD3+ positive cells from TMA multiblock.
Figure 45D:
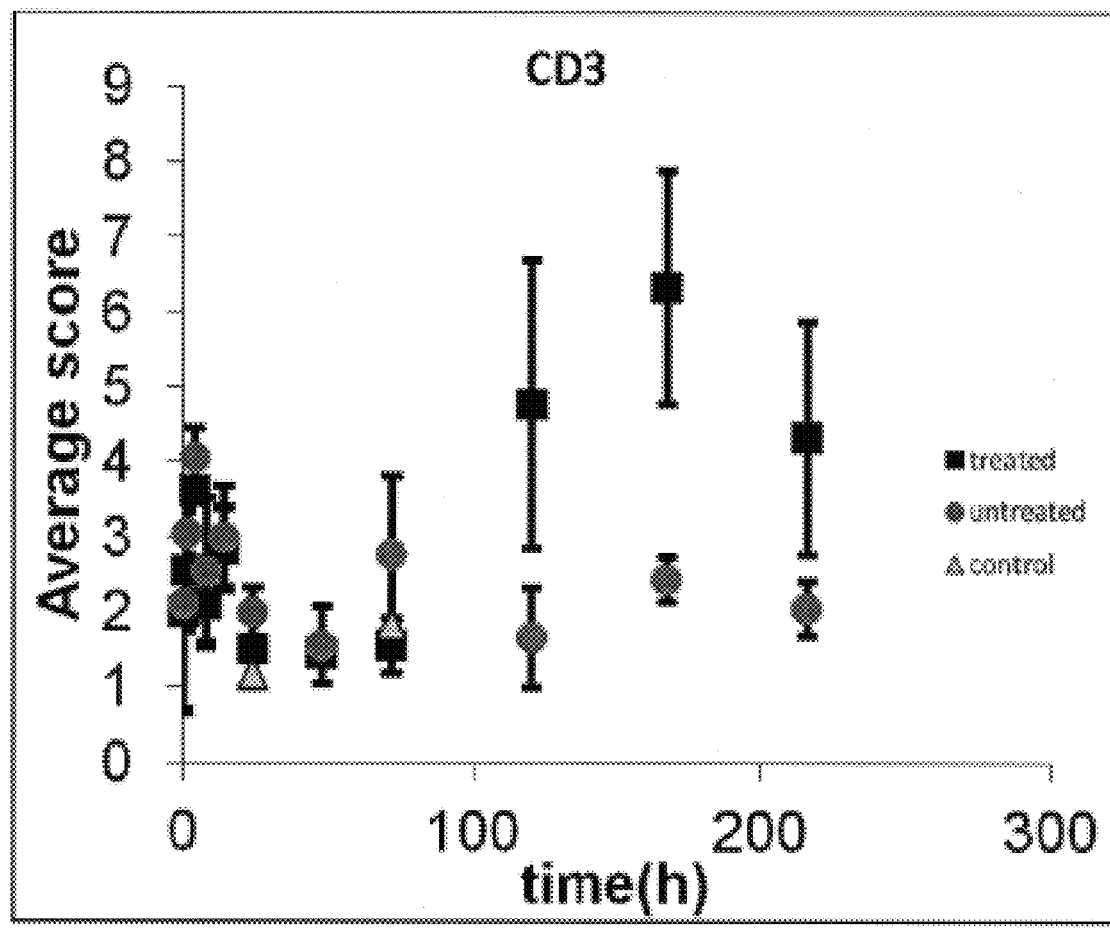
FIG. 45D shows the semi-quantitative analysis of the CD3+ T cells from TMA multiblock samples.

FIG. 44 shows
A. HE stained whole tumor cross sections 72 h post treatment. The arrows indicate the formation of the invasion ring.
B. HE stained whole tumor cross sections 168 h post treatment. The arrows indicate the well-defined invasion ring.

FIG. 45 shows
A. the IHCH detection of myeloperoxidase (MPO) from TMA multiblock. MPO is a marker of neutrophils (granulocytes). The leukocyte invasion ring that appears at 72 h and became very characteristic at 168 h around the destructed tumor area, contains high number of MPO positive cells (neutrophils).
B. the semi-quantitative analysis of the MPO+ cells from TMA multiblock samples. Oncothermia treated tumor samples contain much higher number of MPO+ cells (neutrophils) than the untreated and the control tumor samples.
C. the IHCH detection of CD3+ positive cells from TMA multiblock. The invasion ring contains a huge amount of CD3+ T cells 168 h post treatment.
D. the semi-quantitative analysis of the CD3+ T cells from TMA multiblock samples. Oncothermia treated tumor samples contain significantly more CD3+ cells (T lymphocytes) than the untreated and the control tumor samples.

Figure 46:
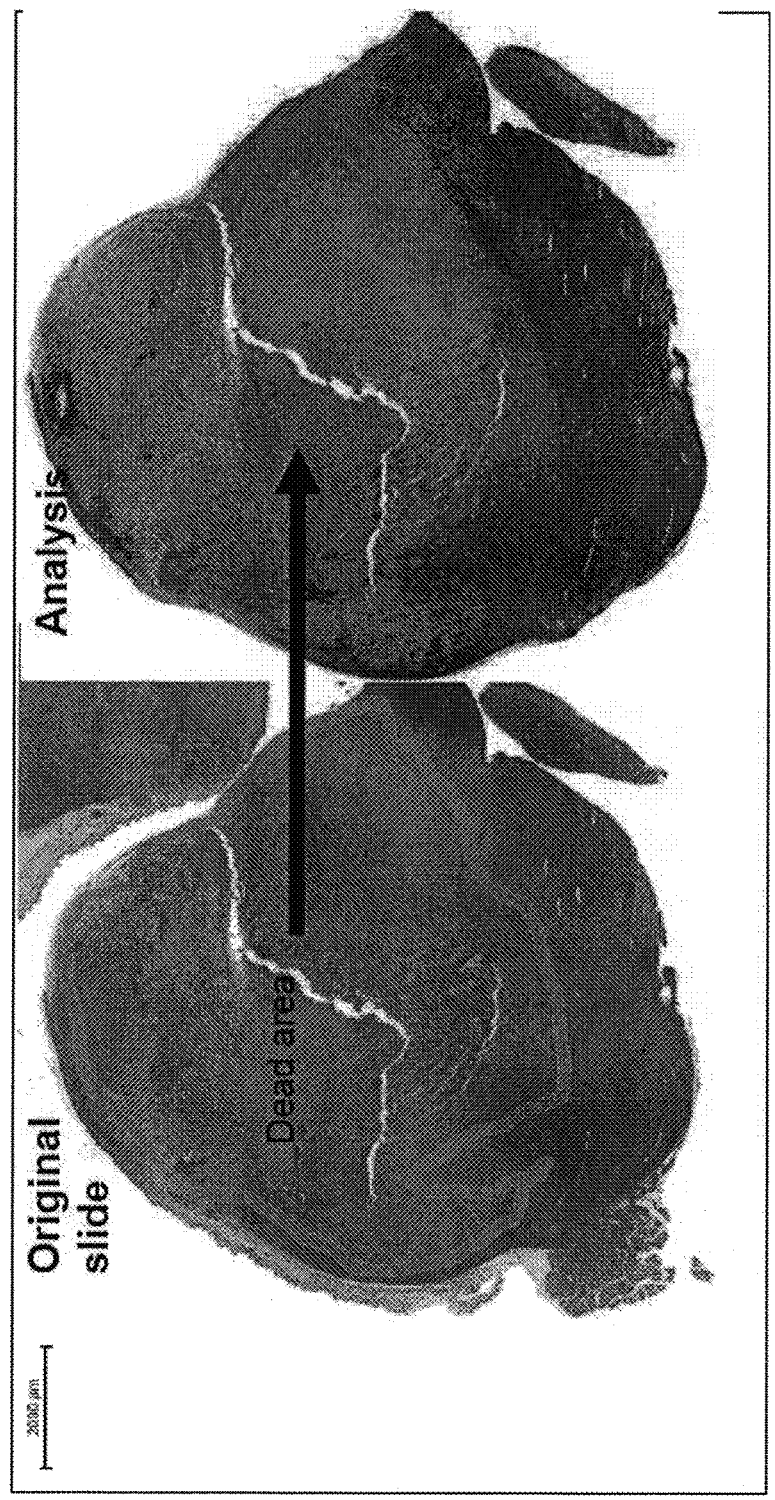
FIG. 46 displays the histomorphological analysis method.

FIG. 46 displays the histomorphological analysis method.

Figure 47:
FIG. 47 shows the systemic effect of the vaccine according to the present invention.

FIG. 47 shows the systemic effect of the vaccine according to the present invention. Regression of the far away situated metastases from the site of treatment was observed.

FIG. 48 shows the beneficial effect on the reduction of the tumor volume in orthotopic 4T1 tumor model provided by the vaccine according to the present invention. Oncothermia (radiofrequency waves using capacitive coupling in a condenser arrangement) in association with TJ-48 was administered as described in Example 14.

The following examples are included to demonstrate preferred embodiments of the invention. It should be appreciated by those of skill in the art that the techniques disclosed in the examples, which follow represent techniques discovered by the inventor to function well in the practice of the invention, and thus can be considered to constitute preferred modes for its practice. However, those of skill in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Materials and Methods
Tumor Model
Cell Line

HT29 invasive colon cancer cell line (provided by Tyrolean Cancer Research Institute, Innsbruck, Austria) was propagated in Dulbecco modified Eagle's minimal essential medium (DMEM)+ GlutaMax, high-glucose (4.5 g/l) medium including 10% heat inactivated fetal calf serum (FCS) and 1% streptomycin-penicillin (5000 units penicillin and 5 mg streptomycin/ml). Cells were released from a sub-confluent monolayer using 0.25% trypsin+ ethylene diamine tetraacetic acid (EDTA, 0.22 mg/ml) for 5 min and suspended in a serum free medium to reach the required $10^7$/ml cell concentration. All reagents were purchased from GIBCO (Invitrogen, Carlsbad, USA).

Animal Model

Female nude Balb/c (nu/nu) mice (provided by the Experimental Animal House of the National Research Institute for Radiobiology and Radiohygiene, Budapest, Hungary) maintained in sterile environment, kept on sterilized food and water ad libitum under 12 h dark/12 h light cycles. Both femoral regions of 6 to 8-week old mice were subcutaneously injected with 0.1 ml suspension of $10^7$/ml HT29 cells. The animals (xenografts) were treated with 18 days after HT29 cell injection, when the diameter of tumor implants had reached ~1.5 cm. Mice only with symmetrical tumors in both legs were used for treatment. Laboratory animals were kept and treated in compliance with the relevant sections of the Hungarian Laws No. XXVIII/1998 and LXVII/2002 on the protection and welfare of animals and animal welfare regulations of the European Union. The Governmental Ethical Committee approved the study under No. 22.1/609/001/2010.

Treatment of Xenografts with Radiofrequency Waves Using Capacitive Coupling in a Condenser Arrangement Treatments were systematically made only on the right tumor of the animals, while the left was kept for individual control (see FIG. 5). Tumor implants in the right legs of Balb/c (nu/nu) mice were placed into the plan-parallel electric condenser of the circuit (see FIG. 9). The set-up allowed the immediate electric control by keeping the circuit's impedance at 50 Ohm depending on the dielectrics of the treated tissues including the tumor. Electrode arrangement was asymmetrical. The animals were laid down on the rectangular grounded (lower) electrode made of polished aluminum of 72.0 $cm^2$, which was kept at 37° C. during the treatment. The active (opposite) upper 2.5 $cm^2$ round shaped electrode, made of flexible textile (copper-silver-tin coated woven fabric, Lorix Ltd. Bajna, Hungary), was overlaid on the tumor region to provide full skin contact for the treated leg. The whole surface of the upper electrode was cooled from the outside by a wet pad. The electromagnetic field was generated at 13.56 MHz radiofrequency using 1/f amplitude modulation (LabEHY, Oncotherm Ltd, Paty, Hungary). Parameters were adjusted to keep intratumoral temperature at 41-42° C. on the treated side and ~36° C. on the control side. The subcutaneous temperature underneath the electrode was kept at ~40° C. and the rectal temperature was at ~37° C. The temperature was monitored at the above mentioned localizations by optical sensors (Luxtron FOT Lab Kit, LumaSense Technologies, Inc. CA, USA).

In this animal model, cancer implants were made parts of the electric circuit through capacitive coupling, i.e. placed in between the condenser electrodes. Since efficient tissue penetration can be achieved below ~25 MHz, a modulated radiofrequency of 13.56 MHz was used. The applied radiofrequency waves applied according to the invention are expected to interact with ions and bipolar molecular groups (non-thermal effect) resulting in their rotation and can also generate heat of ≤42° C. (thermal effect). Under the applied control, the 13.56 MHz frequency has no risk of damaging normal tissues, inducing action potentials in nerves or interfering with any telecommunication or electric instrument.

Study Design

Treatment groups involved 33 animals (FIG. 11.), which were delivered a single shot radiofrequency waves using capacitive coupling in a condenser arrangement for 30 minutes at an average power of 4 W under 100 mg/kg Ketamine and 10 mg/kg Xylazine anesthesia. Time course study was performed. After a single shot treatment, sampling was made 0, 1, 4, 8, 14, 24, 48, 72, 120, 168, 216 h post-treatment, using 3 mice in each group. Additional 5 untreated tumor implanted animals were sacrificed together with 24 h and 72 h post-treatment mice.

Tumor Sample Processing

Figure 10A:
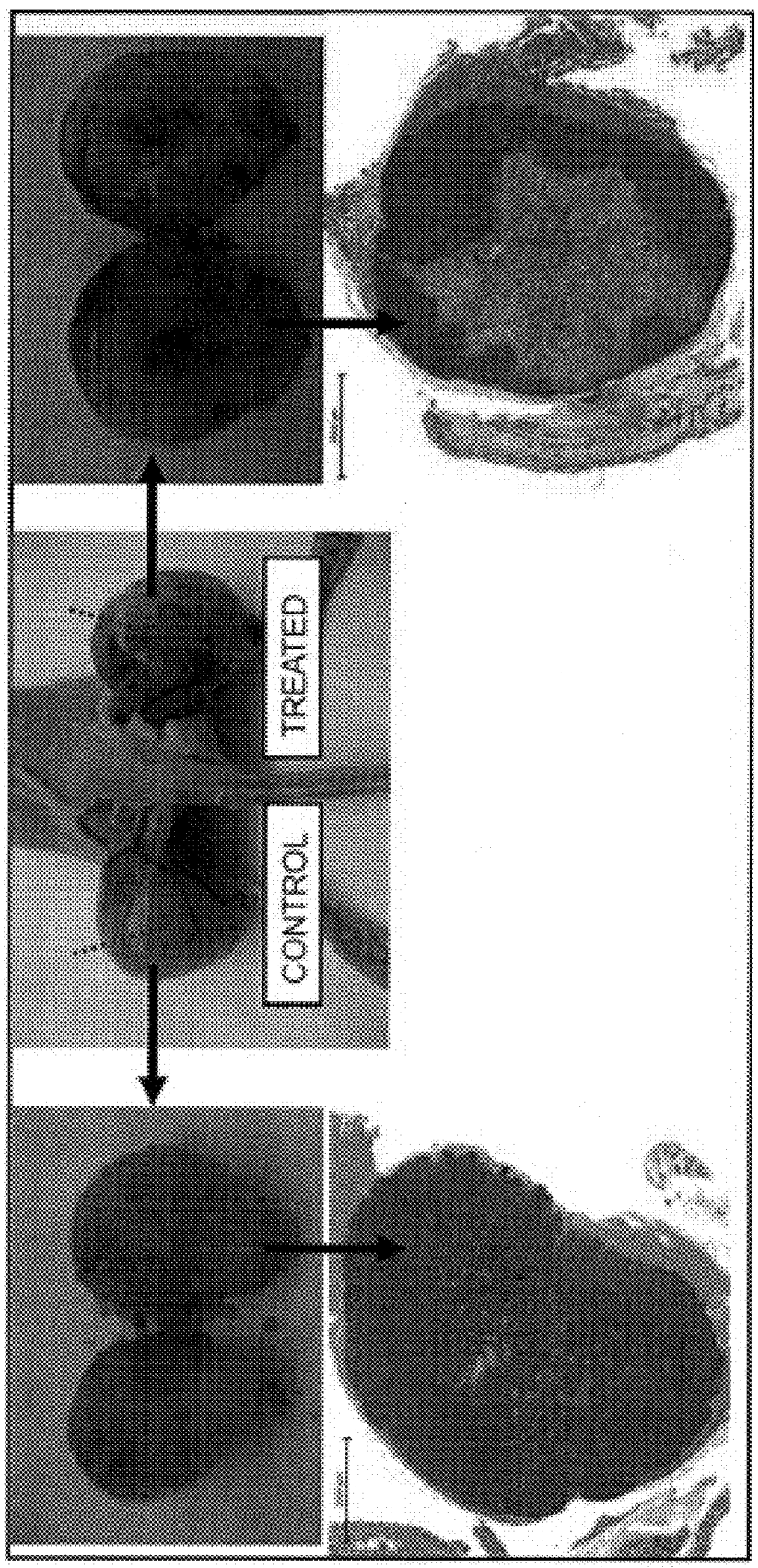
FIG. 10A shows the method of tumor dissection.

At the time of the sampling the single-treated animals were sacrificed and both the control and treated tumors were removed and studied in pairs (see FIG. 10A). One half of the excised tumors was fixed in 10% formalin, dehydrated and embedded routinely into paraffin wax (FFPE). The other half was fresh-frozen in liquid nitrogen and kept at −80° C. in deep freezer until further testing. The tumor samples were analyzed using different kind of methods (FIG. 10B).

Tissue Microarray (TMA) Method

Figure 10B:
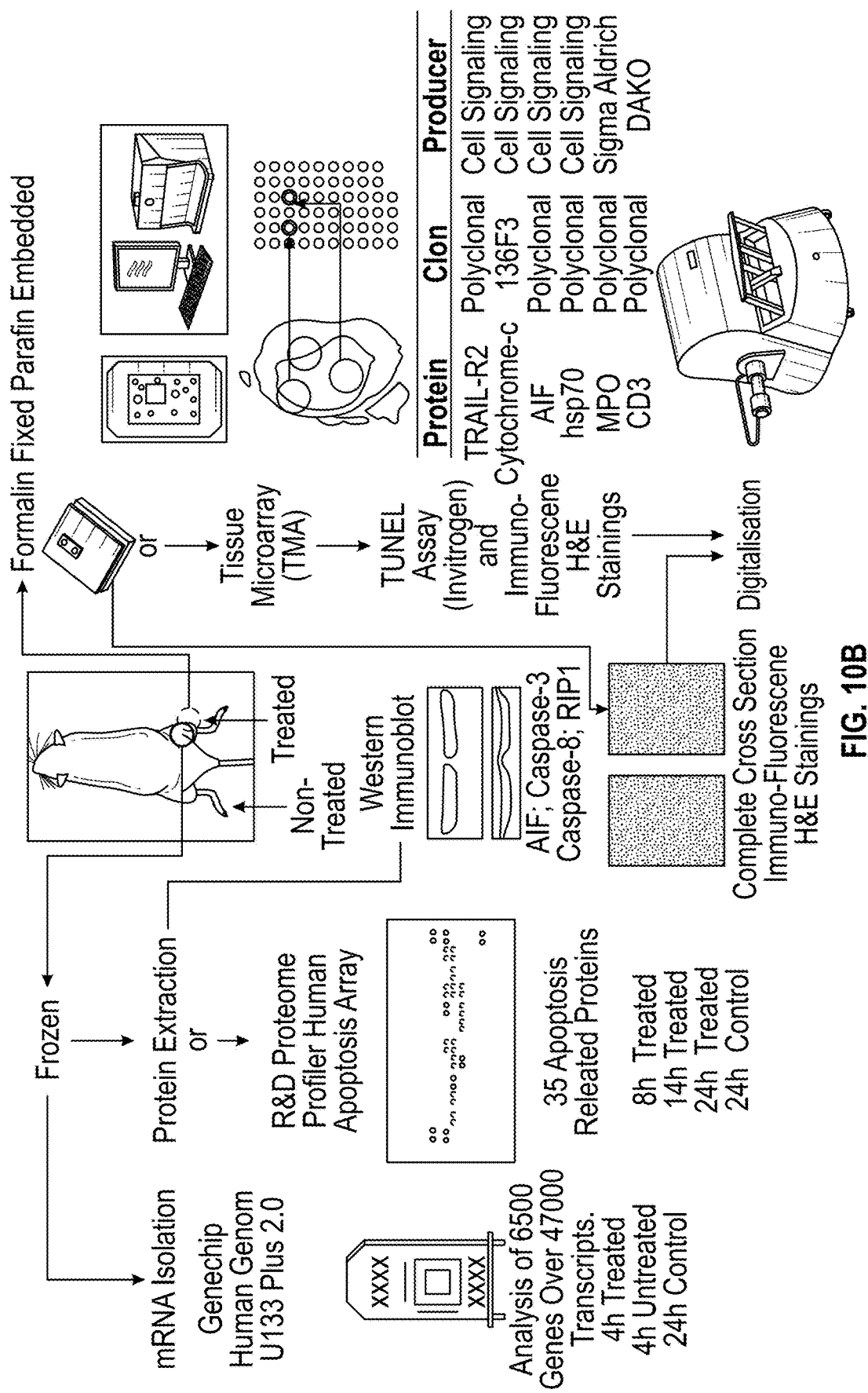
FIG. 10B shows the analysis scheme of the tumor sample.

Due to the extremely high number of the tumor samples, tissue microarray (TMA) technology was used to perform accurate immmono-histochemical reactions on many samples in one block (FIG. 10B). A multiblock contains many small (2 mm) representative tumor tissue samples, therefore identical and highly standardized immunohistochemical reaction can be performed in all the samples. This is the real advantage of this technology. TMAs included 3 cores of 2 mm diameter sampled from standard areas, 2 from the edges of degraded and intact tumor border and 1 from the degraded centre in each donor block (FIG. 38.) using the computer driven TMA Master (3DHISTECH Ltd., Budapest, Hungary).

Immunohistochemistry and Immunofluorescent Methods

For immunehistochemistry 4 µm thick sections were dewaxed, rehydrated and then endogen peroxidase enzymes were blocked using 3% hydrogen peroxide in methanol for 20 min except for immune fluorescence. Antigen retrieval was performed in electric pressure cooker (Avair Ida YDB50-90D, Biatlon kft, Pecs, Hungary) at ~105° C. in buffers made either of 0.01 M sodium citrate-citric acid (citrate, pH 6.0; for cleaved-caspase-3) or 0.1 M Trisbase and 0.01 M EDTA (T-E, pH 9.0, for all other antibodies), followed by bovine serum albumin (BSA)-Azide (1%, Sigma-Aldrich, St Luis, Mo.) protein block for 20 min. Sections were incubated for 16 h in a humid chamber at room temperature with the following primary antibodies:
1. polyclonal rabbit anti-human cleaved-caspase-3 (1:100, Cell Signaling Danvers, Mass.),
2. myeloperoxidase (1:200, Sigma-Aldrich),
1. AIF (1:50, Cell Signaling),
2. TRAIL-R2 (1:50, Cell Signaling),
3. Calreticulin (1:200, Cell Signaling)
4. HMGB1 (1:200 Cell Signaling)
5. CD3 (1:2, Dako, Glostrup, Denmark)

Then, EnVision polymer peroxidase detection system (Dako) was used for 30 min. For enzyme development either 3,3'-diaminobenzidine (DAB, brown) kit (RE7105, Leica-NovoCastra, Newcastle, UK) or aminoethylcarbazole (AEC, red) kit (K3461, Dako) was used. Between incubations, the slides were washed in Tris-buffered saline buffer (TBS) for 3×2 min and finally counterstained using hematoxylin.

For immune fluorescence (IF) primary antibodies were detected using Alexa Fluor 546 (orange-red) coupled anti-rabbit IgG (1:200) or Alexa Fluor 488 (green) coupled anti-mouse IgG (1:200) for 90 min and cell nuclei were revealed in blue using 4',6-diamidino-2-phenylindole (DAPI) (all from Invitrogen/Molecular Probes). The bright field images were scanned while the IF images were either scanned by the SlideScanner system or a Nicon Eclipse e-600 was used.

Apoptosis-Related Protein Analysis Proteins were isolated from the frozen samples using extraction buffer (20 mM Tris, 2 mM EDTA, 150 mM NaCl, 1% Triton-X100, 10 µl/ml phosphatase inhibitor and 5 µl/ml proteinase inhibitors) for 30 min on ice, followed by centrifugation at 15,000 rpm at 4° C. for 15 min. Protein concentration was measured with Bradford assay.

Apoptosis Array

The expression of 35 apoptosis-related proteins was tested simultaneously in the treated and untreated samples using a nitrocellulose membrane Proteome Profiler™ Human Apoptosis Array Kit (R&D, Minneapolis, Minn.) (FIGS. 21 A and B.) Arrays were incubated on a shaker with 250 µl of 1,200 µg/ml protein lysates at 4° C. overnight, then with biotinylated anti-human IgG for 60 min and Streptavidin-horseradish peroxidase (HRP) conjugate for 30 min and visualized using a chemiluminescence ECL kit (SuperSignal® West Pico Chemiluminescent Kit; Thermo Scientific, Rockford, Ill.) for 10 min in Kodak Image Station 4000 mm (Rochester, N.Y.). Semi-quantitative analysis was done using ImageJ 1.45 s (http://rsbweb.nih.gov/ij/).

Western Immunoblots

For western immunoblots the protein extracts were mixed with 5× Laemmli sample buffer containing 5% 2-mercaptoethanol and heated to 95° C. for 5 min. 30 µg protein was loaded into each well of 12% sodium dodecylsulfate polyacrylamide gel (SDS-PAGE) and electrophoresis was done at 150 V for 1 h. Proteins were then immunoblotted into polyvinylidene difluoride (PVDF) membrane at 75 mA and 4° C. overnight. For immunodetection, membranes were sequentially incubated with 5% semi-skimmed milk as a protein block for 60 min followed by incubation with rabbit anti-human AIF (1:1000; Cell Signaling, Danvers, Mass.), RIP (receptor-interacting protein kinase; 1:1000, Sigma-Aldrich) antibody at 4° C. for 16 h. For loading control rabbit anti-β-actin (1:200, Thermo) antibody was used for 60 min. Then signals were detected with horseradish peroxidase (HRP)-conjugated goat anti-rabbit IgG (1:1000; Cell Signaling) for 60 min and SuperSignal enhanced chemiluminescence (ECL) kit (Thermo) for 10 min by using Kodak Image Station and its 4.1 software. Precision Plus Protein Standard ladder produced bands at 250 kDa, 150-, 100-, 75-, 50-, and 37 kDa. All reagents except where otherwise indicated were from Bio-Rad (Hercules, Calif.).

TUNEL Assay

Based on pre-screening in TMA sections TUNEL assay was also done on whole cross sections of tumors treated with radiofrequency waves using capacitive coupling in a condenser arrangement and their matched controls collected 24 h and 48 h post-treatment. TUNEL assay links DNA nick ends using terminal deoxynucleotidyl transferase (TdT) with fluorochrome labeled deoxyuridine triphosphate (dUTP). Thus, fluorescence signals in cell nuclei are proportional with the amount of fragmented DNA for indicating programmed cell death. The "Click it TUNEL Alexa Fluor 488 Imaging Assay" (Invitrogen) was used according to the manufacturer's instructions. Briefly, dewaxed and rehydrated slides were heated in a citrate based pH 6.0 antigen unmasking solution (H-3300, Vector Lab, Burlingame, Calif.) using electric pressure cooker (as above). Then slides were incubated at 37° C. for 60 min with a cocktail of alkynes substituted dUTP and TdT followed by the fluorochrome coupled to dUTP for 30 min at room temperature. Finally, nuclear DNA was stained with DAPI.

Digital Microscopy Method:

The Slide Scanning Procedure:

Whole cross sections and TMA samples stained for hematoxylin and eosin (H&E), immunohistochemistry or TUNEL assay were digitalized using Pannoramic Scan slide scanner system using a 20× objective (3DHISTECH, Budapest, Hungary).

The Digital Microscopy Imaging and Analysis:

Tumor tissue imaging was performed using the Panoramic Viewer software. The magnification of the image was adjusted digitally, all imaged tumor sample contains an indicator scale bar. The quantitative analysis of the samples was done manually or using the the HistoQuant module of Pannoramic Viewer software (all from 3DHISTECH, Budapest, Hungary) based on image color and intensity segmentation. The oncothermia treatment related tumor destruction ratio (TDR) was calculated by dividing the area of destructed tumor tissue (D) by the whole tumor area (W)

measured in whole cross sections. Treatment related tumor destruction efficiency (TDE) was assessed by dividing the TDR of the treated by the TDR of the untreated tumor of the same animal (FIG. 39). For statistical analysis the Kruskal-Wallis test of the SPSS Statistics v.20 software (IBM Corp. New York, N.Y.) was used.

The number of marker positive cells, cell nuclei or apoptotic bodies were counted at ×100 objective magnification in 10 different microscopic fields (FOV) of 3 treated and 3 untreated samples at each tested time point. Since nuclear localization was critical both for AIF and TUNEL stained samples, DAPI co-staining was used for verification. For cytochrome c staining cells with diffuse cytoplasmic signal were counted only in the morphologically intact tumor areas. Apoptotic bodies were counted on H&E slides. The TRAIL-R2 and cleaved caspase-3 stained slides were evaluated using the HistoQuant software. The relative mask area (rMA) was defined by dividing the marker positive mask area by the overall annotated area. For statistics, the Kolmogorov-Smirnov normality test was carried out followed by the independent t-test, using SPSS Statistics v.20. For myeloperoxidase and CD3 stained slides a 10-scale system was set up to score the frequency of positive cells and the results were analyzed using the Kruskal-Wallis test.

Example 1: Tumor Destruction

Figure 40A:
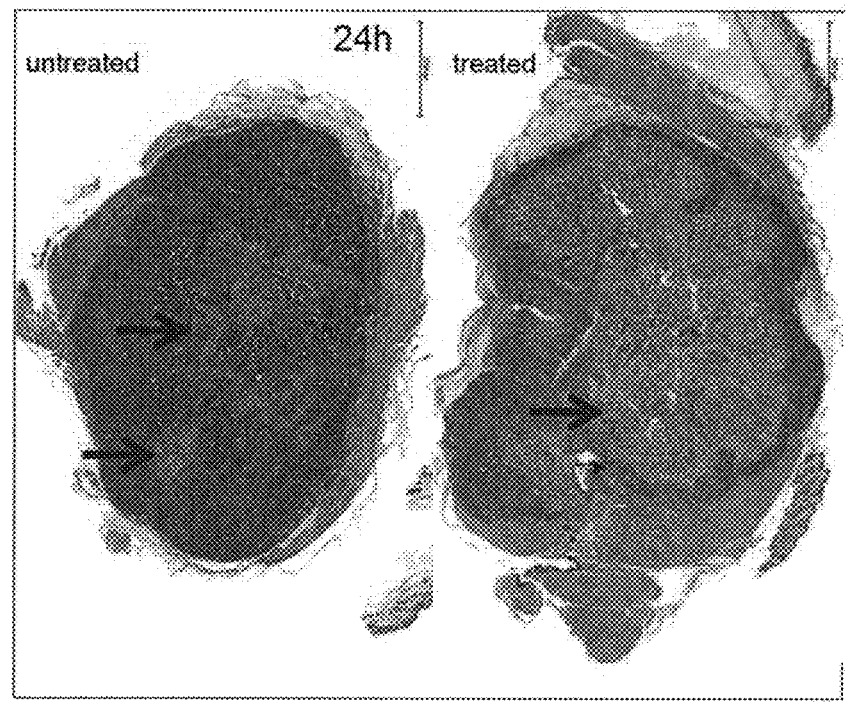
FIG. 40A. shows the qualitative histomorphological appearance of the oncothermia treatment induced tumor destruction 24 h after a single shot treatment.
Figure 40B:
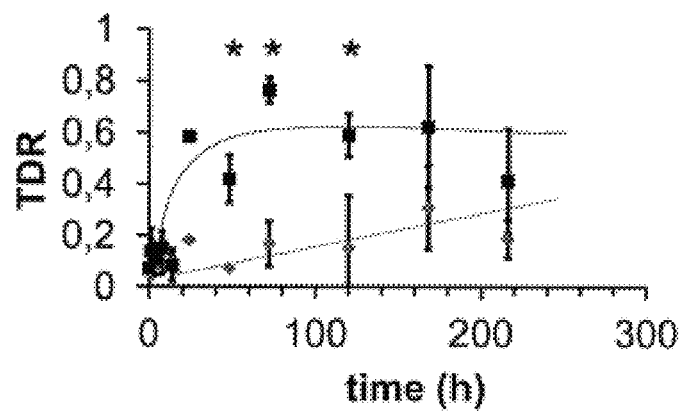
FIG. 40B. shows the result of the quantitative analysis of the tumor destruction ratio.
Figure 40C:
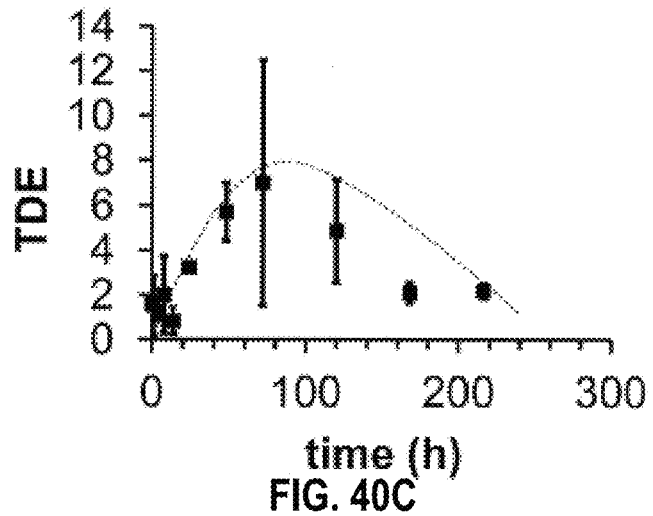

In H&E stained cross sections of HT29 xenografts the damaged central zones of tumors were demarcated as pale areas (Arrows in FIG. 40A). Digital slide viewer software allowed accurate area measurements in μm². Tumor destruction ratio (TDR), the proportion of damaged (D) per whole (W) tumor area, was significantly higher (*p<0.05) in the treated compared to the untreated tumors (see FIG. 40B.). The oncothermia treatment related tumor cell destruction (TDE) also showed a dynamic increase from 24 h on with a 7-fold peak observed at 72 h post-treatment (FIG. 40C).

Example 2: DNA Fragmentation

TUNEL assay proved significantly higher programmed cell death related DNA fragmentation in whole cross sections (FIG. 41) of the treated compared to the untreated tumors both at 24 h (*p<0.05) and 48 h (**p<0.01) post-treatment (FIG. 42 A-B). In agreement with this, there was a significantly higher degree of nuclear shrinking (pyknosis) and accumulation of dense chromatin fragments (apoptotic bodies) in the treated compared to the untreated tumors both at 48 h (*p<0.05) and 72 h (**p<0.01) post-treatment (FIGS. 42 A and C).

Example 3: The Apoptotic Body Formation

The significant elevation in DNA fragmentation measured with TUNEL assay, nuclear shrinkage and apoptotic bodies (see FIG. 14.) proved programmed cell death as the major mechanism behind oncothermia (radiofrequency waves using capacitive coupling in a condenser arrangement) induced tumor destruction.

Example 4: Calreticulin Expression

Calreticulin (CRT) is one of the most important molecule in the process of the ICD. When CRT appears on the tumor cell membrane it can generate a strong signal for the phagocytotic cells, including dendritic cells (DC), to attack the dying tumor cell. This is the most significant "eat me" signal for immune cells. Oncothermia (radiofrequency waves using capacitive coupling in a condenser arrangement) treatment can increase significantly the membrane-expression of the CRT shortly after the treatment (FIG. 16).

Example 5: HMGB1 Expression

HMGB1 is the other important hallmark of the ICD. In normal state HMGB1 is located in the cell nuclei, where it stabilizes the nucleus and regulates the transcription of many genes. More and more evidence suggests that it can be released from apoptotic cells. Extracellular HMGB1 act as a cytokine and can activate DCs (through TLR 4) therefore can trigger anti-tumor T cell responses and mediate ICD. Oncothermia (radiofrequency waves using capacitive coupling in a condenser arrangement) treatment induced programmed cell death accelerate its release to the extracellular matrix (FIG. 15 and FIG. 43), contributing to activate DCs and mediate the antitumor immune reaction processes.

Example 6: TRAIL Expression

A proteome profiler nitrocellulose array including antibodies for 35 programmed cell death related proteins was used to test the molecular background of oncothermia induced cell death. This protein array revealed a significant upregulation of the death receptor TRAIL-R2 8 h post-treatment compared to the untreated controls (FIG. 17 A). Significantly elevated cell membrane expression of TRAIL-R2 protein in the treated tumors was also confirmed both at 8 h and 14 h when immunofluorescence staining was tested with automated image analysis (FIG. 17 B-C).

Example 7: HSP70 Expression

HSP70 chaperons have complex functions. In the cell HSPs try to keep the integrity of the cells, but if it can expressed to the cell membrane (FIG. 18A) or released to the ECM (FIG. 18B) it is a strong signal to immune cells. HSPs play an important role in tumor specific or tumor associated antigen recognition by the process of cross-priming and co-presentation.

Example 8: Histomorphological Signs of the Local Immune Reactions

Around the destructed area of the oncothermia treated tumor 72 h post-treatment a leukocyte invasion ring appeared (FIG. 44A), which became more emphasized 120 h and 168 h after a single shot oncothermia treatment (FIG. 44B)—

Example 9: Immunohistochemical (INCH) Identification of the Leukocytes in the Invasion Ring Morphologically the different immune cells in the invasion ring cannot be distinguished. Complex immunohistochemical detection was necessary to reveal the composition of the immune cell populations. Myeloperoxidase (MPO) is the key marker of neutrophils (FIGS. 45 A and B), CD3 is the marker of naïve T cells (FIGS. 45 C and D).

In view of the results presented in the examples 1-9, it can be concluded that:
1. Oncothermia treatment can induce programmed cell death in the tumors which create many apoptotic bodies.

Presence of apoptotic bodies in a destructed tumor tissue is essential to induce immunogenic reactions.

2. Oncothermia treatment induced cell death is highly immunogenic, showing all the key molecular pattern dynamic changes being characteristic of immunogenic tumor cell death.

3. Oncothermia treatment can induce strong and very unusual local immune reaction at the site of the treatment, long time after the oncothermia treatment.

4. The local antitumor immune reaction of oncothermia treatment might be systemic, if the host has an intact immune system, and a proper immune stimulant is administered. This process can control the distant metastases by bystander effect, making possible the systemic control of the malignant disease with local treatment.

Example 10: Administration of the Radiofrequency Waves Using Capacitive Coupling in Combination with Xiao-Aiping Xiao-aiping injection (Xi) is used by the traditional Chinese medicine (TCM). This injection is decoctum of Marsdenia tenacissima, which contains flavonoides, chlorogenic-acid and polydatin. The experiment was performed using conventional female BALB-C mice, in 4 groups, 4 animals/group:

C: sham control

Xi: treatment with Xi injection, dose: 7.5 ml/kg bodyweight/day, intraperitoneally for 4 days OTM: Oncothermia treatment once for 30 minutes of the right femoral tumor OTM+Xi: treatment with Xi injection, dose: 7.5 ml/bwkg/day, intraperitoneally for 4 days, on the $4^{th}$ day OTM treatment once for 30 minutes of the right femoral tumor Allografts were generated by injecting $10^6$ cultured C26 colon-adenocarcinoma cells subcutaneously to both femoral regions of the animals. 14 days later this symmetric double-tumor model gave opportunity to use internal control (treated and untreated tumors) for the oncothermia treatment and also for investigation of systemic effects of the Xi and the combination treatment.

OTM treatment, experimental setup (FIG. 24.)

RF paramneters:
  13.56 MHz
  Amplitude modulated with 1/f noise
  Capacitive coupled—Impedance tuned
System:
  LAB-EHY 100 (Oncotherm, Páty)
  Duration: 30 min
  Output power: 1-3 W Animals were sacrificed 24 hours after the last treatment, neoplastic tissue was excised and formalin fixed.

Histopathological and immunohistochemical examination of the samples were performed:
  Hystopathology: H&E slides
  lmmunhistochemisrty
    TUNEL Assay (nucleic-acid fragmentation) (FITC)
    CD3 (lymphocyte) (rhodamine)
    HSP70 (rhodamine)
  Evaluation: relative Dead Area ratio compared in pairs in each group (HistoQuant, 3DHistech) (FIG. 39.)

Although the Xi therapy alone was ineffective according to the results, the combination with the oncothermia treatment produced massive destruction of the tumors both at the oncothermia-treated and at the untreated side as well. Oncothermia monotherapy resulted in destruction of the treated tumors only, while there was no considerable difference between untreated tumors and the sham treated allografts (FIGS. 26A and B).

According to the results, the OTM+Xi combination treatment has systemic effect against the multi-localized tumors in the tested animals. The level of destructive effect against the tumor on the untreated side was statistically equal with the effect experienced at the treated side either in the same group or in the OTM monotherapy group as well. Histo-morphological and immonohistochemical findings can be seen in FIGS. 27-36.

Example 11: Radiofrequency Waves Using Capacitive Coupling in a Condenser Arrangement in Association with Low Dose Carboplatine This report supports ability that oncothermia treatment in association with immune stimulant provides a systemic effect and eradicates metastases far-away from the site of the treatment.

Case No.:11461, Cocker spaniel, 8 years, castrated male,

Diagnosis: melanoma with lung metastases. The primary tumor was situated on the right hind leg and was removed surgically. 5 months later metastases in the lung occurred, at that time we started the treatment.

Treatment:
  Oncothermia (10 times in a 2 weeks period)
  Low dose Carboplatine 2 times, (100 mg/m$^2$)
  (The prescribed dose of Carboplatine for dogs is 300 mg/m$^2$)

Carboplatine in much lower dose than the originally prescribed one has immunostimulatory properties. The explanation of this effect is, that in lower dose the cytotoxic effect of this drugs is not significant for the cancer cells, but can effectively block the function of the regulatory T cell ($T_{reg}$; formerly known as suppressor T cells) function. $T_{reg}$ cells can control the intensity of the immune reactions so if the number of $T_{reg}$ cells is decreased, the general activity of the immune system is somehow upregulated (Patients having impaired $T_{reg}$ cell function causes develop severe autoimmune diseases).

The site of the OTM treatment was on the chest, exactly at the line of the heart. Significant tumor regression was observed not only at the site of the treatment, but outside of the directly OTM treated area as can be visible in the CT image series (see FIG. 47)

Example 12

Typical time-course measurements experiments were performed as follows:
  mice female nude BALB/c (nu/nu) were used
  cell-line, HT29, human colorectal cancer;
  xenograft model in two femoral regions, one is treated only;
  time course study 0→216 h, 39 animals, (78 tumors);
  the used treatment is radiofrequency waves using capacitive coupling (oncothermia), single-shot, 30 min, 42° C.;
  the frequency used, 13.56 MHz, pink-noise modulated;
  the nature of the electrodes is flexible according to the patent WO 2009/092619;
  the data were analyzed, as previously described—the immune stimulant: E. coli LPS immune stimulant (100 µg LPS in 100 µL Salsol solution) was administered sc. to the dorsal region of the animal 24 h before the administration of the radiofrequency waves using capacitive coupling (oncothermia treatment).

The summary of the typical time-course measurements is shown in FIG. 11. This study uses the complete cross-sections to identify the morphology. The typical result of the treatment is the apoptosis of the tumor cells (see FIG. 12), which is proved by multiple researches and different methods of detection, as disclosed below.

The dominant presence of apoptosis is experimentally proven by TUNEL assay (done as previously described) showing the DNA defragmentation as shown by FIG. 12. As shown by FIG. 13, the apoptosis timescale is well sustained by time-course experiments Firstly, the antigen containing apoptotic bodies are well observable (see FIG. 14) as the overall marker for the immunogenic apoptotic cell-death, which is the basic of the vaccination method according to the present invention. This specialty (dominant apoptotic cell-death) of the treatment with radiofrequency waves using capacitive coupling (oncothermia) is a key factor of vaccination effect. The formation of damage associated molecular pattern and the stimulation of the complete immune reactions are two necessary conditions of immunogenic cell-death.

The oncothermia induced effects on the necessary DAMP members are experimentally proven. Thus, treatment with radiofrequency waves using capacitive coupling results in HMGB1 presentation and release to the extracellular matrix (see FIG. 15). Moreover, 4 h post-treatment, calreticulin expression on the cell membrane is observed (see FIG. 16).

Furthermore, treatment of cancer cells with radiofrequency waves using capacitive coupling induces expression of TRAIL-R2 (DR5) (see FIG. 17) and the HSP70 expression in the extracellular space and on the membrane surface of the cells (see FIG. 18).

The evaluation of the average relative percentage of HSP70 in the tumor volume shows two independent developments (see FIG. 19):
  the first development is over after 48 h from treatment with radiofrequency waves using capacitive coupling, and is connected to the direct HSP70 heat-induction;
  the second development starts afterwards and contributes to the immunogenic cell-death as part of DAMP The evaluation of the mRNA expression 4 h post-treatment with radiofrequency waves using capacitive coupling outlines the ability of the treatment according to the presence invention to induce the synthesis of the following proteins: HSP4, HSPA8, BAG3, HSPB1, DNAJB1, HSPA1A, HSP90AA1, DNAJB4, HSPA6, HSPD1, HSP1L (see FIG. 20 and FIG. 3).

To further investigate the apoptotic mechanism of the cell death, human apoptosis proteome profiler assays were performed. The results are summarized in FIG. 21. The effect of the treatment with radiofrequency waves on the expression of proteins involved in death inducing pathways, like TRAIL-R2 (DR5), FAS and FADD as displayed in FIG. 22 provides further insights in the mechanism of realization of the cell-membrane apoptotic pathway.

Thus, the most important proteins involved in the induction of tumor cell apoptosis by the treatment with radiofrequency waves using capacitive coupling were identified. Moreover, the immune responses to the treatment with radiofrequency waves using capacitive coupling were differentiated: Hence, as shown in FIG. 23, the apoptotic event of the treated cancer cell lapses before 48 h post-treatment and is followed after a transition period by a strong activation of the immune-system, which leads to immunogenic cancer cell death.

As shown by FIG. 4, the anti-tumor vaccine according to the present invention provides a systemic effect: the untreated tumor situated on the other limb is shrinking in response to the treatment applied to the tumor situated on the other limb. The state of the art literature shows only off-situ immune support, when the laboratory assistance was necessary for far-distant (immuno-assisted) effects. In the treatment in accordance with the present invention the main point is the in-situ application. Oncothermia alone (radiofrequency waves using capacitive coupling) does not have any effect on the far-away situated tumor. LPS administration does not either have an effect on tumor regression. However, LPS assisted administration of radiofrequency waves using capacitive coupling provides an abscopal effect and results in the shrinkage of the far-away situated tumor. Thus, oncothermia (radiofrequency waves using capacitive coupling) and LPS administration results in long distance (systemic) effect of the local Oncothermia.

Example 13: Radiofrequency Waves Using Capacitive Coupling in a Condenser Arrangement in Association with Leukine®

A 72-year-old male patient was diagnosed with unclassifiable non small cells lung cancer. The classification of the tumor at first diagnosis was cT2N2M0, stage IIIB. Despite of the advanced case the patient refused any treatment. Five months later, he visited outpatient department of complementary and alternative medicine with complaints of hemoptysis and dyspnea on exertion gradually worsened 4 weeks before. He was referred to medical oncology department and admitted for re-evaluation.

Staging work-up including chest CT and PET scans showed 9.5 cm sized cavitary mass at right middle lobe with multiple regional and metastatic lymph nodes. The patient had no co-morbidities and no medical history. However, he still refused chemotherapy and together with his family members requested other possible treatment options.

In these circumstances we made radiotherapy in combination with oncothermia and GM-CSF expecting to induce abscopal effect. Local field radiation therapy to lung mass was delivered at a dose of 1.7 cGy in 28 daily fractions for 5-6 treatments in a week. It was followed by oncothermia after radiation 3 times a week. After 2 weeks of oncothermia treatment, GM-CSF (250 microgram, Leukine®, USA) was administered subcutaneously once a day for 10 days. GM-CSF in dose 125 μg/m$^2$ was given subcutaneously for 14 days after one week of radiotherapy. The result supported that using GM-CSF was feasible and its effect enhanced the immune therapy.

Treatments were provided without any complications. Patient presented no severe adverse effects except grade 1 fatigue at the end of treatment period. By follow-up process, just after finishing radiation treatment series PET scan showed nearly complete remission in multiple metastatic lymph nodes, which were distantly away from radiotherapy field. The primary (treated) tumor was shrinking, the metastases in far distant disappeared (see FIG. 37).

Patient was satisfied and discharged with successful response. The follow-up of the patient is continuing. This case describes a successful abscopal effect with local radiotherapy in combination with oncothermia and GM-CSF immune-stimulation. This attempt seemed to be more effective in immune response than radiotherapy alone.

Example 14: Radiofrequency Waves Using Capacitive Coupling in a Condenser Arrangement in Association with Juzentaihoto (TJ-48)

The vaccine effect of the Juzentaihoto (TJ-48) in combination with radiofrequency waves using capacitive coupling in a condenser arrangement was evaluated on a 4T1(luc2) orthotopic tumor model.

Juzentaihoto (TJ-48) (Tsumura Co., Tokyo, Japan) is a Japanese herbal that has been used to alleviate anemia. It contains the extract of 10 traditional medicinal herb and has a potent biological response modifier effect to the immune system.

Tumor cell line: 4T1(luc2) This clone of the cell line contains a luciferase enzyme. The tumor and its metastases can emit a weak light radiation when the substrate of the enzyme is intraperitoneal administered, and can be imaged (and quantified) using a sensitive camera system (IVIS2000 in vivo bioluminescent imaging system).

Experimental Design

Tumor induction: −14 day.
TJ-48 administration: from day −3 to day 18 (50 mg/day, daily, po.)
Oncothermia (radiofrequency waves using capacitive coupling in a condenser arrangement) treatment: day 0 and day 6 (1-2 W reaching tumor core temperature 41-42° C., 25 min total treatment time)

Mice were sacrificed on day 20 and the lung was imaged ex vivo to detect metastasis. Histomorphological examination of the primary tumor and the metastases in the lung were performed as previously described.

Experimental animal groups:
1. Untreated contol (4 mice)
2. TJ-48 group: the mice were treated only with TJ48 (4 mice); The TJ-48 was orally administered using gastric probe.
3. Oncothermia (radiofrequency waves using capacitive coupling in a condenser arrangement) group: the mice were treated only with radiofrequency waves using capacitive coupling in a condenser arrangement on day 0 and day 6 (4 mice)
4. Oncothermia+TJ-48 group: the mice were treated with TJ-48 and Oncothermia (radiofrequency waves using capacitive coupling in a condenser arrangement) on day 0 and day 6 (4 mice)

The tumor volume of the induced primary tumor was evaluated from day 0 to day 13. As shown in FIG. 48, the administration of oncothermia (radiofrequency waves using capacitive coupling in a condenser arrangement) in association with TJ-48 resulted in a significant reduction of the tumor volume.

Example 15: Experimental Demonstration of the Vaccination Effect of the Inventive Method The experimental design, the tumor model (4T1) and the experimental animal groups are the same as described in example 14.

Abbreviations used in this document:
Evaluation Methods:
I. Investigations of the Survival Time of the Animals in the Experimental Groups.

Significant increase in the survival time of the group treated with oncothermia and immune stimulant indirectly prove the vaccination effect of the method.

II. Evaluation of the Vaccination Efficiency Using an ELISPOT Assay

The enzyme-linked immunosorbent spot (ELISPOT) assay is a common method for monitoring immune responses in humans and animals. The ELISPOT assay is based on, and was developed from a modified version of the ELISA immunoassay. ELISPOT assays were originally developed to enumerate B cells secreting antigen-specific antibodies, and have subsequently been adapted for various tasks, especially the identification and enumeration of cytokine-producing cells at the single cell level. Simply put, at appropriate conditions the ELISPOT assay allows visualization of the secretory product of individual activated or responding cells. Each spot that develops in the assay represents a single reactive cell. Thus, the ELISPOT assay provides both qualitative (type of immune protein) and quantitative (number of responding cells) information. For antitumor vaccination evaluation the IFN-gamma ELISPOT assay is the widely used and accepted method.

Short description of the design of the ELISPOT study (ELISPOT assay kits for mouse commercially available from BDBiosciences):
1. Collection of the cells of interest (peripherial blood mononuclear cell (PBMC) or spleen originated cells) from the animals of the experimental groups. Samples were pooled from individual animals according to the experimental groups. Experimental Groups: untreated control animals; oncothermia treated animals, animals treated with immune-stimulants; oncothermia treatment and immunostimulation treatment is combined
2. Incubation of samples from cells of interest with 4T1 tumor cells
3. Performance of an ELISPOT assay according to manufactures protocol
4. Evaluation of the study: In case of successful vaccination effect the OTM+CIS samples show the highest number of spots in the assay.

III. Evaluation of the Vaccination Efficiency Using a Flow-Cytometric Analysis (FACS)

CD4+ and CD8+ T cell population from PBMC can be investigated using flow-cytometry analysis and appropriate Antibodies. The blood samples can be pooled also in this experiment. In case of successful vaccination, the ratio of the CD4+ and CD8+ positive cells will be significantly higher in the OTM+CIS group compared to the other groups.

VI. Evaluation of the Vaccination Efficiency (T Cell Response) Using an IHCH Analysis in the Tumor and Metastasis Samples:

Infiltration of the primary tumor and its metastases are the hallmark of the potent antitumor immune-response. (i.e. successful antitumor vaccination).

IHCH investigations of the infiltrated T cell population can provide an important supportive information about the outcome of the vaccination process. In case of high CD8 positivity in the primary tumor, or especially in the metastases means stronger antitumor immune reactions, and better vaccination efficiency.

What is claimed is:
1. A method for non-invasive treatment of primary cancer and its metastases or for non-invasive prevention of relapse of a cancer disease or for non-invasive vaccination of patient with increased risk to develop cancer, consisting of administering a non-specific immune stimulant to a patient in association with radiofrequency waves applied non-invasively using capacitive coupling in a condenser arrangement, wherein said cancer is colon cancer or breast cancer, the non-specific immune stimulant is Xiao-Aiping, and the frequency of the radiofrequency waves is between 10 kHz and 50 MHz.

2. The method according to claim 1, wherein the condenser arrangement comprises at least one electrode and at least one counter-electrode, wherein the patient is the dielectric material in between.

3. The method according to claim 1, wherein an antenna like in an RF arrangement with radiative coupling is not used for administering the radiofrequency waves.

4. The method according to claim 1, wherein the radiofrequency waves are administered systemically.

5. The method according to claim 1, wherein administering radiofrequency waves does not increase the body temperature of the patient or the temperature of a treated area of the patient.

6. The method according to claim 1, wherein the frequency of the radiofrequency waves is between 130 kHz and 42 MHz.

* * * * *